United States Patent
Voladri et al.

(10) Patent No.: US 8,455,230 B2
(45) Date of Patent: Jun. 4, 2013

(54) POLYNUCLEOTIDES ENCODING ENGINEERED KETOREDUCTASE POLYPEPTIDES

(75) Inventors: Rama Voladri, Milpitas, CA (US); Owen Gooding, San Jose, CA (US); Stephan Jenne, Foster City, CA (US); Emily Mundorff, Poughkeepsie, NY (US)

(73) Assignees: Codexis, Inc., Redwood City, CA (US); Pfizer, Inc., New York, NY (US)

( * ) Notice: Subject to any disclaimer, the term of this patent is extended or adjusted under 35 U.S.C. 154(b) by 0 days.

(21) Appl. No.: 13/610,723

(22) Filed: Sep. 11, 2012

(65) Prior Publication Data
US 2013/0005018 A1    Jan. 3, 2013

Related U.S. Application Data

(62) Division of application No. 12/545,761, filed on Aug. 21, 2009, now Pat. No. 8,288,131.

(60) Provisional application No. 61/092,238, filed on Aug. 27, 2008.

(51) Int. Cl.
C12N 9/02   (2006.01)
C12N 1/38   (2006.01)
C12N 15/00  (2006.01)
C07H 21/04  (2006.01)

(52) U.S. Cl.
USPC ........ 435/189; 435/243; 435/320.1; 536/23.2

(58) Field of Classification Search
None
See application file for complete search history.

(56) References Cited

U.S. PATENT DOCUMENTS

| | | | |
|---|---|---|---|
| 5,538,867 A | 7/1996 | Durliat et al. | |
| 5,559,030 A | 9/1996 | Matsuyama et al. | |
| 5,700,670 A | 12/1997 | Yamagishi et al. | |
| 5,891,685 A | 4/1999 | Yamagishi et al. | |
| 5,891,703 A | 4/1999 | Van Der Laan et al. | |
| 6,033,823 A | 3/2000 | Van Der Laan et al. | |
| 6,117,679 A | 9/2000 | Stemmer | |
| 6,376,246 B1 | 4/2002 | Crameri et al. | |
| 6,399,339 B1 | 6/2002 | Wolberg et al. | |
| 6,495,023 B1 | 12/2002 | Zeikus et al. | |
| 6,586,182 B1 | 7/2003 | Patten et al. | |
| 6,645,746 B1 | 11/2003 | Kizaki et al. | |
| 6,800,477 B2 | 10/2004 | Patel et al. | |
| 2004/0214297 A1 | 10/2004 | Davis et al. | |
| 2005/0095619 A1 | 5/2005 | Davis et al. | |
| 2005/0124029 A1 | 6/2005 | Van Der Laan et al. | |
| 2005/0153417 A1 | 7/2005 | Davis et al. | |
| 2006/0195947 A1 | 8/2006 | Davis et al. | |
| 2006/0292678 A1 | 12/2006 | Nanduri et al. | |
| 2007/0275436 A1 | 11/2007 | Zazopoulos et al. | |
| 2008/0220990 A1 | 9/2008 | Fox | |
| 2008/0248539 A1 | 10/2008 | Giver et al. | |
| 2008/0318295 A1 | 12/2008 | Ching et al. | |
| 2009/0093031 A1 | 4/2009 | Liang et al. | |
| 2009/0155863 A1 | 6/2009 | Liang et al. | |
| 2009/0162909 A1 | 6/2009 | Campopiano et al. | |
| 2009/0191605 A1 | 7/2009 | Liang et al. | |
| 2009/0312196 A1 | 12/2009 | Colbeck et al. | |

FOREIGN PATENT DOCUMENTS

| | | |
|---|---|---|
| WO | WO95/22625 | 8/1995 |
| WO | WO97/20078 | 6/1997 |
| WO | WO97/35966 | 10/1997 |
| WO | WO98/27230 | 6/1998 |
| WO | WO00/42651 | 7/2000 |
| WO | WO0175767 A2 | 10/2001 |
| WO | WO2005018579 A2 | 3/2005 |

OTHER PUBLICATIONS

Black et al., "Creation of drug-specific herpes simplex virus type 1 thymidine kinase mutants for gene therapy," Proc. Natl. Acad. Sci USA 93:3525-3529 (1996).
Dicosimo et al., "Enantioselective Oxidation of 2-Methyl-1-Alkanois by Alcohol Oxidase from Methylotrophic Yeasts," Biorg MedicChem Lett. 5:1383-1388 (1995).
Effenberger et al., "Lipase-Catalyzed resolution of racemic 2-Alkyl substituted 1-Alkanols," Asymmetry 4:823-833 (1993).
Genbank accession No. CP00046 for Lactobacillus brevis dated Mar. 5, 2010.
Gooding et al., "Development of a Practical Biocatalytic process for (R)-2-Methylpentanol," Organic Proc. Research &Dev. 14:119-126 (2010).
Hogberg et al., "Enantioselective Synthesis of (S)-2-Methyl-1-alkanols via Bakers' Yeast mediated reduction of α-Methyl-2-thiophenepropenals," J. Org. Chem., 57:2052 (1992).
Myers et al., "Pseudoephedrine as a practical chiral auxiliary for the synthesis of highly enantiomerically enriched carboxylic acids, alcohols, aldehydes, and Ketones," JACS 119:6496-6511 (1997).
Niefind et al., "The Crystal Structure of R-specific Alcohol Dehydrogenase from Lactobacillus brevis Suggests the Structural Basis of its Metal Dependency," Journal Mol. Biol. 327:317-328 (2003).
O'Hare et al. "High-Throughput Mutagenesis to Evaluate Models of Stereochemical Control in Ketoreductase Domains from the Erythromycin Polyketide Synthase," Chem. &Biol. 13:3:287-296 (2006).
Ostergaard et al., "Stereochemistry of Catalysis by the Ketoreductase Activity in the First Extension Module of the Erythromycin Polyketide Synthase," Biochem. 41:8:2719-2726 (2002).
Savolainen et al., "α-Methylacyl-CoA Racemase from Mycobacterium tuberculosis," Journal Biol. Chem. 280:13:12611-12620 (2005).
Schlieben et al., "Atomic Resolution Structures of R-Specific Alcohol Dehydrogenase from Lactobacillus brevis Provide the Structural Bases of its Substrate and Cosubstrate Specificity," Journal Mol. Biol. 349:801-813 (2005).

(Continued)

Primary Examiner — Tekchand Saidha
Assistant Examiner — Md. Younus Meah
(74) Attorney, Agent, or Firm — Codexis, Inc.

(57) ABSTRACT

The present disclosure provides engineered ketoreductase enzymes having improved properties as compared to a naturally occurring wild-type ketoreductase enzyme including the capability of stereospecifically reducing (R)-2-methylpentanal to (R)-2-methylpentanol. Also provided are polynucleotides encoding the engineered ketoreductase enzymes, host cells capable of expressing the engineered ketoreductase enzymes, and methods of using the engineered ketoreductase enzymes to produce (R)-2-methylpentanol and related compounds.

11 Claims, 1 Drawing Sheet

OTHER PUBLICATIONS

Stemmer et al., "DNA shuffling by random fragmentation and reassembly: in vitro recombination for molecular evolution," *Prod. Natl. Acad. Sci. USA* 91:10747-10751 (1994).

Sulzenbacher et al., "Crystal Structure of *E. coli* Alcohol Dehydrogenase YqhD: Evidence of a Covalently Modified NADP Coenzyme," *Journal Mol. Biol.* 342:489-502 (2004).

Tewari et al., "A Thermodynamic study of the Ketoreductase-Catalyzed Reduction of 2-Alkanones in Non-Aqueous Solvents," *J. Chem. Thermodynamics.* 37:1:3:89-96 (2005).

Zhao et al., "Molecular evolution by staggered extension process (StEP) in vitro recombination," *Nature Biotech.* 16:258 (1999).

International Search Report of the International Searching Authority of PCT/US2009/054664, mailed Mar. 18, 2010.

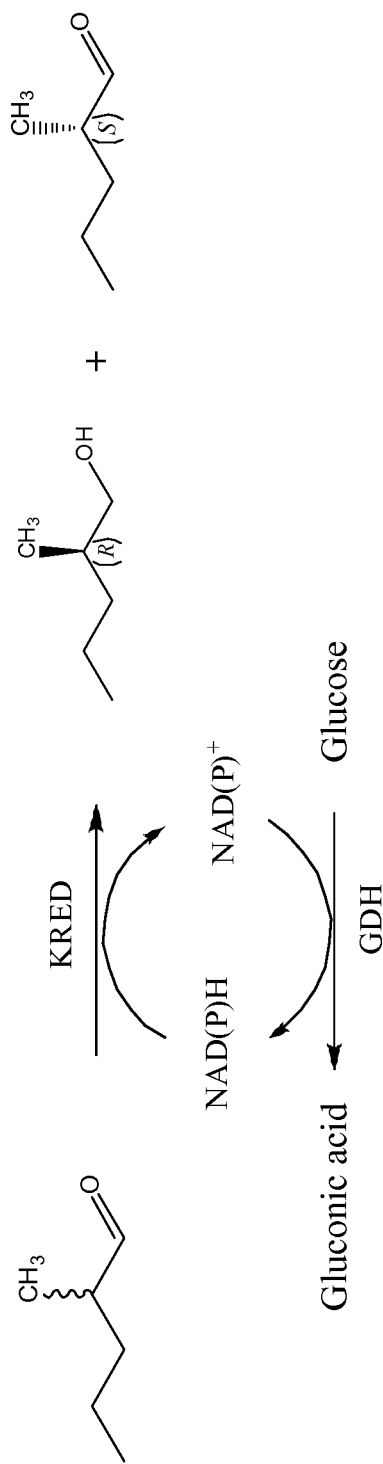

US 8,455,230 B2

POLYNUCLEOTIDES ENCODING ENGINEERED KETOREDUCTASE POLYPEPTIDES

1. CROSS REFERENCE TO RELATED APPLICATIONS

The present application claims priority under 35 U.S.C. §120 of U.S.S.N. 12/545,761 filed Aug. 21, 2009, now U.S. Pat. No. 8,288,131 and under 35 U.S.C. §119 of U.S. provisional application 61/092,238, filed Aug. 27, 2008, each of which is hereby incorporated by reference herein.

2. TECHNICAL FIELD

The present disclosure relates to engineered polypeptides and uses of the polypeptides to stereospecifically reduce (R)-2-methylpentanal to (R)-2-methylpentanol.

3. REFERENCE TO SEQUENCE LISTING, TABLE OR COMPUTER PROGRAM

The Sequence Listing concurrently submitted electronically under 37 C.F.R. §1.821 via EFS-Web in a computer readable form (CRF) as file name CX2-023_ST25.txt is herein incorporated by reference. The electronic copy of the Sequence Listing was created on Jul. 30, 2009, with a file size of 106 Kbytes. This Sequence Listing is identical except for minor formatting corrections to 376247-019USP1.txt, created on Aug. 26, 2008, with a file size of 103 Kbytes and was incorporated by reference in the priority U.S. provisional application 61/092,238.

4. BACKGROUND

Enzymes belonging to the ketoreductase (KRED) or carbonyl reductase class (EC1.1.1.184) are useful for the production of optically active alcohols by stereoselective reduction of corresponding prostereoisomeric ketone substrates and by stereospecific reduction of corresponding racemic aldehyde and ketone substrates. KREDs typically convert ketone and aldehyde substrates to the corresponding alcohol product, but may also catalyze the reverse reaction, oxidation of an alcohol substrate to the corresponding ketone/aldehyde product. The reduction of ketones and aldehydes and the oxidation of alcohols by enzymes such as KRED requires a co-factor, most commonly reduced nicotinamide adenine dinucleotide (NADH) or reduced nicotinamide adenine dinucleotide phosphate (NADPH), and nicotinamide adenine dinucleotide (NAD) or nicotinamide adenine dinucleotide phosphate (NADP) for the oxidation reaction. NADH and NADPH serve as electron donors, while NAD and NADP serve as electron acceptors. It is frequently observed that ketoreductases and alcohol dehydrogenases accept either the phosphorylated or the non-phosphorylated co-factor (in its oxidized and reduced state).

KRED enzymes can be found in a wide range of bacteria and yeasts (for reviews: Kraus and Waldman, *Enzyme catalysis in organic synthesis*, Vols. 1&2.VCH Weinheim 1995; Faber, K., Biotransformations in organic chemistry, 4th Ed. Springer, Berlin Heidelberg New York. 2000; Hummel and Kula, 1989, *Eur. J. Biochem.* 184:1-13). Several KRED gene and enzyme sequences have been reported, e.g., *Candida magnoliae* (Genbank Acc. No. JC7338; GI:11360538) *Candida parapsilosis* (Genbank Acc. No. BAA24528.1; GI:2815409), *Sporobolomyces salmonicolor* (Genbank Acc. No. AF160799; GI:6539734).

In order to circumvent many chemical synthetic procedures for the production of key compounds, ketoreductases are being increasingly employed for the enzymatic conversion of different keto or aldehyde substrates to chiral alcohol products. These applications can employ whole cells expressing the ketoreductase for biocatalytic ketone reductions, or purified enzymes in those instances where presence of multiple ketoreductases in whole cells would adversely affect the stereopurity and yield of the desired product. For in vitro applications, a co-factor (NADH or NADPH) regenerating enzyme such as glucose dehydrogenase (GDH), formate dehydrogenase etc. is used in conjunction with the ketoreductase. Examples using ketoreductases to generate useful chemical compounds include asymmetric reduction of 4-chloroacetoacetate esters (Zhou, 1983, *J. Am. Chem. Soc.* 105:5925-5926; Santaniello, *J. Chem. Res.* (S) 1984:132-133; U.S. Pat. No. 5,559,030; U.S. Pat. No. 5,700,670 and U.S. Pat. No. 5,891,685), reduction of dioxocarboxylic acids (e.g., U.S. Pat. No. 6,399,339), reduction of tert-butyl (S) chloro-5-hydroxy-3-oxohexanoate (e.g., U.S. Pat. No. 6,645,746 and WO 01/40450), reduction of pyrrolotriazine-based compounds (e.g., U.S. application No. 2006/0286646); reduction of substituted acetophenones (e.g., U.S. Pat. No. 6,800,477); and reduction of ketothiolanes (WO 2005/054491).

It is desirable to identify other ketoreductase enzymes that can be used to carryout conversion of various keto substrates to its corresponding chiral alcohol products.

5. SUMMARY

The present disclosure provides ketoreductase polypeptides having the ability to stereospecifically reduce (R)-2-methylpentanal ("the substrate") to (R)-2-methylpentanol ("the product"), polynucleotides encoding such polypeptides, and methods of using the polypeptides. Generally, the (R)-2-methylpentanal is in a mixture of R and S enantiomers, such as a racemic substrate mixture, and the ketoreductase polypeptides of the disclosure are capable of resolving 2-methylpentanal mixture by reduction of the (R)-enantiomer to (R)-2-methylpentanol while leaving the (S)-enantiomer unreacted.

In one aspect, the ketoreductase polypeptides described herein have an amino acid sequence that has one or more amino acid differences as compared to a reference amino acid sequence of a wild-type ketoreductase or an engineered ketoreductase that result in an improved property of the enzyme for the defined keto substrate. Generally, the engineered ketoreductase polypeptides have an improved property as compared to the naturally-occurring wild-type ketoreductase enzymes obtained from *Lactobacillus kefir* ("*L. kefir*"; SEQ ID NO:4), *Lactobacillus brevis* ("*L. brevis*"; SEQ ID NO:2), or *Lactobacillus minor* ("*L. minor*," SEQ ID NO:48). In some embodiments, the polypeptides of the disclosure have an improved property as compared to another engineered polypeptide, such as SEQ ID NO:6. Improvements in enzyme property can include, among others, enhancement of enzyme activity, stereoselectivity, sterospecificity, thermostability, solvent stability, or reduced product inhibition, or combinations thereof, such as stereospecificity and enzyme activity. In the present disclosure, the ketoreductase polypeptides have, as compared to the amino acid sequence of SEQ ID NO:2, 4, or 48, the following features: residue corresponding to residue 145 is a polar residue, and residue corresponding to residue 153 is a polar residue. In some embodiments, the ketoreductase polypeptides have, as compared to the amino acid sequence of SEQ ID NO:2, 4, or 48, the following features: the residue corresponding to residue 145 is a serine, and the residue corresponding to residue 153 is a glutamine. In some embodiments, the ketoreductase polypeptides have, as compared to the amino acid sequence of SEQ ID NO:2, 4, or 48, the following features: the residue corresponding to residue 153 is a polar residue and the residue corresponding to residue 145 is not a polar residue. In some embodiments, the ketoreductase polypeptides have, as compared to the amino acid sequence of SEQ ID NO:2, 4, or 48, the following features: the residue corresponding to residue 153 is a glutamine and the residue corresponding to residue 145 is not serine.

In some embodiments, the ketoreductase polypeptides are improved as compared to SEQ ID NO:4 with respect to their enzymatic activity, i.e., their rate of converting the substrate to the product. In some embodiments, the ketoreductase polypeptides are capable of converting the substrate to the product at a rate that is at least 1.5 times, 5-times, 10-times, 25-times, 50-times, 75-times, 100-times, 150-times, 200-times, 250-times, or 300-times or more over the rate of SEQ ID NO:4 include SEQ ID NO:6, 8, 10, 12, 14, 16, 18, 20, 22, 24, 26, 28, 30, 32, 34, 36, 38, 40, 42, and 44.

In some embodiments, the ketoreductase polypeptide is a highly stereospecific ketoreductase that can reduce the (R)-enantiomer of 2-methylpentanal to give (R)-2-methylpentanol with a stereomeric excess that is greater than about 85%, 90%, 95%, 96%, 97%, 98%, 99%, or 99.9%, or more. Exemplary ketoreductase polypeptides with such high stereospecificity include, but are not limited to, the polypeptides comprising the amino acid sequences corresponding to SEQ ID NO:6, 8, 10, 12, 14, 16, 18, 20, 22, 24, 26, 28, 30, 32, 34, 36, 38, 40, 42, and 44.

In some embodiments, the ketoreductase polypeptides are capable of reducing the substrate to the product at a stereomeric excess of at least about 90%, and is capable of converting at least about 40% of a racemic mixture of R and S enantiomers to the product in less than 24 hours when the reaction is conducted with about 1% of the ketoreductase polypeptide by weight with respect to the weight of the amount of substrate. Exemplary polypeptides that have this capability include, but are not limited to, polypeptides comprising the sequences that correspond to SEQ ID NO:24, 26, 28, and 44.

In some embodiments, the ketoreductase polypeptides are improved as compared to SEQ ID NO:4 with respect to their thermostability, as determined by an increase in the rate of enzymatic activity over SEQ ID NO:4 under high temperatures. Exemplary thermally stable ketoreductase polypeptides include polypeptides comprising amino acid sequences that correspond to SEQ ID NO:24, 32, 34, 36, 38, and 40.

In some embodiments, an improved ketoreductase polypeptide of the disclosure comprises an amino acid sequence that corresponds to the sequence formulas as presented in SEQ ID NO:45, 46, or 57. SEQ ID NO:45 is based on the wild-type amino acid sequence of the *Lactobacillus kefir* ketoreductase (SEQ ID NO:4); SEQ ID NO:46 is based on the wild-type amino acid sequence of the *Lactobacillus brevis* ketoreductase (SEQ ID NO:2); and SEQ ID NO:57 is based on the wild-type amino acid sequence of the *Lactobacillus minor* ketoreductase (SEQ ID NO:57). Each of the sequence formulas specify that the amino acid residue corresponding to residue X145 is a polar amino acid, and/or residue X153 is a polar amino acid.

In some embodiments, an improved ketoreductase polypeptide of the disclosure is based on the sequence formulas of SEQ ID NO:45, 46, or 57 and can comprise an amino acid sequence that is at least about 85%, 86%, 87%, 88%, 89%, 90%, 91%, 92%, 93%, 94%, 95%, 96%, 97%, 98%, or 99% identical to a reference sequence based on SEQ ID NO:2, 4 or 48, or a region thereof, such as residues 90-211, with the proviso that the amino acid residue corresponding to residue X145 and residue corresponding to X153 have the features described above. For example, in some embodiments, the reference sequence as well as the ketoreductase polypeptide comprises an amino acid sequence in which at least the residue corresponding to residue X145 is a polar amino acid, and the residue corresponding to residue 153 is a polar amino acid. In some embodiments, the reference sequence as well as the ketoreductase polypeptide comprise an amino acid sequence in which at least the residue corresponding to residue X145 is a serine, and the residue corresponding to residue 153 is a glutamine. In some embodiments, the ketoreductase polypeptide as well as the reference polypeptide have an amino acid sequence in which the residue corresponding to residue X153 is a polar residue and the residue corresponding to residue X145 is not a polar residue. In some embodiments, the ketoreductase polypeptide as well as the reference polypeptide have an amino acid sequence in which the residue corresponding to residue X153 is a glutamine and the residue corresponding to residue X145 is not serine.

In some embodiments, the ketoreductase polypeptides herein, as based on the sequence formulas of SEQ ID NO:45, 46, or 57, can additionally have one or more amino acid residue differences as compared to the reference sequences above. These differences can be amino acid insertions, deletions, substitutions, or any combination of such changes. In some embodiments, the amino acid sequence differences can comprise non-conservative, conservative, as well as a combination of non-conservative and conservative amino acid substitutions. Various amino acid residue positions where such changes can be made are described herein.

In some embodiments, the ketoreductase polypeptides have a greater E-value (stereospecificity) for the stereospecific reduction of 2-methylpentanal as compared to SEQ ID NO:4. In some embodiments, the E-value of the ketoreductase polypeptides can be $\geq 50$, $\geq 100$, $\geq 200$, or $\geq 300$. In some embodiments, the E-value of the ketoreductase polypeptides can be from 50 to 100, from 101 to 200, from 201 to 300, or >301. Exemplary polypeptides that have such E-values include, but are not limited to, polypeptides comprising the sequences that correspond to SEQ ID NO:6, 8, 10, 12, 14, 16, 18, 20, 22, 24, 26, 28, 30, 32, 34, 36, 38, 40, 42, and 44. Exemplary polypeptides with E-values from 50 to 100 include, but are not limited to, polypeptides comprising the sequences that correspond to SEQ ID NO:8, 22, 30, 32, 34, 36, 38, 40, and 44. Exemplary polypeptides with E-values from 101 to 200 include, but are not limited to, polypeptides comprising the sequences that correspond to SEQ ID NO:6, 10, 12, 14, 16, 20, and 42. Exemplary polypeptides with E-values from 201 to 300 include, but are not limited to, polypeptides comprising the sequences that correspond to SEQ ID NO:26, 28, and 44. Exemplary polypeptides with E-values greater than 301 include, but are not limited to, polypeptides comprising the sequences that correspond to SEQ ID NO:24.

In some embodiments, the ketoreductase polypeptides of the disclosure can comprise a region or domain having an amino acid sequence that is at least about 85%, 86%, 87%, 88%, 89%, 90%, 91%, 92%, 93%, 94%, 95%, 96%, 97%, 98%, or 99% identical to a reference sequence based on a region or domain of SEQ ID NO:2, SEQ ID NO:4 or SEQ ID NO:48, such as residues 90-211, with the proviso that the residue corresponding to X145 and residue corresponding to X153 are as specified herein.

In some embodiments, an improved ketoreductase comprises an amino acid sequence that is at least about 85%, 86%, 87%, 88%, 89%, 90%, 91%, 92%, 93%, 94%, 95%, 96%, 97%, 98%, or 99% identical to the amino acid sequence corresponding to SEQ ID NO: SEQ ID NO:6, 8, 10, 12, 14, 16, 18, 20, 22, 24, 26, 28, 30, 32, 34, 36, 38, 40, 42, and 44, wherein the improved ketoreductase polypeptide amino acid sequence includes any one set of the specified amino acid substitution combinations presented in Table 2. In some embodiments, these ketoreductase polypeptides can have from about 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-25, 1-30, 1-35 or about 1-40 mutations at other amino acid residues. In some embodiments, the mutations comprise conservative mutations.

In another aspect, the present disclosure provides polynucleotides encoding the engineered ketoreductases described herein or polynucleotides that hybridize to such polynucleotides under highly stringent conditions. The polynucleotide can include promoters and other regulatory elements useful for expression of the encoded engineered ketoreductase, and can utilize codons optimized for specific desired expression systems. Exemplary polynucleotides include, but are not limited to, SEQ ID NO:5, 7, 9, 11, 13, 15, 17, 19, 21, 23, 25, 27, 29, 31, 33, 35, 37, 39, 41 and 43. Exemplary polynucleotides also include polynucleotides encoding polypeptides encompassed by the sequence formulas of SEQ ID NOS:45, 46, and 57.

In another aspect, the present disclosure provides host cells comprising the polynucleotides and/or expression vectors described herein. The host cells may be *L. kefir, L. brevis, L. minor*, or they may be a different organism. The host cells can be used for the expression and isolation of the engineered ketoreductase enzymes described herein, or, alternatively, they can be used directly for the resolution of the 2-methylpentanal substrate to the chiral (R)-2-methylpentanol product.

As described herein, the ketoreductase enzymes described herein are capable of catalyzing the stereospecific reduction reaction of the aldehyde group of (R)-2-methylpentanal of structural formula (I), such as in a mixture of (R)-2-methylpentanal and (S)-2-methylpentanal,

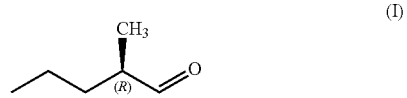
(I)

to the corresponding chiral (R)-2-methylpentanol of structural formula (II):

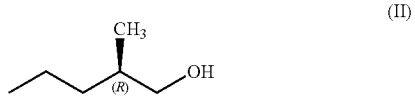
(II)

In some embodiments, the invention provides a method for resolving a mixture of (R) and (S) 2-methylpentanal (III)

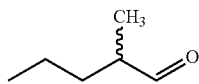
(III)

such as a racemic mixture, by reduction of the (R)-enantiomer to (R)-2-methylpentanol while leaving the (S)-enantiomer unreacted. The method can comprise contacting or incubating 2-methylpentanal with a ketoreducase polypeptide of the disclosure under reaction conditions suitable for reducing or converting the (R)-2-methylpentanal to (R)-2-methylpentanol while leaving the (S)-enantiomer unreacted (IV).

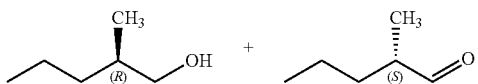
(IV)

Whether carrying out the method with whole cells, cell extracts or purified ketoreductase enzymes, a single ketoreductase enzyme may be used or, alternatively, mixtures of two or more ketoreductase enzymes may be used.

In some embodiments of this method, the substrate is reduced to product of greater than about 98% stereomeric excess, wherein the ketoreductase polypeptide comprises a sequence that corresponds to SEQ ID NO:24, 26, 28, and 44. In some embodiments of the disclosed method, the substrate is reduced to product of greater than about 99% stereomeric excess, wherein the ketoreductase polypeptide comprises a sequence that corresponds to SEQ ID NO:24. In some embodiments of this method, at least about 40% of a racemic mixture of R and S enantiomers is reduced to the product in less than or equal to about 24 hours when the method is conducted with greater than or equal to about 220 g/L of substrate and $\leq 2$ g/L enzyme but >0 g/L enzyme. In some embodiments, at least about 45% of the racemic substrate is reduced to the product in less than or equal to about 24 hours when the method is conducted with about 220 g/L of substrate and about 2 g/L enzyme.

In some embodiments of this method for reducing the substrate to the product, at least about 98% of the substrate is reduced to the product in less than or equal to about 24 hours when the method is conducted with greater than or equal to about 220 g/L of substrate and the enzyme is about 1% of the substrate concentration or the enzyme concentration is less than about 1% of the substrate concentration but greater than 0% of the substrate concentration, wherein the ketoreductase polypeptide comprises an amino acid sequence corresponding to SEQ ID NO:24, 26, 28, and 44.

6. BRIEF DESCRIPTION OF THE FIGURES

FIG. 1 illustrates the role of ketoreductases (KRED) in the conversion of the substrate compound of formula (I), supra, to the corresponding chiral alcohol product of formula (II), supra. In this reaction, the (R)-enantiomer in the substrate, racemic 2-methylveraldehyde, is reduced biocatalytically to the corresponding (R)-2-methylpentanol, while the (S)-enantiomer remains unreacted. This reduction uses a KRED described herein and a co-factor such as NADPH. In exemplary embodiments, a secondary alcohol dehydrogenase, including a KRED, can be used to convert/recycle $NADP^+$ to NADPH or glucose dehydrogenase (GDH) can be used to convert/recycle $NADP^+$ to NADPH. In the recycling reaction, isopropanol is converted to acetone or glucose is converted to gluconic acid, which in turn is converted to its sodium salt (sodium gluconate) with the addition of sodium hydroxide. Example 11 provides a non-limiting method for conducting the reaction.

7. DETAILED DESCRIPTION

7.1 Definitions

As used herein, the following terms are intended to have the following meanings.

"Ketoreductase" and "KRED" are used interchangeably herein to refer to a polypeptide having an enzymatic capability of reducing a carbonyl group to its corresponding alcohol group. More specifically, the ketoreductase polypeptides of the disclosure are capable of stereospecifically reducing the compound of formula (I), supra to the corresponding product of formula (II), supra. The polypeptide typically utilizes a cofactor, for example, reduced nicotinamide adenine dinucleotide (NADH) or reduced nicotinamide adenine dinucleotide phosphate (NADPH) as the reducing agent. Ketoreductases as used herein include naturally occurring (wild type ("wt")) ketoreductases as well as non-naturally occurring engineered polypeptides generated by human manipulation.

"Coding sequence" refers to that portion of a nucleic acid (e.g., a gene) that encodes an amino acid sequence of a protein.

"Naturally-occurring" or "wild-type" refers to the form found in nature. For example, a naturally occurring or wild-type polypeptide or polynucleotide sequence is a sequence present in an organism that can be isolated from a source in nature and which has not been intentionally modified by human manipulation.

"Recombinant" when used with reference to, e.g., a cell, nucleic acid, or polypeptide, refers to a material, or a material corresponding to the natural, naturally-occurring, wild-type, or native form of the material, that has been modified in a manner that would not otherwise exist in nature, or is identical thereto but produced or derived from synthetic materials and/or by manipulation using recombinant techniques. Non-limiting examples include, among others, recombinant cells expressing genes that are not found within the native or naturally-occurring (non-recombinant) form of the cell or express native genes that are otherwise expressed at a different level.

"Percentage of sequence identity" and "percentage homology" are used interchangeably herein to refer to comparisons among polynucleotides and polypeptides, and are determined by comparing two optimally aligned sequences over a comparison window, wherein the portion of the polynucleotide or polypeptide sequence in the comparison window may comprise additions or deletions (i.e., gaps) as compared to the reference sequence (which does not comprise additions or deletions) for optimal alignment of the two sequences. The percentage may be calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity. Alternatively, the percentage may be calculated by determining the number of positions at which either the identical nucleic acid base or amino acid residue occurs in both sequences or a nucleic acid base or amino acid residue is aligned with a gap to yield the number of matched positions, dividing the number of matched positions by the total number of positions in the window of comparison and multiplying the result by 100 to yield the percentage of sequence identity. Those of skill in the art appreciate that there are many established algorithms available to align two sequences. Optimal alignment of sequences for comparison can be conducted, e.g., by the local homology algorithm of Smith and Waterman, 1981, *Adv. Appl. Math.* 2:482, by the homology alignment algorithm of Needleman and Wunsch, 1970, *J. Mol. Biol.* 48:443, by the search for similarity method of Pearson and Lipman, 1988, *Proc. Natl. Acad. Sci. USA* 85:2444, by computerized implementations of these algorithms (GAP, BESTFIT, FASTA, and TFASTA in the GCG Wisconsin Software Package), or by visual inspection (see generally, *Current Protocols in Molecular Biology*, F. M. Ausubel et al., eds., Current Protocols, a joint venture between Greene Publishing Associates, Inc. and John Wiley & Sons, Inc., (1995 Supplement) ("Ausubel")). Examples of algorithms that are suitable for determining percent sequence identity and sequence similarity are the BLAST and BLAST 2.0 algorithms, which are described in Altschul et al., 1990, *J. Mol. Biol.* 215: 403-410 and Altschul et al., 1977, *Nucleic Acids Res.* 3389-3402, respectively. Software for performing BLAST analyses is publicly available through the National Center for Biotechnology Information website. This algorithm involves first identifying high scoring sequence pairs (HSPs) by identifying short words of length W in the query sequence, which either match or satisfy some positive-valued threshold score T when aligned with a word of the same length in a database sequence. T is referred to as, the neighborhood word score threshold (Altschul et al, supra). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=−4, and a comparison of both strands. For amino acid sequences, the BLASTP program uses as defaults a wordlength (W) of 3, an expectation (E) of 10, and the BLOSUM62 scoring matrix (see Henikoff and Henikoff, 1989, *Proc Natl Acad Sci USA* 89:10915). Exemplary determination of sequence alignment and % sequence identity can employ the BESTFIT or GAP programs in the GCG Wisconsin Software package (Accelrys, Madison, Wis.), using the default parameters provided.

"Reference sequence" refers to a defined sequence used as a basis for a sequence comparison. A reference sequence may be a subset of a larger sequence, for example, a segment of a full-length gene or polypeptide sequence. Generally, a reference sequence is at least 20 nucleotide or amino acid residues in length, at least 25 residues in length, at least 50 residues in length, or the full length of the nucleic acid or polypeptide. Since two polynucleotides or polypeptides may each (1) comprise a sequence (i.e., a portion of the complete sequence) that is similar between the two sequences, and (2) may further comprise a sequence that is divergent between the two sequences, sequence comparisons between two (or more) polynucleotides or polypeptide are typically performed by comparing sequences of the two polynucleotides over a "comparison window" to identify and compare local regions of sequence similarity.

In some embodiments, a reference sequence can be based on a primary amino acid sequence, where the reference sequence is a sequence that can have one or more changes in the primary sequence. For instance, a reference sequence "based on SEQ ID NO:4 having at the residue corresponding to X145a serine" refers to a reference sequence in which the corresponding residue at X145 in SEQ ID NO:4 has been changed to a serine.

"Comparison window" refers to a conceptual segment of at least about 20 contiguous nucleotide positions or amino acids residues wherein a sequence may be compared to a reference sequence of at least 20 contiguous nucleotides or amino acids and wherein the portion of the sequence in the comparison window may comprise additions or deletions (i.e., gaps) of 20 percent or less as compared to the reference sequence (which does not comprise additions or deletions) for optimal alignment of the two sequences. The comparison window can be longer than 20 contiguous residues, and includes, optionally 30, 40, 50, 100, or longer windows.

"Substantial identity" refers to a polynucleotide or polypeptide sequence that has at least 80 percent sequence identity, at least 85 percent identity and 89 to 95 percent sequence identity, more usually at least 99 percent sequence identity as compared to a reference sequence over a comparison window of at least 20 residue positions, frequently over a window of at least 30-50 residues, wherein the percentage of sequence identity is calculated by comparing the reference sequence to a sequence that includes deletions or additions which total 20 percent or less of the reference sequence over the window of comparison. In specific embodiments applied to polypeptides, the term "substantial identity" means that two polypeptide sequences, when optimally aligned, such as by the programs GAP or BESTFIT using default gap weights, share at least 80 percent sequence identity, preferably at least 89 percent sequence identity, at least 95 percent sequence identity or more (e.g., 99 percent sequence identity). Preferably, residue positions which are not identical differ by conservative amino acid substitutions.

Corresponding to", "reference to" or "relative to" when used in the context of the numbering of a given amino acid or polynucleotide sequence refers to the numbering of the residues of a specified reference sequence when the given amino acid or polynucleotide sequence is compared to the reference sequence. In other words, the residue number or residue position of a given polymer is designated with respect to the reference sequence rather than by the actual numerical position of the residue within the given amino acid or polynucleotide sequence. For example, a given amino acid sequence, such as that of an engineered ketoreductase, can be aligned to a reference sequence by introducing gaps to optimize residue matches between the two sequences. In these cases, although the gaps are present, the numbering of the residue in the given amino acid or polynucleotide sequence is made with respect to the reference sequence to which it has been aligned. In some embodiments, unless specifically described otherwise, the terms "Xn", "residue position n", or "residue n", where "n" is the number position of a residue with respect to a reference sequence, are to be used in the context of "corresponding to" as described herein.

"Stereoselectivity" refers to the preferential formation in a chemical or enzymatic reaction of one stereoisomer over another. Stereoselectivity can be partial, where the formation of one stereoisomer is favored over the other, or it may be complete where only one stereoisomer is formed. When the stereoisomers are enantiomers, the stereoselectivity is referred to as enantioselectivity, the fraction (typically reported as a percentage) of one enantiomer in the sum of both. It is commonly alternatively reported in the art (typically as a percentage) as the enantiomeric excess (e.e.) calculated therefrom according to the formula [major enantiomer−minor enantiomer]/[major enantiomer+minor enantiomer]. Where the stereoisomers are diastereoisomers, the stereoselectivity is referred to as diastereoselectivity, the fraction (typically reported as a percentage) of one diastereomer in a mixture of two diastereomers, commonly alternatively reported as the diastereomeric excess (d.e.). Enantiomeric excess and diastereomeric excess are types of stereomeric excess.

"Highly stereoselective" refers to a ketoreductase polypeptide that is capable of converting or reducing the substrate to the corresponding (R)-alcohol with at least about 98% stereomeric excess.

"Stereospecificity" refers to the preferential conversion in a chemical or enzymatic reaction of one stereoisomer over another. When the stereoisomers are enantiomers, the stereospecificity of the reaction is also called "enantiospecificity". Stereospecificity can be partial, where the conversion of one stereoisomer is favored over the other, or it may be complete where only one stereoisomer is converted. The E-value (the enantiomeric ratio) is a quantitative index of enantiospecificity, independent of the substrate and enzyme concentrations and can be calculated as described in Chen et al., 1987, *J Am. Chem. Soc.* 109:2812-2817, incorporated herein by reference.

"Highly stereospecific" refers to a ketoreductase polypeptide that is capable of converting only one of the stereoisomers in the substrate to the corresponding (R)-alcohol leaving unreacted aldehyde behind at 45 to 55% conversion.

"Chemoselectivity" refers to the preferential formation in a chemical or enzymatic reaction of one product over another.

"Improved enzyme property" refers to a ketoreductase polypeptide that exhibits an improvement in any enzyme property as compared to a reference ketoreductase. For the engineered ketoreductase polypeptides described herein, the comparison is generally made to the wild-type ketoreductase enzyme, although in some embodiments, the reference ketoreductase can be another improved engineered ketoreductase. Enzyme properties for which improvement is desirable include, but are not limited to, enzymatic activity (which can be expressed in terms of percent conversion of the substrate), thermal stability, pH activity profile, cofactor requirements, refractoriness to inhibitors (e.g., product inhibition), stereospecificity, stereoselectivity (including enantioselectivity), substrate inhibition, substrate tolerance, solvent (e.g. isopropylalcohol) tolerance, and substrate (e.g. aldehyde) tolerance.

"Increased enzymatic activity" refers to an improved property of the engineered ketoreductase polypeptides, which can be represented by an increase in specific activity (e.g., product produced/time/weight protein) or an increase in percent conversion of the substrate to the product (e.g., percent conversion of starting amount of substrate to product in a specified time period using a specified amount of KRED) as compared to the reference ketoreductase enzyme. Exemplary methods to determine enzyme activity are provided in the Examples. Any property relating to enzyme activity may be affected, including the classical enzyme properties of $K_m$, $V_{max}$ or $k_{cat}$, changes of which can lead to increased enzymatic activity. Improvements in enzyme activity can be from about 1.5 times the enzymatic activity of the corresponding wild-type ketoreductase enzyme, to as much as 2 times. 5 times, 10 times, 20 times, 25 times, 50 times, 75 times, 100 times, or more enzymatic activity than the naturally occurring ketoreductase or another engineered ketoreductase from which the ketoreductase polypeptides were derived. In specific embodiments, the engineered ketoreductase enzyme exhibits improved enzymatic activity in the range of 1.5 to 50 times, 1.5 to 100 times greater than that of the parent ketoreductase enzyme. It is understood by the skilled artisan that the activity of any enzyme is diffusion limited such that the catalytic turnover rate cannot exceed the diffusion rate of the substrate, including any required cofactors. The theoretical maximum of the diffusion limit, or $k_{cat}/K_m$, is generally about $10^8$ to $10^9$ $(M^{-1}s^{-1})$. Hence, any improvements in the enzyme activity of the ketoreductase will have an upper limit related to the diffusion rate of the substrates acted on by the ketoreductase enzyme. Ketoreductase activity can be measured by any one of standard assays used for measuring ketoreductase, such as a decrease in absorbance or fluorescence of NADPH (see Example 6) due to its oxidation with the concomitant reduction of a ketone to an alcohol, or by product produced in a coupled assay. Comparisons of enzyme activities are made using a defined preparation of enzyme, a defined assay under a set condition, and one or more defined substrates, as further described in detail herein. Generally, when lysates are compared, the numbers of cells and the amount of protein assayed are determined as well as use of identical expression systems and identical host cells to minimize variations in amount of enzyme produced by the host cells and present in the lysates.

"Conversion" refers to the enzymatic reduction of the substrate to the corresponding product. "Percent conversion" refers to the percent of the substrate that is reduced to the product within a period of time under specified conditions. Thus, the "enzymatic activity" or "activity" of a ketoreductase polypeptide can be expressed as "percent conversion" of the substrate to the product.

"Thermostable" refers to a ketoreductase polypeptide that maintains similar activity (e.g., more than 60% to 80% for example) after exposure to elevated temperatures (e.g., 40-80° C.) for a period of time (e.g., 0.5-24 hrs) compared to the untreated enzyme.

"Solvent stable" refers to a ketoreductase polypeptide that maintains similar activity (e.g., more than 60% to 80%) after exposure to varying concentrations (e.g., 5-99%) of solvent (e.g. isopropylalcohol, tetrahydrofuran, 2-methyltetrahydrofuran, acetone, toluene, butylacetate, methyl tert-butylether, etc.) for a period of time (e.g., 0.5-24 hrs) compared to the untreated enzyme.

"pH stable" refers to a ketoreductase polypeptide that maintains similar activity (e.g., more than 60% to 80%) after exposure to high or low pH (e.g., 4.5-6 or 8 to 12) for a period of time (e.g., 0.5-24 hrs) compared to the untreated enzyme.

"Thermo- and solvent stable" refers to a ketoreductase polypeptide that is both thermostable and solvent stable.

"Derived from" as used herein in the context of engineered ketoreductase enzymes, identifies the originating ketoreductase enzyme, and/or the gene encoding such ketoreductase enzyme, upon which the engineering was based. For example, the engineered ketoreductase enzyme of SEQ ID NO:24 was obtained by artificially evolving, over multiple generations the gene encoding the *Lactobacillus kefir* ketoreductase enzyme of SEQ ID NO:4. Thus, this engineered ketoreductase enzyme is "derived from" the wild-type ketoreductase of SEQ ID NO:4.

"Hydrophilic Amino Acid or Residue" refers to an amino acid or residue having a side chain exhibiting a hydrophobicity of less than zero according to the normalized consensus hydrophobicity scale of Eisenberg et al., 1984, *J. Mol. Biol.* 179:125-142. Genetically encoded hydrophilic amino acids include L-Thr (T), L-Ser (S), L-His (H), L-Glu (E), L-Asn (N), L-Gln (O), L-Asp (D), L-Lys (K) and L-Arg (R).

"Acidic Amino Acid or Residue" refers to a hydrophilic amino acid or residue having a side chain exhibiting a pK value of less than about 6 when the amino acid is included in a peptide or polypeptide. Acidic amino acids typically have negatively charged side chains at physiological pH due to loss of a hydrogen ion. Genetically encoded acidic amino acids include L-Glu (E) and L-Asp (D).

"Basic Amino Acid or Residue" refers to a hydrophilic amino acid or residue having a side chain exhibiting a pK value of greater than about 6 when the amino acid is included in a peptide or polypeptide. Basic amino acids typically have positively charged side chains at physiological pH due to association with hydronium ion. Genetically encoded basic amino acids include L-Arg (R) and L-Lys (K).

"Polar Amino Acid or Residue" refers to a hydrophilic amino acid or residue having a side chain that is uncharged at physiological pH, but which has at least one bond in which the pair of electrons shared in common by two atoms is held more closely by one of the atoms. Genetically encoded polar amino acids include L-Asn (N), L-Gln (O), L-Ser (S) and L-Thr (T).

"Hydrophobic Amino Acid or Residue" refers to an amino acid or residue having a side chain exhibiting a hydrophobicity of greater than zero according to the normalized consensus hydrophobicity scale of Eisenberg et al., 1984, *J. Mol. Biol.* 179:125-142. Genetically encoded hydrophobic amino acids include L-Pro (P), L-Ile (I), L-Phe (F), L-Val (V), L-Leu (L), L-Trp (W), L-Met (M), L-Ala (A) and L-Tyr (Y).

"Aromatic Amino Acid or Residue" refers to a hydrophilic or hydrophobic amino acid or residue having a side chain that includes at least one aromatic or heteroaromatic ring. Genetically encoded aromatic amino acids include L-Phe (F), L-Tyr (Y) and L-Trp (W). Although owing to the pKa of its heteroaromatic nitrogen atom L-His (H) it is sometimes classified as a basic residue, or as an aromatic residue as its side chain includes a heteroaromatic ring, herein histidine is classified as a hydrophilic residue or as a "constrained residue" (see below).

"Constrained amino acid or residue" refers to an amino acid or residue that has a constrained geometry. Herein, constrained residues include L-pro (P) and L-his (H). Histidine has a constrained geometry because it has a relatively small imidazole ring. Proline has a constrained geometry because it also has a five membered ring.

"Non-polar Amino Acid or Residue" refers to a hydrophobic amino acid or residue having a side chain that is uncharged at physiological pH and which has bonds in which the pair of electrons shared in common by two atoms is generally held equally by each of the two atoms (i.e., the side chain is not polar). Genetically encoded non-polar amino acids include L-Gly (G), L-Leu (L), L-Val (V), L-Ile (I), L-Met (M) and L-Ala (A).

"Aliphatic Amino Acid or Residue" refers to a hydrophobic amino acid or residue having an aliphatic hydrocarbon side chain. Genetically encoded aliphatic amino acids include L-Ala (A), L-Val (V), L-Leu (L) and L-Ile (I).

"Cysteine". The amino acid L-Cys (C) is unusual in that it can form disulfide bridges with other L-Cys (C) amino acids or other sulfanyl- or sulfhydryl-containing amino acids. The "cysteine-like residues" include cysteine and other amino acids that contain sulfhydryl moieties that are available for formation of disulfide bridges. The ability of L-Cys (C) (and other amino acids with —SH containing side chains) to exist in a peptide in either the reduced free —SH or oxidized disulfide-bridged form affects whether L-Cys (C) contributes net hydrophobic or hydrophilic character to a peptide. While L-Cys (C) exhibits a hydrophobicity of 0.29 according to the normalized consensus scale of Eisenberg (Eisenberg et al., 1984, supra), it is to be understood that for purposes of the present disclosure L-Cys (C) is categorized into its own unique group.

"Small Amino Acid or Residue" refers to an amino acid or residue having a side chain that is composed of a total three or fewer carbon and/or heteroatoms (excluding the α-carbon and hydrogens). The small amino acids or residues may be further categorized as aliphatic, non-polar, polar or acidic small amino acids or residues, in accordance with the above definitions. Genetically-encoded small amino acids include L-Ala (A), L-Val (V), L-Cys (C), L-Asn (N), L-Ser (S), L-Thr (T) and L-Asp (D).

"Hydroxyl-containing Amino Acid or Residue" refers to an amino acid containing a hydroxyl (—OH) moiety. Genetically-encoded hydroxyl-containing amino acids include L-Ser (S) L-Thr (T) and L-Tyr (Y).

"Conservative" amino acid substitutions or mutations refer to the interchangeability of residues having similar side chains, and thus typically involves substitution of the amino acid in the polypeptide with amino acids within the same or similar defined class of amino acids. However, as used herein, in some embodiments, conservative mutations do not include substitutions from a hydrophilic to hydrophilic, hydrophobic to hydrophobic, hydroxyl-containing to hydroxyl-containing, or small to small residue, if the conservative mutation can instead be a substitution from an aliphatic to an aliphatic, non-polar to non-polar, polar to polar, acidic to acidic, basic to basic, aromatic to aromatic, or constrained to constrained residue. Further, as used herein, A, V, L, or I can be conservatively mutated to either another aliphatic residue or to another non-polar residue. Table 1 below shows exemplary conservative substitutions.

TABLE 1

Exemplary Conservative Mutations

| Residue | Exemplary Conservative Mutations |
| --- | --- |
| A, L, V, I | Other aliphatic (A, L, V, I) |
|  | Other non-polar (A, L, V, I, G, M) |
| G, M | Other non-polar (A, L, V, I, G, M) |
| D, E | Other acidic (D, E) |
| K, R | Other basic (K, R) |
| P, H | Other constrained (P, H) |
| N, Q, S, T | Other polar |
| Y, W, F | Other aromatic (Y, W, F) |
| C | None |

"Non-conservative substitution" refers to substitution or mutation of an amino acid in the polypeptide with an amino acid with significantly differing side chain properties. Non-conservative substitutions may use amino acids between, rather than within, the defined groups listed above. In one embodiment, a non-conservative mutation affects (a) the structure of the peptide backbone in the area of the substitution (e.g. proline for glycine) (b) the charge or hydrophobicity, or (c) the bulk of the side chain.

"Deletion" refers to modification to the polypeptide by removal of one or more amino acids from the reference polypeptide. Deletions can comprise removal of 1 or more amino acids, 2 or more amino acids, 3 or more amino acids, 4 or more amino acids, 5 or more amino acids, 6 or more amino acids, 7 or more amino acids, 8 or more amino acids, 10 or more amino acids, 12 or more amino acids, 15 or more amino acids, or 20 or more amino acids, up to 10% of the total number of amino acids, or up to 20% of the total number of amino acids making up the reference enzyme while retaining enzymatic activity and/or retaining the improved properties of an engineered ketoreductase enzyme. Deletions can be directed to the internal portions and/or terminal portions of the polypeptide. In various embodiments, the deletion can comprise a continuous segment or can be discontinuous.

"Insertion" refers to modification to the polypeptide by addition of one or more amino acids from the reference polypeptide. In some embodiments, the improved engineered ketoreductase enzymes comprise insertions of one or more amino acids to the naturally occurring ketoreductase polypeptide as well as insertions of one or more amino acids to other improved ketoreductase polypeptides. Insertions can be in the internal portions of the polypeptide, or to the carboxy or amino terminus. Insertions as used herein include fusion proteins as is known in the art. The insertion can be a contiguous segment of amino acids or separated by one or more of the amino acids in the naturally occurring polypeptide.

"Fragment" as used herein refers to a polypeptide that has an amino-terminal and/or carboxy-terminal deletion, but where the remaining amino acid sequence is identical to the corresponding positions in the sequence. Fragments can be at least 14 amino acids long, at least 20 amino acids long, at least 50 amino acids long or longer, and up to 70%, 80%, 90%, 95%, 98%, and 99% of a full-length ketoreductase polypeptide (e.g., the length of a naturally occurring ketoreductase).

"Isolated polypeptide" refers to a polypeptide which is substantially separated from other contaminants that naturally accompany it, e.g., protein, lipids, and polynucleotides. The term embraces polypeptides which have been removed or purified from their naturally-occurring environment or expression system (e.g., host cell or in vitro synthesis). The improved ketoreductase enzymes may be present within a cell, present in the cellular medium, or prepared in various forms, such as lysates or isolated preparations. As such, in some embodiments, the improved ketoreductase enzyme can be an isolated polypeptide.

"Substantially pure polypeptide" refers to a composition in which the polypeptide species is the predominant species present (i.e., on a molar or weight basis it is more abundant than any other individual macromolecular species in the composition), and is generally a substantially purified composition when the object species comprises at least about 50 percent of the macromolecular species present by mole or % weight. Generally, a substantially pure ketoreductase composition will comprise about 60% or more, about 70% or more, about 80% or more, about 90% or more, about 95% or more, and about 98% or more of all macromolecular species by mole or % weight present in the composition. In some embodiments, the object species is purified to essential homogeneity (i.e., contaminant species cannot be detected in the composition by conventional detection methods) wherein the composition consists essentially of a single macromolecular species. Solvent species, small molecules (<500 Daltons), and elemental ion species are not considered macromolecular species. In some embodiments, the isolated improved ketoreductases polypeptide is a substantially pure polypeptide composition.

"Stringent hybridization" is used herein to refer to conditions under which nucleic acid hybrids are stable. As known to those of skill in the art, the stability of hybrids is reflected in the melting temperature ($T_m$) of the hybrids. In general, the stability of a hybrid is a function of ion strength, temperature, G/C content, and the presence of chaotropic agents. The $T_m$ values for polynucleotides can be calculated using known methods for predicting melting temperatures (see, e.g., Baldino et al., *Methods Enzymology* 168:761-777; Bolton et al., 1962, *Proc. Natl. Acad. Sci. USA* 48:1390; Bresslauer et al., 1986, *Proc. Natl. Acad. Sci. USA* 83:8893-8897; Freier et al., 1986, *Proc. Natl. Acad. Sci. USA* 83:9373-9377; Kierzek et al., *Biochemistry* 25:7840-7846; Rychlik et al., 1990, *Nucleic Acids Res* 18:6409-6412 (erratum, 1991, *Nucleic Acids Res* 19:698); Sambrook et al., supra); Suggs et al., 1981, In *Developmental Biology Using Purified Genes* (Brown et al., eds.), pp. 683-693, Academic Press; and Wetmur, 1991, *Crit. Rev Biochem Mol Biol* 26:227-259. All publications incorporate herein by reference). In some embodiments, the polynucleotide encodes the polypeptide disclosed herein and hybridizes under defined conditions, such as moderately stringent or highly stringent conditions, to the complement of a sequence encoding an engineered ketoreductase enzyme of the present disclosure.

"Hybridization stringency" relates to hybridization conditions, such as washing conditions, in the hybridization of nucleic acids. Generally, hybridization reactions are performed under conditions of lower stringency, followed by washes of varying but higher stringency. The term "moderately stringent hybridization" refers to conditions that permit target-DNA to bind a complementary nucleic acid that has about 60% identity, preferably about 75% identity, about 85% identity to the target DNA with greater than about 90% identity to target-polynucleotide. Exemplary moderately stringent conditions are conditions equivalent to hybridization in 50% formamide, 5×Denhart's solution, 5×SSPE, 0.2% SDS at 42° C., followed by washing in 0.2×SSPE, 0.2% SDS, at 42° C. "High stringency hybridization" refers generally to conditions that are about 10° C. or less from the thermal melting temperature $T_m$ as determined under the solution condition for a defined polynucleotide sequence. In some embodiments, a high stringency condition refers to conditions that permit hybridization of only those nucleic acid sequences that form stable hybrids in 0.018M NaCl at 65° C. (i.e., if a hybrid is not stable in 0.018M NaCl at 65° C., it will not be stable under high stringency conditions, as contemplated herein). High stringency conditions can be provided, for example, by hybridization in conditions equivalent to 50% formamide, 5×Denhart's solution, 5×SSPE, 0.2% SDS at 42° C., followed by washing in 0.1×SSPE, and 0.1% SDS at 65° C. Other high stringency hybridization conditions, as well as moderately stringent conditions, are described in the references cited above.

"Heterologous" polynucleotide refers to any polynucleotide that is introduced into a host cell by laboratory techniques, and includes polynucleotides that are removed from a host cell, subjected to laboratory manipulation, and then reintroduced into a host cell.

"Codon optimized" refers to changes in the codons of the polynucleotide encoding a protein to those preferentially used in a particular organism such that the encoded protein is efficiently expressed in the organism of interest. Although the genetic code is degenerate in that most amino acids are represented by several codons, called "synonyms" or "synonymous" codons, it is well known that codon usage by particular organisms is nonrandom and biased towards particular codon triplets. This codon usage bias may be higher in reference to a given gene, genes of common function or ancestral origin, highly expressed proteins versus low copy number proteins, and the aggregate protein coding regions of an organism's genome. In some embodiments, the polynucleotides encoding the ketoreductases enzymes may be codon optimized for optimal production from the host organism selected for expression.

"Preferred, optimal, high codon usage bias codons" refers interchangeably to codons that are used at higher frequency in the protein coding regions than other codons that code for the same amino acid. The preferred codons may be determined in relation to codon usage in a single gene, a set of genes of common function or origin, highly expressed genes, the codon frequency in the aggregate protein coding regions of the whole organism, codon frequency in the aggregate protein coding regions of related organisms, or combinations thereof. Codons whose frequency increases with the level of gene expression are typically optimal codons for expression. A variety of methods are known for determining the codon frequency (e.g., codon usage, relative synonymous codon usage) and codon preference in specific organisms, including multivariat analysis, for example, using cluster analysis or correspondence analysis, and the effective number of codons used in a gene (see GCG CodonPreference, Genetics Computer Group Wisconsin Package; CodonW, John Peden, University of Nottingham; McInerney, J. O, 1998, Bioinformatics 14:372-73; Stenico et al., 1994, *Nucleic Acids Res.* 222437-46; Wright, F., 1990, *Gene* 87:23-29). Codon usage tables are available for a growing list of organisms (see for example, Wada et al., 1992, *Nucleic Acids Res.* 20:2111-2118; Nakamura et al., 2000, *Nucl. Acids Res.* 28:292; Duret et al., supra; Henaut and Danchin, "*Escherichia coli* and *Salmonella*," 1996, Neidhardt et al. Eds., ASM Press, Washington D.C., p. 2047-2066). The data source for obtaining codon usage may rely on any available nucleotide sequence capable of coding for a protein. These data sets include nucleic acid sequences actually known to encode expressed proteins (e.g., complete protein coding sequences-CDS), expressed sequence tags (ESTS), or predicted coding regions of genomic sequences (see for example, Mount, D., *Bioinformatics: Sequence and Genome Analysis*, Chapter 8, Cold Spring Harbor Laboratory Press, Cold Spring Harbor, N.Y., 2001; Uberbacher, E. C., 1996, *Methods Enzymol.* 266:259-281; Tiwari et al., 1997, *Comput. Appl. Biosci.* 13:263-270).

"Control sequence" is defined herein to include all components, which are necessary or advantageous for the expression of a polypeptide of the present disclosure. Each control sequence may be native or foreign to the nucleic acid sequence encoding the polypeptide. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the nucleic acid sequence encoding a polypeptide.

"Operably linked" is defined herein as a configuration in which a control sequence is appropriately placed at a position relative to the coding sequence of the DNA sequence such that the control sequence directs the expression of a polynucleotide and/or polypeptide.

"Promoter sequence" is a nucleic acid sequence that is recognized by a host cell for expression of the coding region. The control sequence may comprise an appropriate promoter sequence. The promoter sequence contains transcriptional control sequences, which mediate the expression of the polypeptide. The promoter may be any nucleic acid sequence which shows transcriptional activity in the host cell of choice including mutant, truncated, and hybrid promoters, and may be obtained from genes encoding extracellular or intracellular polypeptides either homologous or heterologous to the host cell.

"Cofactor regeneration system" refers to a set of reactants that participate in a reaction that reduces the oxidized form of the cofactor (e.g., NADP+ to NADPH). Cofactors oxidized by the ketoreductase-catalyzed reduction of the keto substrate are regenerated in reduced form by the cofactor regeneration system. Cofactor regeneration systems comprise a stoichiometric reductant that is a source of reducing hydrogen equivalents and is capable of reducing the oxidized form of the cofactor. The cofactor regeneration system may further comprise a catalyst, for example an enzyme catalyst that catalyzes the reduction of the oxidized form of the cofactor by the reductant. Cofactor regeneration systems to regenerate NADH or NADPH from NAD+ or NADP+, respectively, are known in the art and may be used in the methods described herein.

7.2 Ketoreductase Enzymes

The present disclosure provides engineered ketoreductase ("KRED") enzymes that are capable of stereospecifically reducing (R)-2-methylpentanal ("the substrate"), such as in a racemic mixture of (R)-2-methylpentanal and (S) 2-methylpentanal (the "racemic substrate" or "racemic substrate mixture"), to (R)-2-methylpentanol ("the product"), and having an improved property when compared with a naturally-occurring, wild-type KRED enzyme obtained from *L. kefir* (SEQ ID NO:4), *L. brevis* (SEQ ID NO:2), or *L. minor* (SEQ ID NO:48), or when compared with another engineered ketoreductase enzyme. Enzyme properties for which improvement is desirable include, but are not limited to, enzymatic activity, thermal stability, pH activity profile, cofactor requirements, refractoriness to inhibitors (e.g., product inhibition), sterospecificity, stereoselectivity, and solvent stability. The improvements can relate to a single enzyme property, such as enzymatic activity, or a combination of different enzyme properties, such as enzymatic activity and stereospecificity.

For the ketoreductase polypeptides described herein, the amino acid sequence of the ketoreductases have the requirement that the residue corresponding to X145 of SEQ ID NO:2, 4 or 48 is a polar residue and the residue corresponding to X153 of SEQ ID NO:2, 4 or 48 is a polar residue. In some embodiments, the amino acid sequence of the ketoreductases have the requirement that the residue corresponding to X145 of SEQ ID NO:2, 4 or 48 is a serine and the residue corresponding to X153 of SEQ ID NO:2, 4 or 48 is a glutamine. In some embodiments, the residue corresponding to X153 is a polar amino acid and the residue corresponding to X145 is not serine. In some embodiments, the residue corresponding to X153 is a glutamine and the residue corresponding to X145 is not serine.

In some embodiments, as noted above, the engineered ketoreductase with improved enzyme property is described with reference to *Lactobacillus kefir* ketoreductase of SEQ ID NO:4, *Lactobacillus brevis* ketoreductase of SEQ ID NO:2, *Lactobacillus minor* ketoreductase of SEQ ID NO:48, or another engineered ketoreductase, such as SEQ ID NO:6. The amino acid residue position is determined in these ketoreductases beginning from the initiating methionine (M) residue (i.e., M represents residue position 1), although it will be understood by the skilled artisan that this initiating methionine residue may be removed by biological processing machinery, such as in a host cell or in vitro translation system, to generate a mature protein lacking the initiating methionine residue. The amino acid residue position at which a particular amino acid or amino acid change is present in an amino acid sequence is sometimes describe herein in terms "Xn", or "residue n", where n refers to the residue position. Where the amino acid residues at the same residue position differ between the ketoreductases, the different residues are denoted by a "/" with the arrangement being, for example, "kefir residue/brevis residue/minor." A substitution mutation, which is a replacement of an amino acid residue in a residue corresponding to a residue of a reference sequence, for example the naturally occurring ketoreductases of SEQ ID NO:2, SEQ ID NO:4, or SEQ ID NO:48, with a different amino acid residue is denoted by the symbol "→".

Herein, mutations are sometimes described as a mutation of a residue "to a" type of amino acid. For example, SEQ ID NO:4, residue 72 (lysine) can be mutated "to a" polar residue. But the use of the phrase "to a" does not exclude mutations from one amino acid of a class to another amino acid of the same class. For example, residue 72 can be mutated from a lysine "to an" arginine.

The naturally occurring polynucleotide encoding the naturally occurring ketoreductase of *Lactobacillus kefir*, *Lactobacillus brevis*, or *Lactobacillus minor* (also referred to as "ADH" or "alcohol dehydrogenase") can be obtained from the isolated polynucleotide known to encode the ketoreductase activity (e.g., Genbank accession no. AAP94029 GI:33112056 or SEQ ID NO:3 for *Lactobacillus kefir*, Genbank accession no. CAD66648 GI:28400789 or SEQ ID NO:1 for *Lactobacillus brevis*, and U.S. Pat. Appl. No. 20040265978 or SEQ ID NO:47 for *Lactobacillus minor*).

In some embodiments, the ketoreductase polypeptides herein can have a number of modifications to the reference sequence (e.g., an engineered ketoreductase polypeptide) to result in an improved ketoreductase enzyme property. In such embodiments, the number of modifications to the amino acid sequence can comprise one or more amino acids, 2 or more amino acids, 3 or more amino acids, 4 or more amino acids, 5 or more amino acids, 6 or more amino acids, 8 or more amino acids, 9 or more amino acids, 10 or more amino acids, 15 or more amino acids, or 20 or more amino acids, up to 10% of the total number of amino acids, up to 10% of the total number of amino acids, up to 20% of the total number of amino acids, or up to 30% of the total number of amino acids of the reference enzyme sequence. In some embodiments, the number of modifications to the naturally occurring polypeptide or an engineered polypeptide that produces an improved ketoreductase property may comprise from about 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-25, 1-30, 1-35 or about 1-40 modifications of the reference sequence. The modifications can comprise insertions, deletions, substitutions, or combinations thereof.

In some embodiments, the modifications comprise amino acid substitutions to the reference sequence. Substitutions that can produce an improved ketoreductase property may be at one or more amino acids, 2 or more amino acids, 3 or more amino acids, 4 or more amino acids, 5 or more amino acids, 6 or more amino acids, 7 or more amino acids, 8 or more amino acids, 9 or more amino acids, 10 or more amino acids, 15 or more amino acids, or 20 or more amino acids, up to 10% of the total number of amino acids, up to 15% of the total number of amino acids, up to 20% of the total number of amino acids, or up to 30% of the total number of amino acids of the reference enzyme sequence. In some embodiments, the number of substitutions to the naturally occurring polypeptide or an engineered polypeptide that produces an improved ketoreductase property can comprise from about 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-25, 1-30, 1-35 or about 1-40 amino acid substitutions of the reference sequence.

In some embodiments, the improved property (as compared to wild-type or another engineered polypeptide) of the ketoreductase polypeptide is with respect to an increase of its stereospecificity, i.e., herein, the ability of the enzyme to differentiate the two enantiomers of 2-methylpentanal ("the substrate"), generally in a non-chirally pure 2-methylpentanal (e.g., in a racemic mixture), and preferentially reduce the (R) enantiomer to (R)-2-methylpentanol ("the product"). This improvement in this property of the ketoreductase polypeptide can be expressed as an improvement in the "E-value" for the reaction with the ketoreductase. In some embodiments, the improved property of the ketoreductase polypeptide is with respect to an increase in its ability to convert or reduce a greater percentage of the substrate to the product. In some embodiments, the improved property of the ketoreductase polypeptide is with respect to an increase in its rate of conversion of the substrate to the product. This improvement in enzymatic activity can be manifested by the ability to use less of the improved polypeptide as compared to the wild-type or other reference sequence(s) to reduce or convert the same amount of product. In some embodiments, the improved property of the ketoreductase polypeptide is with respect to its stability or thermostability. In some embodiments, the ketoreductase polypeptide has more than one improved property, such as a combination of stereospecificity, enzyme activity, and thermostability.

In some embodiments, the ketoreductase polypeptide is capable of stereospecifically reducing the (R)-enantiomer of 2-methylpentanal to (R)-2-methylpentanol to give product with a percent stereomeric excess of the (R)-2-methylpentanol of at least about 25%, 50%, 75%, 80%, 85%, 85%, 87%, 88%, 89%, 90%, 91%, 92%, 93%, 94%, 95%, 96%, 97%, 98%, 99%, 99.9%, or 99.99%.

In some embodiments, the ketoreductase polypeptide is capable of stereospecifically reducing the substrate to the product in greater than about 90% stereomeric excess. Exemplary polypeptides with such stereospecificity include, but are not limited to, the polypeptides comprising the amino acid sequences corresponding to SEQ ID NO:6, 8, 10, 12, 14, 16, 18, 20, 22, 24, 26, 28, 30, 32, 34, 36, 38, 40, 42, or 44.

In some embodiments, the ketoreductase polypeptide is capable of stereospecifically reducing the substrate to the product in greater than about 98% stereomeric excess. Exemplary ketoreductase polypeptides with such high stereospecificity include, but are not limited to, the polypeptides comprising the amino acid sequences corresponding to SEQ ID NO:24, 26, 28, or 44.

In some embodiments, the ketoreductase polypeptide is capable of stereospecifically reducing the substrate to the product with a percent stereomeric excess that is at least about 98%, 99%, 99.9%, or 99.99%, where the polypeptide comprises an amino acid sequence corresponding to: SEQ ID NO:24, 26, or 28, 44.

In some embodiments, the ketoreductase polypeptide is capable of stereospecifically reducing the substrate to the product with a percent stereomeric excess that is improved as compared to the percent stereomeric excess obtained in a reaction with the L. kefir, L. brevis, L. minor KRED (SEQ ID NO:4, 2, or 48), where the polypeptides comprise amino acid sequences corresponding to SEQ ID NO:6, 8, 10, 12, 14, 16, 18, 20, 22, 24, 26, 28, 30, 32, 34, 36, 38, 40, 42, and 44.

In some embodiments, the ketoreductase polypeptides are improved as compared to wild-type (SEQ ID NO:4) with respect to their rate of enzymatic activity, i.e., their rate or ability of converting the substrate to the product. Exemplary polypeptides that are capable of converting the substrate to the product at a rate that is improved over wild-type, include but are not limited to, polypeptides that comprise the amino acid sequences corresponding to SEQ ID NO:6, 8, 10, 12, 14, 16, 18, 20, 22, 24, 26, 28, 30, 32, 34, 36, 38, 40, 42, and 44.

In some embodiments, the ketoreductase polypeptides of the invention are improved as compared to SEQ ID NO:2 with respect to their rate of enzymatic activity, i.e., their rate of converting the substrate to the product. In some embodiments, the ketoreductase polypeptides are capable of converting the substrate to the product at a rate that is at least 5-fold, 10-fold, 25-fold, 50-fold, 75-fold, 100-fold, 150-fold, 200-fold, 250-fold, or 300-fold over the rate of SEQ ID NO:2. Such sequences, include but are not limited to, those corresponding to SEQ ID NO:6, 8, 10, 12, 14, 16, 18, 20, 22, 24, 26, 28, 30, 32, 34, 36, 38, 40, 42, and 44.

In some embodiments, the ketoreductase polypeptides of the disclosure are capable of reducing the substrate to product with a stereomeric excess of at least about 90, 91, 92, 93, 94, 95, 96, 97, 98%, 99%, 99.9% or 99.99%, and is capable of converting at least about 45%, 46%, 47%, 48%, 49%, 50%, 51%, 52%, 53%, 54%, or 55% of the substrate to the product in less than 24 hours when the reaction is conducted with about 1% or less than about 1% but more than 0% of the ketoreductase polypeptide by weight with respect to the weight of the amount of substrate. Exemplary polypeptides that have this capability include, but are not limited to, polypeptides comprising the sequence that corresponds to SEQ ID NO:6, 8, 10, 12, 14, 16, 18, 20, 22, 24, 26, 28, 30, 32, 34, 36, 38, 40, 42, and 44.

In some embodiments, the ketoreductase polypeptides have improved activity and stability over wild-type, and can reduce the substrate to the product in greater than about 98% e.e. Exemplary polypeptides with such capabilities include, but are not limited to SEQ ID NO:24, 26, 28, or 44.

In some embodiments, the ketoreductase polypeptides of the invention are improved as compared to SEQ ID NO:2 with respect to their thermostability, as determined by an increase in the rate of enzymatic activity over SEQ ID NO:2 under high temperatures. In some embodiments, increased thermostability is associated with a mutation of residue 147 of SEQ ID NO:2, 4 or 48. Exemplary ketoreductase polypeptides with improved stability, include but are not limited to, polypeptides comprising an amino acid sequence corresponding to SEQ ID NO:24, 32, 34, 36, 38, or 40.

Table 2 below provides a list of the SEQ ID NOs disclosed herein with associated enzyme properties, except for the sequence formulas of SEQ ID NO:45, 46, and 57. In Table 2 below, each row lists two SEQ ID NOs, where the odd number refers to the nucleotide sequence that codes for the amino acid sequence provided by the even number. All sequences below are derived from the wild-type L. kefir ketoreductase sequences (SEQ ID NO:4), unless otherwise specified.

TABLE 2

List of Sequences

| SEQ ID NO: | Mutations as Compared to SEQ ID NO: 4 | Stereospecificity ("E-values") | Thermostability |
|---|---|---|---|
| 3/4 | None | + | |
| 5/6 | S96A; T104M; G117S; E145S; A202V | +++ | |
| 7/8 | G117S; E145S; N157T; I223V | ++ | |
| 9/10 | T104M; E145S; A202I | +++ | |
| 11/12 | T104M E145S A202V | +++ | |
| 13/14 | K72E S96A T104M G117S E145S L153Q | +++ | |
| 15/16 | S96K L153Q K236R | +++ | |
| 17/18 | S96Q L153Q K236R | +++ | |
| 19/20 | S96R L153Q K236R | +++ | |
| 21/22 | L153Q K236R | ++ | |
| 23/24 | G82S S96A E145S L153Q | +++++ | + |
| 25/26 | G82S S96A E145S L153Q I223V | ++++ | |
| 27/28 | G82S; S96A; E145S; L153Q; I223V | ++++ | |
| 29/30 | G82S L153Q I223V | ++ | |
| 31/32 | G82S E145S F147M L153Q I223V | ++ | + |
| 33/34 | G82S E145S F147L L153Q I223V | ++ | + |
| 35/36 | G82S E145S F147V L153Q I223V | ++ | + |
| 37/38 | G82S E145S F147V L153Q D178G I223V | ++ | + |
| 39/40 | G82S E145S F147C L153Q I223V | ++ | + |
| 41/42 | G82S E145S L153Q I223V | +++ | |
| 43/44 | K46R G82S E145S L153Q I223V | ++++ | |

In Table 2 above, in the stereospecificity column, "+" indicates an E-value of <50; "++" indicates an E-value of 51 to 100; "+++" indicates an E-value of 101 to 200; "++++" indicates an E-value of 201 to 300; and "+++++" indicates an E-value of ≧301. In the stability column, "+" indicates the polypeptide exhibits improved thermostability as compared to wild-type of SEQ ID NO:4.

In some embodiments, the improved ketoreductase polypeptides herein comprises an amino acid sequence that is at least about 85%, 86%, 87%, 88%, 89%, 90%, 91%, 92%, 93%, 94%, 95%, 96%, 97%, 98%, or 99% identical as compared a reference sequence based on SEQ ID NO:2, 4 or 48 having the features described above for residues X145 and X153. As such, in some embodiments, the ketoreductase polypeptides have at least the following features: residue corresponding to X145 is a polar residue, and residue corresponding to X153 is a polar residue. In some embodiments, the ketoreductase polypeptides have at least the following features: the residue corresponding to X145 is a serine, and the residue corresponding to X153 is a glutamine. In some embodiments, the ketoreductase polypeptides have at least the following features: the residue corresponding to X153 is a polar residue and the residue corresponding to X145 is not a polar residue. In some embodiments, the ketoreductase polypeptides have at least the following features: the residue corresponding to X153 is a glutamine and the residue corresponding to X145 is not serine. In some embodiments, the ketoreductase polypeptides with the specified amino acids at residue X145 and/or residue X153 can have one or more modifications (i.e., residue differences) as compared to the reference amino acid sequence. The modifications can include substitutions, deletions, insertions, or combinations thereof. The substitutions can be non-conservative substitutions, conservative substitutions, or a combination of non-conservative and conservative substitutions. In some embodiments, these ketoreductase polypeptides can have optionally from about 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-25, 1-30, 1-35 or about 1-40 mutations at other amino acid residues. In some embodiments, the number of modifications can be 1, 2, 3, 4, 5, 6, 7, 8, 9, 10, 11, 12, 14, 15, 16, 18, 20, 22, 24, 26, 30, 35 or about 40 other amino acid residues.

In some embodiments, highly stereospecific (herein, capable of reducing the substrate to the product with a stereomeric excess that is at least about 98%) ketoreductase polypeptides comprise a an amino acid sequence that corresponds to the sequence formulas as laid out in SEQ ID NO:45, SEQ ID NO:46, or SEQ ID NO:57, or a region thereof, such as residues 90-211. SEQ ID NO:45 is based on the wild-type amino acid sequence of the *Lactobacillus kefir* ketoreductase (SEQ ID NO:4); SEQ ID NO:46 is based on the wild-type amino acid sequence of the *Lactobacillus brevis* ketoreductase (SEQ ID NO:2); and SEQ ID NO:57 is based on the wild-type amino acid sequence of the *Lactobacillus minor* ketoreductase (SEQ ID NO:48). The sequence formulas of SEQ ID NO:45, 46, and 57 provide that X145 is a polar residue and X153 is a polar residue. In some embodiments, the ketoreductase polypeptide based on the sequence formula of SEQ ID NO:45, 46 or 57 can comprise an amino acid sequence that is at least about 85%, 86%, 87%, 88%, 89%, 90%, 91%, 92%, 93%, 94%, 95%, 96%, 97%, 98%, or 99% identical to a reference amino acid sequence based on SEQ ID NO:2, 4, or 48 having at least the features described herein for amino acid residues corresponding to X145 and X153. In some embodiments, the reference amino acid sequence based on the sequence formulas of SEQ ID NO: 45, 46 or 57 have the following features: the amino acid residue corresponding to X145 is polar residue, and the amino acid residue corresponding to X153 is polar residue, with the proviso that the ketoreductase polypeptides have at least the stated features. In some embodiments, the reference amino acid sequence based on the sequence formulas of SEQ ID NOs:45, 46 or 57 have the following features: the amino acid residue corresponding to X145 is a serine, and the amino acid residue corresponding to X153 is a glutamine, with the proviso that the ketoreductase polypeptides have at least the stated features. In some embodiments, the reference amino acid sequence based on the sequence formulas of SEQ ID NOs:45, 46 or 57 have the following features: the amino acid residue corresponding to X153 is a polar residue, and the amino acid residue corresponding to X145 is not a polar residue, with the proviso that the ketoreductase polypeptides have at least the stated features. In some embodiments, the reference amino acid sequence based on the sequence formulas of SEQ ID NO: 45, 46 or 57 have the following features: the amino acid residue corresponding to X153 is a glutamine, and the amino acid residue corresponding to X145 is not serine, with the proviso that the ketoreductase polypeptides also have at least the stated features. In some embodiments, the ketoreductases of the disclosure are subject to the proviso that ketoreductases do not include the specific sequences corresponding to SEQ ID NO:16 and SEQ ID NO:42.

In some embodiments, the improved ketoreductase polypeptides comprising an amino acid sequence based on the sequence formula of SEQ ID NO:45, 46 or 57, or region thereof, such as residues 90-211, having the specified features of residues X145 and/or X153 as described herein, can further include one or more of the features selected from the following: residue corresponding to X96 is an aliphatic, basic, nonpolar or polar residue, and residue corresponding to X82 is a polar residue, with the provisos that: (1) the residue corresponding to X96 is not serine when X82 is glycine, and (2) specifically excluded are polypeptides with amino acid sequences of SEQ ID NO:16 and SEQ ID NO:42.

In some embodiments, the improved ketoreductase polypeptide comprising an amino acid sequence based on the sequence formula of SEQ ID NO:45, 46 or 57, or region thereof, such as residues 90-211, having the specified features of residues X145 and/or X153 as described herein, can further include one or more of the following features: residue corresponding to X46 is a basic residue; residue corresponding to X72 is an acidic residue; residue corresponding to X82 is a non-polar or polar residue; residue corresponding to X96 is an aliphatic, basic, non-polar or polar residue; residue corresponding to X104 is a non-polar or polar residue; residue corresponding to X117 is a non-polar or polar residue; residue corresponding to X147 is an aliphatic, cysteine, or nonpolar residue; residue corresponding to X157 is a polar residue; residue corresponding to X177 is an acidic or basic residue; residue corresponding to X178 is a non-polar residue; residue corresponding to X194 is an aliphatic, constrained, or non-polar residue; residue corresponding to X195 is an aliphatic, basic, or non-polar residue; residue corresponding to X202 is an aliphatic, basic, or non-polar residue; residue corresponding to X223 is an aliphatic or non-polar residue; residue corresponding to X236 is a basic residue. In some embodiments, the polypeptides comprising an amino acid sequence based on the sequence formulas of SEQ ID NO:45, 46, or 57 (or region thereof) can optionally have one or more of the residues not specified in the forgoing to be mutated. In some embodiments, the mutations can be from about 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-26, 1-30, 1-35 or about 1-40 mutations at other amino acid residues not defined by X above. In some embodiments, the number of mutations can be 1, 2, 3, 4, 5, 6, 7, 8, 9, 10, 11, 12, 14, 15, 16, 18, 20, 22, 24, 26, 30, 35 or about 40 other amino acid residues. In some embodiments, the mutations comprise conservative mutations.

In some embodiments, the ketoreductase polypeptide comprising an amino acid sequence based on the sequence formula of SEQ ID NO:45, 46 or 57 can have one or more conservative mutations as compared to the amino acid sequence of SEQ ID NO:4, 2, or 48. Exemplary conservatively mutations include amino acid replacements such as, but not limited to: replacement of residue corresponding to X46 (K) with another basic residue, e.g., arginine; replacement of residue corresponding to X96 (S) with another polar residue, e.g., glutamine; replacement of residue corresponding to X147 (F) with another nonpolar residue, e.g., methionine, leucine, valine, or cysteine; replacement of residue X157 (N) with another polar residue, e.g., threonine; replacement of residue corresponding to X202 (A) with another aliphatic residue, e.g., valine or isoleucine; replacement of residue corresponding to X223 (I) with another aliphatic residue, e.g., valine; and replacement of residue corresponding to X236 (K) with another basic residue, e.g., arginine.

In some embodiments, the improved ketoreductase polypeptide comprising an amino acid sequence based on the sequence formula of SEQ ID NO:45, 46 or 57, or region thereof, such as residues 90-211, having the specified features at residues X145 and/or X153 as described herein, can further include one or more of the following features: residue corresponding to X46 is arginine or lysine, particularly arginine; residue corresponding to X72 is aspartic acid or glutamic acid, particularly glutamic acid; residue corresponding to X82 is glycine, methionine, alanine, valine, leucine, isoleucine, asparagine, glutamine, serine or threonine, particularly serine; residue corresponding to X96 is asparagine, glutamine, serine, threonine, lysine, arginine, methionine, glycine, alanine, valine, leucine, isoleucine, particularly alanine, arginine, glutamine, or glycine; residue corresponding to X104 is serine, threonine, glycine, methionine, alanine, valine, leucine, isoleucine, particularly methionine; residue corresponding to X117 is asparagine, glutamine, serine or threonine, particularly serine; residue corresponding to X147 is cysteine, glycine, methionine, alanine, valine, leucine, isoleucine, particularly leucine, methionine or valine; residue corresponding to X157 is asparagine, glutamine, serine or threonine, particularly threonine; residue corresponding to X177 is lysine, arginine, aspartic acid or glutamic acid, particularly glutamic acid; residue corresponding to X178 is glycine, methionine, alanine, valine, leucine, isoleucine, particularly glycine; residue corresponding to X194 is proline, histidine, methionine, glycine, alanine, valine, leucine, or isoleucine, particularly leucine; residue corresponding to X195 is lysine, arginine, glycine, methionine, alanine, valine, leucine, or isoleucine, particularly arginine; residue corresponding to X202 is lysine, arginine, glycine, methionine, alanine, valine, leucine, isoleucine, particularly arginine, isoleucine or valine; residue corresponding to X223 is glycine, methionine, alanine, valine, leucine, isoleucine, particularly valine; and residue corresponding to X236 is lysine or arginine, particularly arginine. In some embodiments, the polypeptides comprising an amino acid sequence based on the sequence formulas of SEQ ID NO:45, 46, or 57 (or region thereof) can optionally have one or more of the residues not specified in the forgoing to be mutated. In some embodiments, the mutations can be from about 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-26, 1-30, 1-35 or about 1-40 mutations at other amino acid residues not defined by X above. In some embodiments, the number of mutations can be 1, 2, 3, 4, 5, 6, 7, 8, 9, 10, 11, 12, 14, 15, 16, 18, 20, 22, 24, 26, 30, 35 or about 40 mutations at other amino acid residues. In some embodiments, the mutations comprise conservative mutations.

In some embodiments, the improved ketoreductase polypeptide comprising an amino acid sequence based on the sequence formula of SEQ ID NO:45, 46 or 57, or region thereof, such as residues 90-211, having the specified features at residues X145 and/or X153 as described herein, can further include one or more of the following features: residue corresponding to X72 is an acidic residue; residue corresponding to X82 is a polar residue; residue corresponding to X96 is a basic, aliphatic or nonpolar residue; residue corresponding to X117 is a polar residue; residue corresponding to X147 is a cysteine, nonpolar, or aliphatic residue; and residue corresponding to X178 is a nonpolar residue. In some embodiments, these polypeptides comprising an amino acid sequence based on the sequence formula of SEQ ID NO:45, 46, or 57 (or region thereof) can optionally have one or more of the residues not specified in the forgoing to be conservatively mutated. In some embodiments, the polypeptides comprising an amino acid sequence based on the sequence formulas of SEQ ID NO:45, 46, or 57 (or region thereof) can optionally have one or more of the residues not specified in the forgoing to be mutated. In some embodiments, the mutations can be from about 1-2, 1-3, 1-4, 1-5, 1-6,1-7, 1-8, 1-9, 1-10, 1-11, 1-12, 1-14, 1-15, 1-16, 1-18, 1-20, 1-22, 1-24, 1-26, 1-30, 1-35 or about 1-40 mutations at other amino acid residues not defined by X above. In some embodiments, the number of mutations can be 1, 2, 3, 4, 5, 6, 7, 8, 9, 10, 11, 12, 14, 15, 16, 18, 20, 22, 24, 26, 30, 35 or about 40 other amino acid residues. In some embodiments, the mutations comprise conservative mutations.

In some embodiments, the improved ketoreductase polypeptide comprising an amino acid sequence based on the sequence formula of SEQ ID NO:45, 46 or 57, or region thereof, such as residues 90-211, having the specified features at residues X145 and/or X153 as described herein, can further include one or more of the following features: residue corresponding to X72 is aspartic acid or glutamic acid, particularly glutamic acid; residue corresponding to X82 is asparagine, glutamine, serine, or threonine, particularly serine; residue corresponding to X96 is lysine, arginine, glycine, leucine, valine, isoleucine, methionine, or alanine, particularly arginine, lysine, or alanine; residue corresponding to X117 is asparagine, glutamine, serine, threonine, particularly serine; residue corresponding to X147 is cysteine, glycine, methionine, alanine, leucine, valine, or isoleucine, particularly cysteine, methionine, leucine or valine; and residue corresponding to X178 is glycine, leucine, valine, isoleucine, methionine, or alanine, particularly glycine. In some embodiments, the polypeptides comprising an amino acid sequence based on the sequence formulas of SEQ ID NO:45, 46, or 57 (or region thereof) can optionally have one or more of the residues not specified in the forgoing to be conservatively mutated. In some embodiments, the polypeptides comprising an amino acid sequence based on the sequence formulas of SEQ ID NO:45, 46, or 57 (or region thereof) can optionally have one or more of the residues not specified in the forgoing to be mutated. In some embodiments, the mutations can be 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-26, 1-30, 1-35 or about 1-40 mutations at other amino acid residues not defined by X above. In some embodiments, the number of mutations can be 1, 2, 3, 4, 5, 6, 7, 8, 9, 10, 11, 12, 14, 15, 16, 18, 20, 22, 24, 26, 30, 35 or about 40 other amino acid residues. In some embodiments, the mutations comprise conservative mutations.

In some embodiments, the improved ketoreductase polypeptide comprising an amino acid sequence based on the sequence formula of SEQ ID NO:45, 46 or 57, or region thereof, such as residues 90-211, having the specified features at residues X145 and/or X153 as described herein, can further include at least the following feature: residue corresponding to X46 is a basic residue, particularly arginine. In some embodiments, the ketoreductase polypeptide comprises an amino acid sequence with at least the preceding features, and wherein the amino acid sequence has at least 85%, 86%, 87%, 88%, 89%, 90%, 91%, 92%, 93%, 94%, 95%, 96%, 97%, 98%, or 99% identity as compared to a reference sequence based on SEQ ID NO:2, 4 or 48 with the preceding features. In some embodiments, the ketoreductase polypeptides can have additionally 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-26, 1-30, 1-35 or about 1-40 residue differences at other amino acid residues as compared to the reference sequence. In some embodiments, the number of differences can be 1, 2, 3, 4, 5, 6, 7, 8, 9, 10, 11, 12, 14, 15, 16, 18, 20, 22, 24, 26, 30, 35 or about 40 residue differences at other amino acid residues. In some embodiments, the differences with the reference sequence comprise conservative mutations.

In some embodiments, the improved ketoreductase polypeptide comprising an amino acid sequence based on the sequence formula of SEQ ID NO:45, 46 or 57, or region thereof, such as residues 90-211, having the specified features at residues X145 and/or X153 as described herein, can further include at least the following features: residue corresponding to X72 is an acidic residue, particularly glutamic acid. In some embodiments, the ketoreductase polypeptide comprises an amino acid sequence with at least the preceding features, and wherein the amino acid sequence has at least 85%, 86%, 87%, 88%, 89%, 90%, 91%, 92%, 93%, 94%, 95%, 96%, 97%, 98%, or 99% identity as compared to a reference sequence based on SEQ ID NO:2, 4 or 48 with the preceding features. In some embodiments, the ketoreductase polypeptides can have additionally 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-26, 1-30, 1-35 or about 1-40 residue differences at other amino acid residues as compared to the reference sequence. In some embodiments, the number of differences can be 1, 2, 3, 4, 5, 6, 7, 8, 9, 10, 11, 12, 14, 15, 16, 18, 20, 22, 24, 26, 30, 35 or about 40 residue differences at other amino acid residues. In some embodiments, the differences with the reference sequence comprise conservative mutations.

In some embodiments, the improved ketoreductase polypeptide comprising an amino acid sequence based on the sequence formula of SEQ ID NO: 45, 46 or 57, or region thereof, such as residues 90-211, having the specified features at residues X145 and/or X153 as described herein, can further include at least the following features: residue corresponding to X82 is a polar residue, particularly serine. In some embodiments, the ketoreductase polypeptide comprises an amino acid sequence with at least the preceding features, and wherein the amino acid sequence has at least 85%, 86%, 87%, 88%, 89%, 90%, 91%, 92%, 93%, 94%, 95%, 96%, 97%, 98%, or 99% identity as compared to a reference sequence based on SEQ ID NO:2, 4 or 48 with the preceding features. In some embodiments, the ketoreductase polypeptides can have additionally 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-26, 1-30, 1-35 or about 1-40 residue differences at other amino acid residues as compared to the reference sequence. In some embodiments, the number of differences can be 1, 2, 3, 4, 5, 6, 7, 8, 9, 10, 11, 12, 14, 15, 16, 18, 20, 22, 24, 26, 30, 35 or about 40 residue differences at other amino acid residues. In some embodiments, the differences with the reference sequence comprise conservative mutations.

In some embodiments, the improved ketoreductase polypeptide comprising an amino acid sequence based on the sequence formula of SEQ ID NO: 45, 46 or 57, or region thereof, such as residues 90-211, having the specified features at residues X145 and/or X153 as described herein, can further include at least the following features: residue corresponding to X96 is an aliphatic, basic, nonpolar or polar residue, particularly alanine, lysine, glutamine or arginine. In some embodiments, the ketoreductase polypeptide comprises an amino acid sequence with at least the preceding features, and wherein the amino acid sequence has at least 85%, 86%, 87%, 88%, 89%, 90%, 91%, 92%, 93%, 94%, 95%, 96%, 97%, 98%, or 99% identity as compared to a reference sequence based on SEQ ID NO:2, 4 or 48 with the preceding features. In some embodiments, the ketoreductase polypeptides can have additionally 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-26, 1-30, 1-35 or about 1-40 residue differences at other amino acid residues as compared to the reference sequence. In some embodiments, the number of differences can be 1, 2, 3, 4, 5, 6, 7, 8, 9, 10, 11, 12, 14, 15, 16, 18, 20, 22, 24, 26, 30, 35 or about 40 residue differences at other amino acid residues. In some embodiments, the differences with the reference sequence comprise conservative mutations.

In some embodiments, the improved ketoreductase polypeptide comprising an amino acid sequence based on the sequence formula of SEQ ID NO: 45, 46 or 57, or region thereof, such as residues 90-211, having the specified features at residues X145 and/or X153 as described herein, can further include at least the following features: residue corresponding to X104 is a nonpolar or polar residue, particularly methionine. In some embodiments, the ketoreductase polypeptide comprises an amino acid sequence with at least the preceding features, and wherein the amino acid sequence has at least 85%, 86%, 87%, 88%, 89%, 90%, 91%, 92%, 93%, 94%, 95%, 96%, 97%, 98%, or 99% identity as compared to a reference sequence based on SEQ ID NO:2, 4 or 48 with the preceding features. In some embodiments, the ketoreductase polypeptides can have additionally 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-26, 1-30, 1-35 or about 1-40 residue differences at other amino acid residues as compared to the reference sequence. In some embodiments, the number of differences can be 1, 2, 3, 4, 5, 6, 7, 8, 9, 10, 11, 12, 14, 15, 16, 18, 20, 22, 24, 26, 30, 35 or about 40 residue differences at other amino acid residues. In some embodiments, the differences with the reference sequence comprise conservative mutations.

In some embodiments, the improved ketoreductase polypeptide comprising an amino acid sequence based on the sequence formula of SEQ ID NO: 45, 46 or 57, or region thereof, such as residues 90-211, having the specified features at residues X145 and/or X153 as described herein, can further include at least the following features: residue corresponding to X117 is a nonpolar or polar residue, particularly serine. In some embodiments, the ketoreductase polypeptide comprises an amino acid sequence with at least the preceding features, and wherein the amino acid sequence has at least 85%, 86%, 87%, 88%, 89%, 90%, 91%, 92%, 93%, 94%, 95%, 96%, 97%, 98%, or 99% identity as compared to a reference sequence based on SEQ ID NO:2, 4 or 48 with the preceding features. In some embodiments, the ketoreductase polypeptides can have additionally 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-26, 1-30, 1-35 or about 1-40 residue differences at other amino acid residues as compared to the reference sequence. In some embodiments, the number of differences can be 1, 2, 3, 4, 5, 6, 7, 8, 9, 10, 11, 12, 14, 15, 16, 18, 20, 22, 24, 26, 30, 35 or about 40 residue differences at other amino acid residues. In some embodiments, the differences with the reference sequence comprise conservative mutations.

In some embodiments, the improved ketoreductase polypeptide comprising an amino acid sequence based on the sequence formula of SEQ ID NO: 45, 46 or 57, or region thereof, such as residues 90-211, having the specified features at residues X145 and/or X153 as described herein, can further include at least the following features: residue corresponding to X147 is a cysteine, aliphatic or nonpolar residue, particularly methionine, leucine, valine or cysteine. In some embodiments, the ketoreductase polypeptide comprises an amino acid sequence with at least the preceding features, and wherein the amino acid sequence has at least 85%, 86%, 87%, 88%, 89%, 90%, 91%, 92%, 93%, 94%, 95%, 96%, 97%, 98%, or 99% identity as compared to a reference sequence based on SEQ ID NO:2, 4 or 48 with the preceding features. In some embodiments, the ketoreductase polypeptides can have additionally 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-26, 1-30, 1-35 or about 1-40 residue differences at other amino acid residues as compared to the reference sequence. In some embodiments, the number of differences can be 1, 2, 3, 4, 5, 6, 7, 8, 9, 10, 11, 12, 14, 15, 16, 18, 20, 22, 24, 26, 30, 35 or about 40 residue differences at other amino acid residues. In some embodiments, the differences with the reference sequence comprise conservative mutations.

In some embodiments, the improved ketoreductase polypeptide comprising an amino acid sequence based on the sequence formula of SEQ ID NO: 45, 46 or 57, or region thereof, such as residues 90-211, having the specified features at residues X145 and/or X153 as described herein, can further include at least the following features: residue corresponding to X157 is a polar residue, particularly threonine. In some embodiments, the ketoreductase polypeptide comprises an amino acid sequence with at least the preceding features, and wherein the amino acid sequence has at least 85%, 86%, 87%, 88%, 89%, 90%, 91%, 92%, 93%, 94%, 95%, 96%, 97%, 98%, or 99% identity as compared to a reference sequence based on SEQ ID NO:2, 4 or 48 with the preceding features. In some embodiments, the ketoreductase polypeptides can have additionally 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-26, 1-30, 1-35 or about 1-40 residue differences at other amino acid residues as compared to the reference sequence. In some embodiments, the number of differences can be 1, 2, 3, 4, 5, 6, 7, 8, 9, 10, 11, 12, 14, 15, 16, 18, 20, 22, 24, 26, 30, 35 or about 40 residue differences at other amino acid residues. In some embodiments, the differences with the reference sequence comprise conservative mutations.

In some embodiments, the improved ketoreductase polypeptide comprising an amino acid sequence based on the sequence formula of SEQ ID NO: 45, 46 or 57, or region thereof, such as residues 90-211, having the specified features at residues X145 and/or X153 as described herein, can further include at least the following features: residue corresponding to X178 is a nonpolar residue, particularly glycine. In some embodiments, the ketoreductase polypeptide comprises an amino acid sequence with at least the preceding features, and wherein the amino acid sequence has at least 85%, 86%, 87%, 88%, 89%, 90%, 91%, 92%, 93%, 94%, 95%, 96%, 97%, 98%, or 99% identity as compared to a reference sequence based on SEQ ID NO:2, 4 or 48 with the preceding features. In some embodiments, the ketoreductase polypeptides can have additionally 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-26, 1-30, 1-35 or about 1-40 residue differences at other amino acid residues as compared to the reference sequence. In some embodiments, the number of differences can be 1, 2, 3, 4, 5, 6, 7, 8, 9, 10, 11, 12, 14, 15, 16, 18, 20, 22, 24, 26, 30, 35 or about 40 residue differences at other amino acid residues. In some embodiments, the differences with the reference sequence comprise conservative mutations.

In some embodiments, the improved ketoreductase polypeptide comprising an amino acid sequence based on the sequence formula of SEQ ID NO: 45, 46 or 57, or region thereof, such as residues 90-211, having the specified features at residues X145 and/or X153 as described herein, can further include at least the following features: residue corresponding to X202 is an aliphatic, basic, or nonpolar residue, particularly valine or isoleucine. In some embodiments, the ketoreductase polypeptide comprises an amino acid sequence with at least the preceding features, and wherein the amino acid sequence has at least 85%, 86%, 87%, 88%, 89%, 90%, 91%, 92%, 93%, 94%, 95%, 96%, 97%, 98%, or 99% identity as compared to a reference sequence based on SEQ ID NO:2, 4 or 48 with the preceding features. In some embodiments, the ketoreductase polypeptides can have additionally 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-26, 1-30, 1-35 or about 1-40 residue differences at other amino acid residues as compared to the reference sequence. In some embodiments, the number of differences can be 1, 2, 3, 4, 5, 6, 7, 8, 9, 10, 11, 12, 14, 15, 16, 18, 20, 22, 24, 26, 30, 35 or about 40 residue differences at other amino acid residues. In some embodiments, the differences with the reference sequence comprise conservative mutations.

In some embodiments, the improved ketoreductase polypeptide comprising an amino acid sequence based on the sequence formula of SEQ ID NO: 45, 46 or 57, or region thereof, such as residue 90-211, having the specified features of residues X145 and/or X153 as described herein, can further include at least the following features: residue corresponding to X223 is an aliphatic or nonpolar residue, particularly valine. In some embodiments, the ketoreductase polypeptide comprises an amino acid sequence with at least the preceding features, and wherein the amino acid sequence has at least 85%, 86%, 87%, 88%, 89%, 90%, 91%, 92%, 93%, 94%, 95%, 96%, 97%, 98%, or 99% identity as compared to a reference sequence based on SEQ ID NO:2, 4 or 48 with the preceding features. In some embodiments, the ketoreductase polypeptides can have additionally 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-26, 1-30, 1-35 or about 1-40 residue differences at other amino acid residues as compared to the reference sequence. In some embodiments, the number of differences can be 1, 2, 3, 4, 5, 6, 7, 8, 9, 10, 11, 12, 14, 15, 16, 18, 20, 22, 24, 26, 30, 35 or about 40 residue differences at other amino acid residues. In some embodiments, the differences with the reference sequence comprise conservative mutations.

In some embodiments, the improved ketoreductase polypeptide comprising an amino acid sequence based on the sequence formula of SEQ ID NO: 45, 46 or 57, or region thereof, such as residues 90-211, having the specified features at residues X145 and/or X153 as described herein, can further include at least the following features: residue corresponding to X236 is a basic residue, particularly arginine. In some embodiments, the ketoreductase polypeptide comprises an amino acid sequence with at least the preceding features, and wherein the amino acid sequence has at least 85%, 86%, 87%, 88%, 89%, 90%, 91%, 92%, 93%, 94%, 95%, 96%, 97%, 98%, or 99% identity as compared to a reference sequence based on SEQ ID NO:2, 4 or 48 with the preceding features. In some embodiments, the ketoreductase polypeptides can have additionally 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-26, 1-30, 1-35 or about 1-40 residue differences at other amino acid residues as compared to the reference sequence. In some embodiments, the number of differences can be 1, 2, 3, 4, 5, 6, 7, 8, 9, 10, 11, 12, 14, 15, 16, 18, 20, 22, 24, 26, 30, 35 or about 40 residue differences at other amino acid residues. In some embodiments, the differences with the reference sequence comprise conservative mutations.

In some embodiments, the improved ketoreductase polypeptide comprising an amino acid sequence based on the sequence formula of SEQ ID NO:45, 46 or 57, or region thereof, such as residues 90-211, having the specified features at residues X145 and/or X153 as described herein, can further include at least the following features: residue corresponding to X82 is a polar residue, particularly serine; and X147 is an aliphatic, non-polar residue, or cysteine, particularly cysteine, methionine, leucine or valine. In some embodiments, the ketoreductase polypeptide comprises an amino acid sequence with at least the preceding features, and wherein the amino acid sequence has at least 85%, 86%, 87%, 88%, 89%, 90%, 91%, 92%, 93%, 94%, 95%, 96%, 97%, 98%, or 99% identity as compared to a reference sequence based on SEQ ID NO:2, 4 or 48 with the preceding features. In some embodiments, the ketoreductase polypeptides can have additionally 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-26, 1-30, 1-35 or about 1-40 residue differences at other amino acid residues as compared to the reference sequence. In some embodiments, the number of differences can be 1, 2, 3, 4, 5, 6, 7, 8, 9, 10, 11, 12, 14, 15, 16, 18, 20, 22, 24, 26, 30, 35 or about 40 residue differences at other amino acid residues. In some embodiments, the differences with the reference sequence comprise conservative mutations.

In some embodiments, the improved ketoreductase polypeptide comprising an amino acid sequence based on the sequence formula of SEQ ID NO:45, 46 or 57, or region thereof, such as residues 90-211, having the specified features at residues X145 and/or X153 as described herein, can further include at least the following features: residue corresponding to X82 is a polar residue, particularly serine, and residue corresponding to X223 is an aliphatic or nonpolar residue, particularly valine. In some embodiments, the ketoreductase polypeptide comprises an amino acid sequence with at least the preceding features, and wherein the amino acid sequence has at least 85%, 86%, 87%, 88%, 89%, 90%, 91%, 92%, 93%, 94%, 95%, 96%, 97%, 98%, or 99% identity as compared to a reference sequence based on SEQ ID NO:2, 4 or 48 with the preceding features. In some embodiments, the ketoreductase polypeptides can have additionally 1-2, 1-3, 1-4, 1-5, 1-6, 1-7, 1-8, 1-9,1-10, 1-11, 1-12, 1-14, 1-15, 1-16, 1-18, 1-20, 1-22, 1-24, 1-26, 1-30, 1-35 or about 1-40 residue differences at other amino acid residues as compared to the reference sequence. In some embodiments, the number of differences can be 1, 2, 3, 4, 5, 6, 7, 8, 9, 10, 11, 12, 14, 15, 16, 18, 20, 22, 24, 26, 30, 35 or about 40 residue differences at other amino acid residues. In some embodiments, the differences with the reference sequence comprise conservative mutations.

In some embodiments, the improved ketoreductase polypeptide comprising an amino acid sequence based on the sequence formula of SEQ ID NO:45, 46 or 57, or region thereof, such as residues 90-211, having the specified features at residues X145 and/or X153 as described herein, can further include at least the following features: residue corresponding to X147 is a cysteine or non-polar or aliphatic residue, particularly cysteine, valine, methionine, or leucine, and corresponding to X223 is a non-polar or aliphatic residue, particularly valine. In some embodiments, the ketoreductase polypeptide comprises an amino acid sequence with at least the preceding features, and wherein the amino acid sequence has at least 85%, 86%, 87%, 88%, 89%, 90%, 91%, 92%, 93%, 94%, 95%, 96%, 97%, 98%, or 99% identity as compared to a reference sequence based on SEQ ID NO:2, 4 or 48 with the preceding features. In some embodiments, the ketoreductase polypeptides can have additionally 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-26, 1-30, 1-35 or about 1-40 residue differences at other amino acid residues as compared to the reference sequence. In some embodiments, the number of differences can be 1, 2, 3, 4, 5, 6, 7, 8, 9, 10, 11, 12, 14, 15, 16, 18, 20, 22, 24, 26, 30, 35 or about 40 residue differences at other amino acid residues. In some embodiments, the differences with the reference sequence comprise conservative mutations.

In some embodiments, the improved ketoreductase polypeptide comprising an amino acid sequence based on the sequence formula of SEQ ID NO:45, 46 or 57, or region thereof, such as residues 90-211, having the specified features at residues X145 and/or X153 as described herein, can further include at least the following features: residue corresponding to X96 is a nonpolar or aliphatic residue, particularly alanine, and residue corresponding to X147 is a cysteine or non-polar or aliphatic residue, particularly cysteine, valine, methionine, or leucine. In some embodiments, the ketoreductase polypeptide comprises an amino acid sequence with at least the preceding features, and wherein the amino acid sequence has at least 85%, 86%, 87%, 88%, 89%, 90%, 91%, 92%, 93%, 94%, 95%, 96%, 97%, 98%, or 99% identity as compared to a reference sequence based on SEQ ID NO:2, 4 or 48 with the preceding features. In some embodiments, the ketoreductase polypeptides can have additionally 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-26, 1-30, 1-35 or about 1-40 residue differences at other amino acid residues as compared to the reference sequence. In some embodiments, the number of differences can be 1, 2, 3, 4, 5, 6, 7, 8, 9, 10, 11, 12, 14, 15, 16, 18, 20, 22, 24, 26, 30, 35 or about 40 residue differences at other amino acid residues. In some embodiments, the differences with the reference sequence comprise conservative mutations.

In some embodiments, the improved ketoreductase polypeptide comprising an amino acid sequence based on the sequence formula of SEQ ID NO:45, 46 or 57, or region thereof, such as residues 90-211, having the specified features at residues X145 and/or X153 as described herein, can further include at least the following features: residue corresponding to X96 is a nonpolar or aliphatic residue, particularly alanine, and residue corresponding to X104 is a non-polar or polar residue, particularly methionine. In some embodiments, the ketoreductase polypeptide comprises an amino acid sequence with at least the preceding features, and wherein the amino acid sequence has at least 85%, 86%, 87%, 88%, 89%, 90%, 91%, 92%, 93%, 94%, 95%, 96%, 97%, 98%, or 99% identity as compared to a reference sequence based on SEQ ID NO:2, 4 or 48 with the preceding features. In some embodiments, the ketoreductase polypeptides can have additionally 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-26, 1-30, 1-35 or about 1-40 residue differences at other amino acid residues as compared to the reference sequence. In some embodiments, the number of differences can be 1, 2, 3, 4, 5, 6, 7, 8, 9, 10, 11, 12, 14, 15, 16, 18, 20, 22, 24, 26, 30, 35 or about 40 residue differences at other amino acid residues. In some embodiments, the differences with the reference sequence comprise conservative mutations.

In some embodiments, the improved ketoreductase polypeptide comprising an amino acid sequence based on the sequence formula of SEQ ID NO:45, 46 or 57, or region thereof, such as residues 90-211, having the specified features at residues X145 and/or X153 as described herein, can further include at least the following features: residue corresponding to X96 is a nonpolar or aliphatic residue, particularly alanine, and residue corresponding to X236 is a basic residue, particularly arginine. In some embodiments, the ketoreductase polypeptide comprises an amino acid sequence with at least the preceding features, and wherein the amino acid sequence has at least 85%, 86%, 87%, 88%, 89%, 90%, 91%, 92%, 93%, 94%, 95%, 96%, 97%, 98%, or 99% identity as compared to a reference sequence based on SEQ ID NO:2, 4 or 48 with the preceding features. In some embodiments, the ketoreductase polypeptides can have additionally 1-2, 1-3, 1-4, 1-5, 1-6, 1-7, 1-8, 1-9,1-10, 1-11, 1-12, 1-14, 1-15, 1-16, 1-18, 1-20, 1-22, 1-24, 1-26, 1-30, 1-35 or about 1-40 residue differences at other amino acid residues as compared to the reference sequence. In some embodiments, the number of differences can be 1, 2, 3, 4, 5, 6, 7, 8, 9, 10, 11, 12, 14, 15, 16, 18, 20, 22, 24, 26, 30, 35 or about 40 residue differences at other amino acid residues. In some embodiments, the differences with the reference sequence comprise conservative mutations.

In some embodiments, the improved ketoreductase polypeptide comprising an amino acid sequence based on the sequence formula of SEQ ID NO:45, 46 or 57, or region thereof, such as residues 90-211, having the specified features at residues X145 and/or X153 as described herein, can further include at least the following features: residue corresponding to X117 is a polar residue, particularly serine, and residue corresponding to X202 is a non-polar or aliphatic residue, particularly valine or isoleucine. In some embodiments, the ketoreductase polypeptide comprises an amino acid sequence with at least the preceding features, and wherein the amino acid sequence has at least 85%, 86%, 87%, 88%, 89%, 90%, 91%, 92%, 93%, 94%, 95%, 96%, 97%, 98%, or 99% identity as compared to a reference sequence based on SEQ ID NO:2, 4 or 48 with the preceding features. In some embodiments, the ketoreductase polypeptides can have additionally 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-26, 1-30, 1-35 or about 1-40 residue differences at other amino acid residues as compared to the reference sequence. In some embodiments, the number of differences can be 1, 2, 3, 4, 5, 6, 7, 8, 9, 10, 11, 12, 14, 15, 16, 18, 20, 22, 24, 26, 30, 35 or about 40 residue differences at other amino acid residues. In some embodiments, the differences with the reference sequence comprise conservative mutations.

In some embodiments, the improved ketoreductase polypeptide comprising an amino acid sequence based on the sequence formula of SEQ ID NO:45, 46 or 57, or region thereof, such as residue 90-211, having the specified features at residues X145 and/or X153 as described herein, can further include at least the following features: residue corresponding to X82 is a polar residue, particularly serine; residue corresponding to X147 is a cysteine or non-polar or aliphatic residue, particularly cysteine, methionine, valine and leucine; and residue corresponding to X178 is a non-polar residue, particularly glycine. In some embodiments, the ketoreductase polypeptide comprises an amino acid sequence with at least the preceding features, and wherein the amino acid sequence has at least 85%, 86%, 87%, 88%, 89%, 90%, 91%, 92%, 93%, 94%, 95%, 96%, 97%, 98%, or 99% identity as compared to a reference sequence based on SEQ ID NO:2, 4 or 48 with the preceding features. In some embodiments, the ketoreductase polypeptides can have additionally 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-26, 1-30, 1-35 or about 1-40 residue differences at other amino acid residues as compared to the reference sequence. In some embodiments, the number of differences can be 1, 2, 3, 4, 5, 6, 7, 8, 9, 10, 11, 12, 14, 15, 16, 18, 20, 22, 24, 26, 30, 35 or about 40 residue differences at other amino acid residues. In some embodiments, the differences with the reference sequence comprise conservative mutations.

In some embodiments, an improved ketoreductase comprises an amino acid sequence that is at least about 85%, 86%, 87%, 88%, 89%, 90%, 91%, 92%, 93%, 94%, 95%, 96%, 97%, 98%, or 99% identical to a reference sequence selected from SEQ ID NO:6, 8, 10, 12, 14, 16, 18, 20, 22, 24, 26, 28, 30, 32, 34, 36, 38, 40, 42, and 44, as listed in Table 2, wherein the improved ketoreductase polypeptide amino acid sequence includes any one set of the specified amino acid substitution combinations presented in Table 2. In some embodiments, these ketoreductase polypeptides can have additionally 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-25, 1-30, 1-35 or about 1-40 residue differences at other amino acid residues as compared to the reference sequence. In some embodiments, the number of differences can be at 1, 2, 3, 4, 5, 6, 7, 8, 9, 10, 11, 12, 14, 15, 16, 18, 20, 22, 24, 26, 30, 35 or about 40 residue differences at other amino acid residues. The differences with the reference sequence can comprise insertions, deletions, or substitutions, or combinations thereof. In some embodiments, the differences comprise conservative mutations.

In some embodiments, an improved ketoreductase polypeptide comprises an amino acid sequence based on the sequence formula of SEQ ID NO: 45, 46 or 57, or a region thereof, such as residues 90-211, in which the amino acid sequence has at least the following features: residue corresponding to X96 is an aliphatic, basic, non-polar or polar residue, particularly alanine; residue corresponding to X104 is a nonpolar or polar residue, particularly methionine; residue corresponding to X117 is nonpolar or polar residue, particularly serine; residue corresponding to X145 is a polar residue, particularly serine; and residue corresponding to X202 is an aliphatic, basic, or non-polar residue, particularly valine. In some embodiments, the ketoreductase polypeptides can have additionally 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-25, 1-30, 1-35 or about 1-40 residue differences at other residue positions as compared to the reference sequence of SEQ ID NO:6. In some embodiments, the number of differences can be 1, 2, 3, 4, 5, 6, 7, 8, 9, 10, 11, 12, 14, 15, 16, 18, 20, 22, 24, 26, 30, 35 or about 40 residue differences at other amino acid residue positions. In some embodiments, the differences comprise conservative mutations. In some embodiments, the ketoreductase polypeptide comprises an amino acid sequence with the preceding features, and wherein the amino acid sequence has at least 85%, 86%, 87%, 88%, 89%, 90%, 91%, 92%, 93%, 94%, 95%, 96%, 97%, 98%, or 99% identity to SEQ ID NO:6.

In some embodiments, an improved ketoreductase polypeptide comprises an amino acid sequence based on the sequence formula of SEQ ID NO:45, 46 or 57, or a region thereof, such as residues 90-211, and has at least the following features: residue corresponding to X117 is a nonpolar or polar residue, particularly serine; residue corresponding to X145 is a polar residue, particularly serine; residue corresponding to X157 is a polar residue, particularly threonine; and residue corresponding to X223 is an aliphatic or nonpolar residue, particularly valine. In some embodiments, the ketoreductase polypeptides can have additionally 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-25, 1-30, 1-35 or about 1-40 residue differences at other residue positions as compared to the reference sequence of SEQ ID NO:8. In some embodiments, the number of differences can be 1, 2, 3, 4, 5, 6, 7, 8, 9, 10, 11, 12, 14, 15, 16, 18, 20, 22, 24, 26, 30, 35 or about 40 residue differences at other amino acid residue positions. In some embodiments, the differences comprise conservative mutations. In some embodiments, the ketoreductase polypeptide comprises an amino acid sequence with the preceding features, and wherein the amino acid sequence has at least 85%, 86%, 87%, 88%, 89%, 90%, 91%, 92%, 93%, 94%, 95%, 96%, 97%, 98%, or 99% identity to SEQ ID NO:8.

In some embodiments, an improved ketoreductase polypeptide comprises an amino acid sequence based on the sequence formula of SEQ ID NO:45, 46 or 57, or a region thereof, such as residues 90-211, and has at least the following features: residue corresponding to X104 is a nonpolar or polar residue, particularly methionine; residue corresponding to X145 is a polar residue, particularly serine; and residue corresponding to X202 is an aliphatic, basic, or nonpolar residue, particularly isoleucine or valine. In some embodiments, the ketoreductase polypeptides can have additionally 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-25, 1-30, 1-35 or about 1-40 residue differences at other residue positions as compared to the reference sequence of SEQ ID NO:10 or SEQ ID NO:12. In some embodiments, the number of differences can be 1, 2, 3, 4, 5, 6, 7, 8, 9, 10, 11, 12, 14, 15, 16, 18, 20, 22, 24, 26, 30, 35 or about 40 residue differences at other amino acid residue positions. In some embodiments, the differences comprise conservative mutations. In some embodiments, the ketoreductase polypeptide comprises an amino acid sequence with the preceding features, and wherein the amino acid sequence has at least 85%, 86%, 87%, 88%, 89%, 90%, 91%, 92%, 93%, 94%, 95%, 96%, 97%, 98%, or 99% identity to SEQ ID NO:10 or SEQ ID NO:12.

In some embodiments, an improved ketoreductase polypeptide comprises an amino acid sequence based on the sequence formula of SEQ ID NO:45, 46 or 57, or a region thereof, such as residues 90-211, and has at least the following features: residue corresponding to X72 is an acidic residue, particularly glutamic acid; residue corresponding to X96 is an aliphatic, basic, nonpolar or polar residue, particularly alanine; residue corresponding to X104 is a nonpolar or polar residue, particularly methionine; residue corresponding to X117 is a nonpolar or polar residue, particularly serine; residue corresponding to X145 is a polar residue, particularly serine, and residue corresponding to X153 is polar residue, particularly glutamine. In some embodiments, the ketoreductase polypeptides can have additionally 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-25, 1-30, 1-35 or about 1-40 residue differences at other residue positions as compared to the reference sequence of SEQ ID NO:14. In some embodiments, the number of differences can be 1, 2, 3, 4, 5, 6, 7, 8, 9, 10, 11, 12, 14, 15, 16, 18, 20, 22, 24, 26, 30, 35 or about 40 residue differences at other amino acid residue positions. In some embodiments, the differences comprise conservative mutations. In some embodiments, the ketoreductase polypeptide comprises an amino acid sequence with the preceding features, and wherein the amino acid sequence has at least 85%, 86%, 87%, 88%, 89%, 90%, 91%, 92%, 93%, 94%, 95%, 96%, 97%, 98%, or 99% identity to SEQ ID NO:14.

In some embodiments, an improved ketoreductase polypeptide comprises an amino acid sequence based on the sequence formula of SEQ ID NO:45, 46 or 57, or a region thereof, such as residues 90-211, and has at least the following features: residue corresponding to X96 is an aliphatic, basic, nonpolar or polar residue, particularly lysine, glutamine, or arginine; residue corresponding to X153 is a polar residue, particularly glutamine, and residue corresponding to X236 is a basic residue, particularly arginine. In some embodiments, the ketoreductase polypeptides can have additionally 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-25, 1-30, 1-35 or about 1-40 residue differences at other residue positions as compared to the reference sequence of SEQ ID NO:16, SEQ ID NO:18, or SEQ ID NO:20. In some embodiments, the number of differences can be 1, 2, 3, 4, 5, 6, 7, 8, 9, 10, 11, 12, 14, 15, 16, 18, 20, 22, 24, 26, 30, 35 or about 40 residue differences at other amino acid residue positions. In some embodiments, the differences comprise conservative mutations. In some embodiments, the ketoreductase polypeptide comprises an amino acid sequence with the preceding features, and wherein the amino acid sequence has at least 85%, 86%, 87%, 88%, 89%, 90%, 91%, 92%, 93%, 94%, 95%, 96%, 97%, 98%, or 99% identity to SEQ ID NO:16, SEQ ID NO:18, or SEQ ID NO:20.

In some embodiments, an improved ketoreductase polypeptides comprises an amino acid sequence based on the sequence formula of SEQ ID NO:45, 46 or 57, or a region thereof, such as residues 90-211, and has at least the following features: residue corresponding to X153 is a polar residue, particularly glutamine, and residue corresponding to X236 is a basic residue, particularly arginine. In some embodiments, the ketoreductase polypeptides can have additionally 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-25, 1-30, 1-35 or about 1-40 residue differences at other residue positions as compared to the reference sequence of SEQ ID NO:22. In some embodiments, the number of differences can be 1, 2, 3, 4, 5, 6, 7, 8, 9, 10, 11, 12, 14, 15, 16, 18, 20, 22, 24, 26, 30, 35 or about 40 residue differences at other amino acid residue positions. In some embodiments, the differences comprise conservative mutations. In some embodiments, the ketoreductase polypeptide comprises an amino acid sequence with the preceding features, and wherein the amino acid sequence has at least 85%, 86%, 87%, 88%, 89%, 90%, 91%, 92%, 93%, 94%, 95%, 96%, 97%, 98%, or 99% identity to SEQ ID NO:22.

In some embodiments, an improved ketoreductase polypeptides comprises an amino acid sequence based on the sequence formula of SEQ ID NO:45, 46 or 57, or a region thereof, such as residues 90-211, and has at least the following features: residue corresponding to X82 is a polar residue, particularly serine; residue corresponding to X96 is an aliphatic, basic, nonpolar or polar residue, particularly alanine; residue corresponding to X145 is nonpolar residue, particularly serine; and residue corresponding to X153 is a polar residue, particularly glutamine. In some embodiments, the ketoreductase polypeptides can have additionally 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-25, 1-30, 1-35 or about 1-40 residue differences at other residue positions as compared to the reference sequence of SEQ ID NO:24. In some embodiments, the number of differences can be 1, 2, 3, 4, 5, 6, 7, 8, 9, 10, 11, 12, 14, 15, 16, 18, 20, 22, 24, 26, 30, 35 or about 40 residue differences at other amino acid residue positions. In some embodiments, the differences comprise conservative mutations. In some embodiments, the ketoreductase polypeptide comprises an amino acid sequence with the preceding features, and wherein the amino acid sequence has at least 85%, 86%, 87%, 88%, 89%, 90%, 91%, 92%, 93%, 94%, 95%, 96%, 97%, 98%, or 99% identity to SEQ ID NO:24.

In some embodiments, an improved ketoreductase polypeptides comprises an amino acid sequence based on the sequence formula of SEQ ID NO:45, 46 or 57, or a region thereof, such as residues 90-211, and has at least the following features: residue corresponding to X82 is a polar residue, particularly serine; residue corresponding to X96 is an aliphatic, basic, nonpolar or polar residue, particularly alanine; residue corresponding to X145 is a polar residue, particularly serine; residue corresponding to X153 is a polar residue, particularly glutamine; and residue corresponding to X223 is an aliphatic or nonpolar residue, particularly valine. In some embodiments, the ketoreductase polypeptides can have additionally 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-25, 1-30, 1-35 or about 1-40 residue differences at other residue positions as compared to the reference sequence of SEQ ID NO:26. In some embodiments, the number of differences can be 1, 2, 3, 4, 5, 6, 7, 8, 9, 10, 11, 12, 14, 15, 16, 18, 20, 22, 24, 26, 30, 35 or about 40 residue differences at other amino acid residue positions. In some embodiments, the differences comprise conservative mutations. In some embodiments, the ketoreductase polypeptide comprises an amino acid sequence with the preceding features, and wherein the amino acid sequence has at least 85%, 86%, 87%, 88%, 89%, 90%, 91%, 92%, 93%, 94%, 95%, 96%, 97%, 98%, or 99% identity to SEQ ID NO:26.

In some embodiments, an improved ketoreductase polypeptides comprises an amino acid sequence based on the sequence formula of SEQ ID NO:45, 46 or 57, or a region thereof, such as residues 90-211, and has at least the following features: residue corresponding to X82 is a polar residue, particularly serine; residue corresponding to X153 is a polar residue, particularly glutamine; and residue corresponding to X223 is an aliphatic or nonpolar residue, particularly valine. In some embodiments, the ketoreductase polypeptides can have additionally 1-2, 1-3, 1-4, 1-5, 1-6, 1-7, 1-8, 1-9,1-10, 1-11, 1-12, 1-14, 1-15, 1-16, 1-18, 1-20, 1-22, 1-24, 1-25, 1-30, 1-35 or about 1-40 residue differences at other residue positions as compared to the reference sequence of SEQ ID NO:30. In some embodiments, the number of differences can be 1, 2, 3, 4, 5, 6, 7, 8, 9, 10, 11, 12, 14, 15, 16, 18, 20, 22, 24, 26, 30, 35 or about 40 residue differences at other amino acid residue positions. In some embodiments, the differences comprise conservative mutations. In some embodiments, the ketoreductase polypeptide comprises an amino acid sequence with the preceding features, and wherein the amino acid sequence has at least 85%, 86%, 87%, 88%, 89%, 90%, 91%, 92%, 93%, 94%, 95%, 96%, 97%, 98%, or 99% identity to SEQ ID NO:30.

In some embodiments, an improved ketoreductase polypeptides comprises an amino acid sequence based on the sequence formula of SEQ ID NO:45, 46 or 57, or a region thereof, such as residues 90-211, and has at least the following features: residue corresponding to X82 is a polar residue, particularly serine; residue corresponding to X145 is a polar residue, particularly serine; residue corresponding to X147 is a cysteine, aliphatic or nonpolar residue, particularly methionine, leucine, valine, or cysteine; residue corresponding to X153 is a polar residue, particularly glutamine; and residue corresponding to X223 is an aliphatic or nonpolar residue, particularly valine. In some embodiments, the ketoreductase polypeptides can have additionally 1-2, 1-3, 1-4, 1-5, 1-6, 1-7, 1-8, 1-9,1-10, 1-11, 1-12, 1-14, 1-15, 1-16, 1-18, 1-20, 1-22, 1-24, 1-25, 1-30, 1-35 or about 1-40 residue differences at other residue positions as compared to the reference sequence of SEQ ID NO:32, 34, 36 or 40. In some embodiments, the number of differences can be 1, 2, 3, 4, 5, 6, 7, 8, 9, 10, 11, 12, 14, 15, 16, 18, 20, 22, 24, 26, 30, 35 or about 40 residue differences at other amino acid residue positions. In some embodiments, the differences comprise conservative mutations. In some embodiments, the ketoreductase polypeptide comprises an amino acid sequence with the preceding features, and wherein the amino acid sequence has at least 85%, 86%, 87%, 88%, 89%, 90%, 91%, 92%, 93%, 94%, 95%, 96%, 97%, 98%, or 99% identity to SEQ ID NO:32, 34, 36 or 40.

In some embodiments, an improved ketoreductase polypeptides comprises an amino acid sequence based on the sequence formula of SEQ ID NO:45, 46 or 57, or a region thereof, such as residues 90-211, and has at least the following features: residue corresponding to X82 is a polar residue, particularly serine; residue corresponding to X145 is a polar residue, particularly serine; residue corresponding to X147 is a cysteine, aliphatic or nonpolar residue, particularly valine; residue corresponding to X153 is a polar residue, particularly glutamine; residue corresponding to X178 is a nonpolar residue, particularly glycine, and residue corresponding to X223 is an aliphatic or nonpolar residue, particularly valine. In some embodiments, the ketoreductase polypeptides can have additionally 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-25, 1-30, 1-35 or about 1-40 residue differences at other residue positions as compared to the reference sequence of SEQ ID NO:38. In some embodiments, the number of differences can be 1, 2, 3, 4, 5, 6, 7, 8, 9, 10, 11, 12, 14, 15, 16, 18, 20, 22, 24, 26, 30, 35 or about 40 residue differences at other amino acid residue positions. In some embodiments, the differences comprise conservative mutations. In some embodiments, the ketoreductase polypeptide comprises an amino acid sequence with the preceding features, and wherein the amino acid sequence has at least 85%, 86%, 87%, 88%, 89%, 90%, 91%, 92%, 93%, 94%, 95%, 96%, 97%, 98%, or 99% identity to SEQ ID NO:38.

In some embodiments, an improved ketoreductase polypeptides comprises an amino acid sequence based on the sequence formula of SEQ ID NO:45, 46 or 57, or a region thereof, such as residues 90-211, and has at least the following features: residue corresponding to X82 is a polar residue, particularly serine; residue corresponding to X145 is a polar residue, particularly serine; residue corresponding to X153 is a polar residue, particularly glutamine; and residue corresponding to X223 is an aliphatic or nonpolar residue, particularly valine. In some embodiments, the ketoreductase polypeptides can have additionally 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-25, 1-30, 1-35 or about 1-40 residue differences at other residue positions as compared to the reference sequence of SEQ ID NO:42. In some embodiments, the number of differences can be 1, 2, 3, 4, 5, 6, 7, 8, 9, 10, 11, 12, 14, 15, 16, 18, 20, 22, 24, 26, 30, 35 or about 40 residue differences at other amino acid residue positions. In some embodiments, the differences comprise conservative mutations. In some embodiments, the ketoreductase polypeptide comprises an amino acid sequence with the preceding features, and wherein the amino acid sequence has at least 85%, 86%, 87%, 88%, 89%, 90%, 91%, 92%, 93%, 94%, 95%, 96%, 97%, 98%, or 99% identity to SEQ ID NO:42.

In some embodiments, an improved ketoreductase polypeptides comprises an amino acid sequence based on the sequence formula of SEQ ID NO:45, 46 or 57, or a region thereof, such as residues 90-211, and has at least the following features: residue corresponding to X46 is a basic residue, particularly arginine; residue corresponding to X82 is a polar residue, particularly serine; residue corresponding to X145 is a polar residue, particularly serine; residue corresponding to X153 is a polar residue, particularly glutamine; and residue corresponding to X223 is an aliphatic or nonpolar residue, particularly valine. In some embodiments, the ketoreductase polypeptides can have additionally 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-25, 1-30, 1-35 or about 1-40 residue differences at other residue positions as compared to the reference sequence of SEQ ID NO:44. In some embodiments, the number of differences can be 1, 2, 3, 4, 5, 6, 7, 8, 9, 10, 11, 12, 14, 15, 16, 18, 20, 22, 24, 26, 30, 35 or about 40 residue differences at other amino acid residue positions. In some embodiments, the differences comprise conservative mutations. In some embodiments, the ketoreductase polypeptide comprises an amino acid sequence with the preceding features, and wherein the amino acid sequence has at least 85%, 86%, 87%, 88%, 89%, 90%, 91%, 92%, 93%, 94%, 95%, 96%, 97%, 98%, or 99% identity to SEQ ID NO:44.

In some embodiments, the improved ketoreductase polypeptides of the invention can comprise a region or domain corresponding to residues 90-211 of formula SEQ ID NO:45, 46 or 57, in which the residue corresponding to X145 and X153 in the domain are as described herein. In some embodiments, the region or domain corresponding to residues 90-211 can have additionally 1-2, 1-3, 1-4, 1-5, 1-6, 1-7, 1-8, 1-9, 1-10, 1-11, 1-12, 1-14, 1-15, 1-16, 1-18, or 1-20 residue differences at other amino acid residues as compared to the domain of a reference sequence based on SEQ ID NO:2, 4, or 48. In some embodiments, the number of differences can be 1, 2, 3, 4, 5, 6, 7, 8, 9, 10, 11, 12, 14, 15, 16, 18, or about 20 residue differences at other amino acid residues in the domain. In some embodiments, the differences comprise conservative mutations. In some embodiments, the ketoreductase polypeptide comprises an amino acid sequence with at least the preceding features, and wherein the amino acid sequence has at least 85%, 86%, 87%, 88%, 89%, 90%, 91%, 92%, 93%, 94%, 95%, 96%, 97%, 98%, or 99% identity as compared to the amino acid sequence corresponding to residues 90-211 of a reference sequence based on SEQ ID NO:2, 4 or 142 with the specified features at residues corresponding to X145 and/or X153.

In some embodiments, the ketoreductase polypeptides having a domain or region corresponding to residues 90-211 in which the domain or region has the specified features at residues X145 and/or X153, can have one or more of additional features selected from the following: residue corresponding to X96 is an aliphatic, basic, non-polar or polar residue; residue corresponding to X104 is a non-polar or polar residue; residue corresponding to X117 is a non-polar or polar residue; residue corresponding to X147 is an aliphatic, cysteine, or non-polar residue; residue corresponding to X157 is a polar residue; residue corresponding to X177 is an acidic or basic residue; residue corresponding to X178 is a non-polar residue; residue corresponding to X194 is an aliphatic, constrained, or non-polar residue; residue corresponding to X195 is an aliphatic, basic, or non-polar residue; and residue corresponding to X202 is an aliphatic, basic, or non-polar residue. In some embodiments, the region or domain corresponding to residues 90-211 can have additionally 1-2, 1-3, 1-4, 1-5, 1-6, 1-7, 1-8, 1-9, 1-10, 1-11, 1-12, 1-14, 1-15, 1-16, 1-18, or 1-20 residue differences at other amino acid residues as compared to the domain of a reference sequence based on SEQ ID NO:2, 4, or 48. In some embodiments, the number of differences can be 1, 2, 3, 4, 5, 6, 7, 8, 9, 10, 11, 12, 14, 15, 16, 18, or about 20 residue differences at other amino acid residues in the domain. In some embodiments, the differences comprise conservative mutations.

In some embodiments, the ketoreductase polypeptides having a domain or region corresponding to residues 90-211, in which the domain or region has the specified features at residues X145 and/or X153, can have one or more conservative mutations as compared to the amino acid sequence of SEQ ID NO: 2, 4, or 48. Exemplary conservative mutations include amino acid replacements such as, but not limited to: replacement of residue corresponding to X96 (S) with another polar residue, e.g., glutamine; replacement of residue corresponding to X147 (F) with another nonpolar residue, e.g., methionine, leucine, valine, or cysteine; replacement of residue X157 (N) with another polar residue, e.g., threonine; and replacement of residue corresponding to X202 (A) with another aliphatic residue, e.g., valine or isoleucine.

In some embodiments, the ketoreductase polypeptides having a domain or region corresponding to residues 90-211, in which the domain or region has the specified features at residues X145 and/or X153, can have one or more of additional features selected from the following: residue corresponding to X96 is asparagine, glutamine, serine, threonine, lysine, arginine, methionine, glycine, alanine, valine, leucine, isoleucine, particularly alanine, arginine, glutamine, or glycine; residue corresponding to X104 is serine, threonine, glycine, methionine, alanine, valine, leucine, isoleucine, particularly methionine; residue corresponding to X117 is asparagine, glutamine, serine or threonine, particularly serine; residue corresponding to X147 is cysteine, glycine, methionine, alanine, valine, leucine, isoleucine, particularly leucine, methionine or valine; residue corresponding to X157 is asparagine, glutamine, serine or threonine, particularly threonine; residue corresponding to X177 is lysine, arginine, aspartic acid or glutamic acid, particularly glutamic acid; residue corresponding to X178 is glycine, methionine, alanine, valine, leucine, isoleucine, particularly glycine; residue corresponding to X194 is proline, histidine, methionine, glycine, alanine, valine, leucine, or isoleucine, particularly leucine; residue corresponding to X195 is lysine, arginine, glycine, methionine, alanine, valine, leucine, or isoleucine, particularly arginine; and residue corresponding to X202 is lysine, arginine, glycine, methionine, alanine, valine, leucine, isoleucine, particularly valine or isoleucine. In some embodiments, the region or domain corresponding to residues 90-211 can have additionally from about 1-2, 1-3, 1-4, 1-5, 1-6, 1-7, 1-8, 1-9, 1-10, 1-11, 1-12, 1-14, 1-15, 1-16, 1-18, or 1-20 residue differences at other amino acid residues as compared to the domain of a reference sequence based on SEQ ID NO:2, 4, or 48. In some embodiments, the number of differences can be 1, 2, 3, 4, 5, 6, 7, 8, 9, 10, 11, 12, 14, 15, 16, 18, or about 20 residue differences at other amino acid residues in the domain. In some embodiments, the differences comprise conservative mutations.

In some embodiments, an improved ketoreductase comprises an amino acid sequence that has a region or domain based on residues 1-89 of sequence formula of SEQ ID NO:45, 46 or 57. In some embodiments, the residue corresponding to X82 in the domain is a polar residue, particularly serine. In some embodiments, the region or domain corresponding to residues 1-89 can have additionally 1-2, 1-3, 1-4, 1-5, 1-6, 1-7, 1-8, 1-9, 1-10, 1-11, 1-12, 1-14, 1-15, 1-16, 1-18, or 1-20 residue differences at other amino acid residues in the domain as compared to a reference sequence of SEQ ID NO:2, 4 or 48. In some embodiments, the number of difference can be 1, 2, 3, 4, 5, 6, 7, 8, 9, 10, 11, 12, 14, 15, 16, 18, or about 20 residue differences in the domain. In some embodiments, the differences comprise conservative mutations as compared to the reference sequence. In some embodiments, the ketoreductase polypeptide comprises an amino acid sequence that has at least 85%, 86%, 87%, 88%, 89%, 90%, 91%, 92%, 93%, 94%, 95%, 96%, 97%, 98%, or 99% identity as compared to the amino acid sequence corresponding to residues 1-89 of a reference sequence based on SEQ ID NO:2, 4 or 142 with the preceding feature at residue X82.

In some embodiments, the region or domain corresponding to residues 1-89 of the ketoreductase polypeptide can have one or more of the features selected from the following: residue corresponding to X46 is a basic residue; residue corresponding to X72 is an acidic residue; and residue corresponding to X82 is a non-polar or polar residue. In some embodiments, the region or domain corresponding to residues 1-89 can have additionally 1-2, 1-3, 1-4, 1-5, 1-6, 1-7, 1-8, 1-9, 1-10, 1-11, 1-12, 1-14, 1-15, 1-16, 1-18, or 1-20 residue differences at other amino acid residues in the domain as compared to a reference sequence of SEQ ID NO:2, 4 or 48. In some embodiments, the number of difference can be 1, 2, 3, 4, 5, 6, 7, 8, 9, 10, 11, 12, 14, 15, 16, 18, or about 20 residue differences in the domain. In some embodiments, the differences comprise conservative mutations as compared to the reference sequence. In some embodiments, the ketoreductase polypeptide comprises an amino acid sequence that has at least 85%, 86%, 87%, 88%, 89%, 90%, 91%, 92%, 93%, 94%, 95%, 96%, 97%, 98%, or 99% identity as compared to the amino acid sequence corresponding to residues 1-89 of a reference sequence based on SEQ ID NO:2, 4 or 48 with the preceding feature at residue X82.

In some embodiments, the region or domain corresponding to residues 1-89 of the ketoreductase polypeptide can have one or more of the features selected from the following: residue corresponding to X46 is arginine or lysine, particularly arginine; residue corresponding to X72 is aspartic acid or glutamic acid, particularly glutamic acid; and residue corresponding to X82 is glycine, methionine, alanine, valine, leucine, isoleucine, asparagine, glutamine, serine or threonine, particularly serine. In some embodiments, the region or domain corresponding to residues 1-89 can have additionally 1-2, 1-3, 1-4, 1-5, 1-6, 1-7, 1-8, 1-9, 1-10, 1-11, 1-12, 1-14, 1-15, 1-16, 1-18, or 1-20 residue differences at other amino acid residues in the domain as compared to a reference sequence of SEQ ID NO:2, 4 or 48. In some embodiments, the number of difference can be 1, 2, 3, 4, 5, 6, 7, 8, 9, 10, 11, 12, 14, 15, 16, 18, or about 20 residue differences in the domain. In some embodiments, the differences comprise conservative mutations as compared to the reference sequence. In some embodiments, the ketoreductase polypeptide comprises an amino acid sequence that has at least 85%, 86%, 87%, 88%, 89%, 90%, 91%, 92%, 93%, 94%, 95%, 96%, 97%, 98%, or 99% identity as compared to the amino acid sequence corresponding to residues 1-89 of a reference sequence based on SEQ ID NO:2, 4 or 48 with the preceding feature at residue X82.

In some embodiments, the ketoreductase of the disclosure having the specified features and the residue corresponding to X145 and the residue corresponding to X153 can have additionally one or more of the following substitutions such that the polypeptide is further improved (e.g., with respect to stereospecificity, enzymatic activity, and/or thermostability) over the wild-type kefir ketoreductase or another engineered ketoreductase: 46→R; 72→E; 82→S; 96→A, K, Q, R; 104→M; 117→S; 147→C, L, M, V; 157→T; 177→E; 178→G; 194→L; 195→R; 202→I, R, V; 223→V; and 236→R. In some embodiments, the residue corresponding to residue 145 is serine and the residue corresponding to 153 is glutamine and additionally has one or more of the following substitutions such that the polypeptide is further improved over the wild-type kefir ketoreductase or another engineered ketoreductase: 82→S and 96→A.

In some embodiments, the residue corresponding to residue 145 is not serine, and the residue corresponding to residue 153 is a glutamine and the polypeptide additionally has one or more of the following substitutions such that the polypeptide is further improved (e.g., with respect to stereospecificity, enzymatic activity, and/or thermostability) over the wild-type kefir ketoreductase or another engineered ketoreductase: 46→R; 72→E; 82→S; 96→A, K, Q, R; 104→M; 117→S; 147→C, L, M, V; 157→T; 177→E; 178→G; 194→L; 195→R; 202→I, R, V; 223→V; and 236→R. In some embodiments, the residue corresponding to residue 145 is not serine and the residue corresponding to 153 is glutamine and additionally has one or more of the following substitutions such that the polypeptide is further improved over the wild-type kefir ketoreductase or another engineered ketoreductase: 82→S and 96→A.

In some embodiments, the improved engineered ketoreductase enzymes can comprise deletions of the naturally occurring ketoreductase polypeptides as well as deletions of other improved ketoreductase polypeptides. In some embodiments, each of the improved engineered ketoreductase enzymes described herein can comprise deletions of the polypeptides described herein. Thus, for each and every embodiment of the ketoreductase polypeptides of the disclosure, the deletions can comprise one or more amino acids, 2 or more amino acids, 3 or more amino acids, 4 or more amino acids, 5 or more amino acids, 6 or more amino acids, 8 or more amino acids, 10 or more amino acids, 15 or more amino acids, or 20 or more amino acids, up to 10% of the total number of amino acids, up to 10% of the total number of amino acids, up to 20% of the total number of amino acids, or up to 30% of the total number of amino acids of the ketoreductase polypeptides, as long as the functional activity of the ketoreductase activity is maintained. In some embodiments, the deletions can comprise, 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-25, 1-30, 1-35 or about 1-40 amino acid residues.

As described herein, the ketoreductase polypeptides of the disclosure can be in the form of fusion polypeptides in which the ketoreductases polypeptides are fused to other polypeptides, such as antibody tags (e.g., myc epitope) or purifications sequences (e.g., His tags). Thus, the ketoreductase polypeptides can be used with or without fusions to other polypeptides.

The polypeptides described herein are not restricted to the genetically encoded amino acids. In addition to the genetically encoded amino acids, the polypeptides described herein may be comprised, either in whole or in part, of naturally-occurring and/or synthetic non-encoded amino acids. Certain commonly encountered non-encoded amino acids of which the polypeptides described herein may be comprised include, but are not limited to: the D-enantiomers of the genetically-encoded amino acids; 2,3-diaminopropionic acid (Dpr); α-aminoisobutyric acid (Aib); ε-aminohexanoic acid (Aha); δ-aminovaleric acid (Ava); N-methylglycine or sarcosine (MeGly or Sar); ornithine (Orn); citrulline (Cit); t-butylalanine (Bua); t-butylglycine (Bug); N-methylisoleucine (MeIle); phenylglycine (Phg); cyclohexylalanine (Cha); norleucine (Nle); naphthylalanine (Nal); 2-chlorophenylalanine (Ocf); 3-chlorophenylalanine (Mcf); 4-chlorophenylalanine (Pcf); 2-fluorophenylalanine (Off); 3-fluorophenylalanine (Mff); 4-fluorophenylalanine (Pff); 2-bromophenylalanine (Obf); 3-bromophenylalanine (Mbf); 4-bromophenylalanine (Pbf); 2-methylphenylalanine (Omf); 3-methylphenylalanine (Mmf); 4-methylphenylalanine (Pmf); 2-nitrophenylalanine (Onf); 3-nitrophenylalanine (Mnf); 4-nitrophenylalanine (Pnf); 2-cyanophenylalanine (Ocf); 3-cyanophenylalanine (Mcf); 4-cyanophenylalanine (Pcf); 2-trifluoromethylphenylalanine (Otf); 3-trifluoromethylphenylalanine (Mtf); 4-trifluoromethylphenylalanine (Ptf); 4-aminophenylalanine (Paf); 4-iodophenylalanine (Pif); 4-aminomethylphenylalanine (Pamf); 2,4-dichlorophenylalanine (Opef); 3,4-dichlorophenylalanine (Mpcf); 2,4-difluorophenylalanine (Opff); 3,4-difluorophenylalanine (Mpff); pyrid-2-ylalanine (2pAla); pyrid-3-ylalanine (3pAla); pyrid-4-ylalanine (4pAla); naphth-1-ylalanine (1nAla); naphth-2-ylalanine (2nAla); thiazolylalanine (taAla); benzothienylalanine (bAla); thienylalanine (tAla); furylalanine (fAla); homophenylalanine (hPhe); homotyrosine (hTyr); homotryptophan (hTrp); pentafluorophenylalanine (5ff); styrylkalanine (sAla); authrylalanine (aAla); 3,3-diphenylalanine (Dfa); 3-amino-5-phenypentanoic acid (Afp); penicillamine (Pen); 1,2,3,4-tetrahydroisoquinoline-3-carboxylic acid (Tic); β-2-thienylalanine (Thi); methionine sulfoxide (Mso); N(w)-nitroarginine (nArg); homolysine (hLys); phosphonomethylphenylalanine (pmPhe); phosphoserine (pSer); phosphothreonine (pThr); homoaspartic acid (hAsp); homoglutamic acid (hGlu); 1-aminocyclopent-(2 or 3)-ene-4 carboxylic acid; pipecolic acid (PA), azetidine-3-carboxylic acid (ACA); 1-aminocyclopentane-3-carboxylic acid; allylglycine (aOly); propargylglycine (pgGly); homoalanine (hAla); norvaline (nVal); homoleucine (hLeu), homovaline (hVal); homoisoleucine (hIle); homoarginine (hArg); N-acetyl lysine (AcLys); 2,4-diaminobutyric acid (Dbu); 2,3-diaminobutyric acid (Dab); N-methylvaline (MeVal); homocysteine (hCys); homoserine (hSer); hydroxyproline (Hyp) and homoproline (hPro). Additional non-encoded amino acids of which the polypeptides described herein may be comprised will be apparent to those of skill in the art (see, e.g., the various amino acids provided in Fasman, 1989, CRC Practical Handbook of Biochemistry and Molecular Biology, CRC Press, Boca Raton, Fla., at pp. 3-70 and the references cited therein, all of which are incorporated by reference). These amino acids may be in either the L- or D-configuration.

Those of skill in the art will recognize that amino acids or residues bearing side chain protecting groups may also comprise the polypeptides described herein. Non-limiting examples of such protected amino acids, which in this case belong to the aromatic category, include (protecting groups listed in parentheses), but are not limited to: Arg(tos), Cys (methylbenzyl), Cys (nitropyridinesulfenyl), Glu(δ-benzylester), Gln(xanthyl), Asn(N-δ-xanthyl), His(bom), His(benzyl), His(tos), Lys(fmoc), Lys(tos), Ser(O-benzyl), Thr (O-benzyl) and Tyr(O-benzyl).

Non-encoding amino acids that are conformationally constrained of which the polypeptides described herein may be composed include, but are not limited to, N-methyl amino acids (L-configuration); 1-aminocyclopent-(2 or 3)-ene-4-carboxylic acid; pipecolic acid; azetidine-3-carboxylic acid; homoproline (hPro); and 1-aminocyclopentane-3-carboxylic acid.

As described above the various modifications introduced into the naturally occurring polypeptide to generate an engineered ketoreductase enzyme can be targeted to a specific property of the enzyme.

7.3 Polynucleotides Encoding Engineered Ketoreductases

In another aspect, the present disclosure provides polynucleotides encoding the engineered ketoreductase enzymes. The polynucleotides may be operatively linked to one or more heterologous regulatory sequences that control gene expression to create a recombinant polynucleotide capable of expressing the polypeptide. Expression constructs containing a heterologous polynucleotide encoding the engineered ketoreductase can be introduced into appropriate host cells to express the corresponding ketoreductase polypeptide.

Because of the knowledge of the codons corresponding to the various amino acids, availability of a protein sequence provides a description of all the polynucleotides capable of encoding the subject. The degeneracy of the genetic code, where the same amino acids are encoded by alternative or synonymous codons allows an extremely large number of nucleic acids to be made, all of which encode the improved ketoreductase enzymes disclosed herein. Thus, having identified a particular amino acid sequence, those skilled in the art could make any number of different nucleic acids by simply modifying the sequence of one or more codons in a way which does not change the amino acid sequence of the protein. In this regard, the present disclosure specifically contemplates each and every possible variation of polynucleotides that could be made by selecting combinations based on the possible codon choices, and all such variations are to be considered specifically disclosed for any polypeptide disclosed herein, including the amino acid sequences presented in Table 1.

In some embodiments, the polynucleotide comprises a nucleotide sequence encoding a ketoreductase polypeptide with an amino acid sequence that has at least about 80% or more sequence identity, at least 85%, 86%, 87%, 88%, 89%, 90%, 91%, 92%, 93%, 94%, 95%, 96%, 97%, 98%, or 99% identity, or more sequence identity to any of the reference engineered ketoreductase polypeptides described herein, where the ketoreductase polypeptide comprises an amino acid sequence that has at least the following features: residue corresponding to X145 is a polar residue, and residue corresponding to X153 is a polar residue. In some embodiments, the polynucleotide comprises a nucleotide sequence encoding a ketoreductase polypeptide with the above levels of sequence identities having at least, as compared to the amino acid sequence of SEQ ID NO:2, 4, or 48, the following features: the residue corresponding to X145 is a serine, and the residue corresponding to X153 is a glutamine. In some embodiments, the polynucleotide comprises a nucleotide sequence encoding a ketoreductase polypeptide with the above levels of sequence identities having at least, as compared to the amino acid sequence of SEQ ID NO:2, 4, or 48, the following features: the residue corresponding to residue 153 is a polar residue and the residue corresponding to residue 145 is not a polar residue. In some embodiments, the polynucleotide comprises a nucleotide sequence encoding a ketoreductase polypeptide with the above levels of sequence identities having at least, as compared to the amino acid sequence of SEQ ID NO:2, 4, or 48, the following features: the residue corresponding to residue 153 is a glutamine and the residue corresponding to residue 145 is not serine. In some embodiments, the polynucleotides encode an engineered ketoreductase polypeptide comprising an amino acid sequence selected from SEQ ID NO:6, 8, 10, 12, 14, 16, 18, 20, 22, 24, 26, 28, 30, 32, 34, 36, 38, 40, 42, and 44.

In various embodiments, the codons are preferably selected to fit the host cell in which the protein is being produced. For example, preferred codons used in bacteria are used to express the gene in bacteria; preferred codons used in yeast are used for expression in yeast; and preferred codons used in mammals are used for expression in mammalian cells. By way of example, the polynucleotide of SEQ ID NO:3 has been codon optimized for expression in *E. coli*, but otherwise encodes the naturally occurring ketoreductase of *Lactobacillus kefir*.

In some embodiments, all codons need not be replaced to optimize the codon usage of the ketoreductases since the natural sequence will comprise preferred codons and because use of preferred codons may not be required for all amino acid residues. Consequently, codon optimized polynucleotides encoding the ketoreductase enzymes may contain preferred codons at about 40%, 50%, 60%, 70%, 80%, or greater than 90% of codon positions of the full length coding region.

In some embodiments, the polynucleotides encoding the engineered ketoreductases are selected from SEQ ID NO:5, 7, 9, 11, 13, 15, 17, 19, 21, 23, 25, 27, 29, 31, 33, 35, 37, 39, 41, and 43. In some embodiments, the polynucleotides encoding the engineered ketoreductases are capable of hybridizing under highly stringent conditions to a polynucleotide comprising SEQ ID NO:5, 7, 9, 11, 13, 15, 17, 19, 21, 23, 25, 27, 29, 31, 33, 35, 37, 39, 41, and 43. In some embodiments, the scope of the polynucleotides of the disclosure specifically does not include SEQ ID NO:15 and SEQ ID NO:41.

These polynucleotides encode some of the polypeptides represented by the amino acid sequences listed in Table 2, which were derived by subjecting the *E. coli* codon optimized *L. kefir*, a codon optimized *L. brevis* gene, a codon optimized *L. minor* gene or an engineered ketoreductase gene therefrom to directed gene evolution techniques described herein. In some embodiments, an engineered ketoreductase gene can be derived from a wild-type *L. kefir*, *L. brevis*, or *L. minor* gene.

In other embodiments, the polynucleotides comprise polynucleotides that encode the polypeptides described herein but have about 80% or more sequence identity, about 85% or more sequence identity, about 90% or more sequence identity, about 95% or more sequence identity, about 98% or more sequence identity, or 99% or more sequence identity at the nucleotide level to a reference polynucleotide encoding an engineered ketoreductase. In some embodiments, the reference polynucleotide is selected from polynucleotide sequences represented by SEQ ID NO:5, 7, 9, 11, 13, 15, 17, 19, 21, 23, 25, 27, 29, 31, 33, 35, 37, 39, 41, and 43.

An isolated polynucleotide encoding an improved ketoreductase polypeptide may be manipulated in a variety of ways to provide for expression of the polypeptide. Manipulation of the isolated polynucleotide prior to its insertion into a vector may be desirable or necessary depending on the expression vector. The techniques for modifying polynucleotides and nucleic acid sequences utilizing recombinant DNA methods are well known in the art. Guidance is provided in Sambrook et al., 2001, Molecular Cloning: A Laboratory Manual, 3$^{rd}$ Ed., Cold Spring Harbor Laboratory Press; and Current Protocols in Molecular Biology, Ausubel. F. ed., Greene Pub. Associates, 1998, updates to 2006.

For bacterial host cells, suitable promoters for directing transcription of the nucleic acid constructs of the present disclosure, include the promoters obtained from the *E. coli* lac operon, *Streptomyces coelicolor* agarase gene (dagA), *Bacillus subtilis* levansucrase gene (sacB), *Bacillus licheniformis* alpha-amylase gene (amyL), *Bacillus stearothermophilus* maltogenic amylase gene (amyM), *Bacillus amyloliquefaciens* alpha-amylase gene (amyQ), *Bacillus licheniformis* penicillinase gene (penP), *Bacillus subtilis* xylA and xylB genes, and prokaryotic beta-lactamase gene (Villa-Kamaroff et al., 1978, Proc. Natl. Acad. Sci. USA 75: 3727-3731), as well as the tac promoter (DeBoer et al., 1983, Proc. Natl. Acad. Sci. USA 80: 21-25). Further promoters are described in "Useful proteins from recombinant bacteria" in Scientific American, 1980, 242:74-94; and in Sambrook et al., supra.

For filamentous fungal host cells, suitable promoters for directing the transcription of the nucleic acid constructs of the present disclosure include promoters obtained from the genes for *Aspergillus oryzae* TAKA amylase, *Rhizomucor miehei* aspartic proteinase, *Aspergillus niger* neutral alpha-amylase, *Aspergillus niger* acid stable alpha-amylase, *Aspergillus* niger or *Aspergillus awamori* glucoamylase (glaA), *Rhizomucor miehei* lipase, *Aspergillus oryzae* alkaline protease, *Aspergillus oryzae* triose phosphate isomerase, *Aspergillus nidulans* acetamidase, and *Fusarium oxysporum* trypsin-like protease (WO 96/00787), as well as the NA2-tpi promoter (a hybrid of the promoters from the genes for *Aspergillus niger* neutral alpha-amylase and *Aspergillus oryzae* triose phosphate isomerase), and mutant, truncated, and hybrid promoters thereof.

In a yeast host, useful promoters can be from the genes for *Saccharomyces cerevisiae* enolase (ENO-1), *Saccharomyces cerevisiae* galactokinase (GAL1), *Saccharomyces cerevisiae* alcohol dehydrogenase/glyceraldehyde-3-phosphate dehydrogenase (ADH2/GAP), and *Saccharomyces cerevisiae* 3-phosphoglycerate kinase. Other useful promoters for yeast host cells are described by Romanos et al., 1992, Yeast 8:423-488.

The control sequence may also be a suitable transcription terminator sequence, a sequence recognized by a host cell to terminate transcription. The terminator sequence is operably linked to the 3' terminus of the nucleic acid sequence encoding the polypeptide. Any terminator which is functional in the host cell of choice may be used in the present invention.

For example, exemplary transcription terminators for filamentous fungal host cells can be obtained from the genes for *Aspergillus oryzae* TAKA amylase, *Aspergillus niger* glucoamylase, *Aspergillus nidulans* anthranilate synthase, *Aspergillus niger* alpha-glucosidase, and *Fusarium oxysporum* trypsin-like protease.

Exemplary terminators for yeast host cells can be obtained from the genes for *Saccharomyces cerevisiae* enolase, *Saccharomyces cerevisiae* cytochrome C(CYC1), and *Saccharomyces cerevisiae* glyceraldehyde-3-phosphate dehydrogenase. Other useful terminators for yeast host cells are described by Romanos et al., 1992, supra.

The control sequence may also be a suitable leader sequence, a nontranslated region of an mRNA that is important for translation by the host cell. The leader sequence is operably linked to the 5' terminus of the nucleic acid sequence encoding the polypeptide. Any leader sequence that is functional in the host cell of choice may be used. Exemplary leaders for filamentous fungal host cells are obtained from the genes for *Aspergillus oryzae* TAKA amylase and *Aspergillus nidulans* triose phosphate isomerase. Suitable leaders for yeast host cells are obtained from the genes for *Saccharomyces cerevisiae* enolase (ENO-1), *Saccharomyces cerevisiae* 3-phosphoglycerate kinase, *Saccharomyces cerevisiae* alpha-factor, and *Saccharomyces cerevisiae* alcohol dehydrogenase/glyceraldehyde-3-phosphate dehydrogenase (ADH2/GAP).

The control sequence may also be a polyadenylation sequence, a sequence operably linked to the 3' terminus of the nucleic acid sequence and which, when transcribed, is recognized by the host cell as a signal to add polyadenosine residues to transcribed mRNA. Any polyadenylation sequence which is functional in the host cell of choice may be used in the present invention. Exemplary polyadenylation sequences for filamentous fungal host cells can be from the genes for *Aspergillus oryzae* TAKA amylase, *Aspergillus niger* glucoamylase, *Aspergillus nidulans* anthranilate synthase, *Fusarium oxysporum* trypsin-like protease, and *Aspergillus niger* alpha-glucosidase. Useful polyadenylation sequences for yeast host cells are described by Guo and Sherman, 1995, Mol Cell Bio 15:5983-5990.

The control sequence may also be a signal peptide coding region that codes for an amino acid sequence linked to the amino terminus of a polypeptide and directs the encoded polypeptide into the cell's secretory pathway. The 5' end of the coding sequence of the nucleic acid sequence may inherently contain a signal peptide coding region naturally linked in translation reading frame with the segment of the coding region that encodes the secreted polypeptide. Alternatively, the 5' end of the coding sequence may contain a signal peptide coding region that is foreign to the coding sequence. The foreign signal peptide coding region may be required where the coding sequence does not naturally contain a signal peptide coding region.

Alternatively, the foreign signal peptide coding region may simply replace the natural signal peptide coding region in order to enhance secretion of the polypeptide. However, any signal peptide coding region which directs the expressed polypeptide into the secretory pathway of a host cell of choice may be used in the present invention.

Effective signal peptide coding regions for bacterial host cells are the signal peptide coding regions obtained from the genes for *Bacillus* NC1B 11837 maltogenic amylase, *Bacillus stearothermophilus* alpha-amylase, *Bacillus licheniformis* subtilisin, *Bacillus licheniformis* beta-lactamase, *Bacillus stearothermophilus* neutral proteases (nprT, nprS, nprM), and *Bacillus subtilis* prsA. Further signal peptides are described by Simonen and Palva, 1993, Microbiol Rev 57: 109-137.

Effective signal peptide coding regions for filamentous fungal host cells can be the signal peptide coding regions obtained from the genes for *Aspergillus oryzae* TAKA amylase, *Aspergillus niger* neutral amylase, *Aspergillus niger* glucoamylase, *Rhizomucor miehei* aspartic proteinase, *Humicola insolens* cellulase, and *Humicola lanuginosa* lipase.

Useful signal peptides for yeast host cells can be from the genes for *Saccharomyces cerevisiae* alpha-factor and *Saccharomyces cerevisiae* invertase. Other useful signal peptide coding regions are described by Romanos et al., 1992, supra.

The control sequence may also be a propeptide coding region that codes for an amino acid sequence positioned at the amino terminus of a polypeptide. The resultant polypeptide is known as a proenzyme or propolypeptide (or a zymogen in some cases). A propolypeptide is generally inactive and can be converted to a mature active polypeptide by catalytic or autocatalytic cleavage of the propeptide from the propolypeptide. The propeptide coding region may be obtained from the genes for *Bacillus subtilis* alkaline protease (aprE), *Bacillus subtilis* neutral protease (nprT), *Saccharomyces cerevisiae* alpha-factor, *Rhizomucor miehei* aspartic proteinase, and *Myceliophthora thermophila* lactase (WO 95/33836).

Where both signal peptide and propeptide regions are present at the amino terminus of a polypeptide, the propeptide region is positioned next to the amino terminus of a polypeptide and the signal peptide region is positioned next to the amino terminus of the propeptide region.

It may also be desirable to add regulatory sequences, which allow the regulation of the expression of the polypeptide relative to the growth of the host cell. Examples of regulatory systems are those which cause the expression of the gene to be turned on or off in response to a chemical or physical stimulus, including the presence of a regulatory compound. In prokaryotic host cells, suitable regulatory sequences include the lac, tac, and trp operator systems. In yeast host cells, suitable regulatory systems include, as examples, the ADH2 system or GAL1 system. In filamentous fungi, suitable regulatory sequences include the TAKA alpha-amylase promoter, *Aspergillus niger* glucoamylase promoter, and *Aspergillus oryzae* glucoamylase promoter.

Other examples of regulatory sequences are those which allow for gene amplification. In eukaryotic systems, these include the dihydrofolate reductase gene, which is amplified in the presence of methotrexate, and the metallothionein genes, which are amplified with heavy metals. In these cases, the nucleic acid sequence encoding the KRED polypeptide of the present invention would be operably linked with the regulatory sequence.

Thus, in another embodiment, the present disclosure is also directed to a recombinant expression vector comprising a polynucleotide encoding an engineered ketoreductase polypeptide or a variant thereof, and one or more expression regulating regions such as a promoter and a terminator, a replication origin, etc., depending on the type of hosts into which they are to be introduced. The various nucleic acid and control sequences described above may be joined together to produce a recombinant expression vector which may include one or more convenient restriction sites to allow for insertion or substitution of the nucleic acid sequence encoding the polypeptide at such sites. Alternatively, the nucleic acid sequence of the present disclosure may be expressed by inserting the nucleic acid sequence or a nucleic acid construct comprising the sequence into an appropriate vector for expression. In creating the expression vector, the coding sequence is located in the vector so that the coding sequence is operably linked with the appropriate control sequences for expression.

The recombinant expression vector may be any vector (e.g., a plasmid or virus), which can be conveniently subjected to recombinant DNA procedures and can bring about the expression of the polynucleotide sequence. The choice of the vector will typically depend on the compatibility of the vector with the host cell into which the vector is to be introduced. The vectors may be linear or closed circular plasmids.

The expression vector may be an autonomously replicating vector, i.e., a vector that exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one which, when introduced into the host cell, is integrated into the genome and replicated together with the chromosome(s) into which it has been integrated. Furthermore, a single vector or plasmid or two or more vectors or plasmids which together contain the total DNA to be introduced into the genome of the host cell, or a transposon may be used.

The expression vector of the present invention preferably contains one or more selectable markers, which permit easy selection of transformed cells. A selectable marker is a gene the product of which provides for biocide or viral resistance, resistance to heavy metals, prototrophy to auxotrophs, and the like. Examples of bacterial selectable markers are the dal genes from *Bacillus subtilis* or *Bacillus licheniformis*, or markers, which confer antibiotic resistance such as ampicillin, kanamycin, chloramphenicol (Example 1) or tetracycline resistance. Suitable markers for yeast host cells are ADE2, HIS3, LEU2, LYS2, MET3, TRP1, and URA3.

Selectable markers for use in a filamentous fungal host cell include, but are not limited to, amdS (acetamidase), argB (ornithine carbamoyltransferase), bar (phosphinothricin acetyltransferase), hph (hygromycin phosphotransferase), niaD (nitrate reductase), pyrG (orotidine-5'-phosphate decarboxylase), sC (sulfate adenyltransferase), and trpC (anthranilate synthase), as well as equivalents thereof. Embodiments for use in an *Aspergillus* cell include the amdS and pyrG genes of *Aspergillus nidulans* or *Aspergillus oryzae* and the bar gene of *Streptomyces hygroscopicus*.

The expression vectors of the present invention preferably contain an element(s) that permits integration of the vector into the host cell's genome or autonomous replication of the vector in the cell independent of the genome. For integration into the host cell genome, the vector may rely on the nucleic acid sequence encoding the polypeptide or any other element of the vector for integration of the vector into the genome by homologous or nonhomologous recombination.

Alternatively, the expression vector may contain additional nucleic acid sequences for directing integration by homologous recombination into the genome of the host cell. The additional nucleic acid sequences enable the vector to be integrated into the host cell genome at a precise location(s) in the chromosome(s). To increase the likelihood of integration at a precise location, the integrational elements should preferably contain a sufficient number of nucleic acids, such as 100 to 10,000 base pairs, preferably 400 to 10,000 base pairs, and most preferably 800 to 10,000 base pairs, which are highly homologous with the corresponding target sequence to enhance the probability of homologous recombination. The integrational elements may be any sequence that is homologous with the target sequence in the genome of the host cell. Furthermore, the integrational elements may be non-encoding or encoding nucleic acid sequences. On the other hand, the vector may be integrated into the genome of the host cell by non-homologous recombination.

For autonomous replication, the vector may further comprise an origin of replication enabling the vector to replicate autonomously in the host cell in question. Examples of bacterial origins of replication are P15A ori (as shown in the plasmid of FIG. 5) or the origins of replication of plasmids pBR322, pUC19, pACYC177 (which plasmid has the P15A ori), or pACYC184 permitting replication in *E. coli*, and pUB110, pE194, pTA1060, or pAMf31 permitting replication in *Bacillus*. Examples of origins of replication for use in a yeast host cell are the 2 micron origin of replication, ARS1, ARS4, the combination of ARS1 and CEN3, and the combination of ARS4 and CEN6. The origin of replication may be one having a mutation which makes it's functioning temperature-sensitive in the host cell (see, e.g., Ehrlich, 1978, Proc Natl Acad. Sci. USA 75:1433).

More than one copy of a nucleic acid sequence of the present invention may be inserted into the host cell to increase production of the gene product. An increase in the copy number of the nucleic acid sequence can be obtained by integrating at least one additional copy of the sequence into the host cell genome or by including an amplifiable selectable marker gene with the nucleic acid sequence where cells containing amplified copies of the selectable marker gene, and thereby additional copies of the nucleic acid sequence, can be selected for by cultivating the cells in the presence of the appropriate selectable agent.

Many of the expression vectors for use in the present invention are commercially available. Suitable commercial expression vectors include p3xFLAG™ expression vectors from Sigma-Aldrich Chemicals, St. Louis Mo., which includes a CMV promoter and hGH polyadenylation site for expression in mammalian host cells and a pBR322 origin of replication and ampicillin resistance markers for amplification in *E. coli*. Other suitable expression vectors are pBluescriptII SK(−) and pBK-CMV, which are commercially available from Stratagene, LaJolla Calif., and plasmids which are derived from pBR322 (Gibco BRL), pUC (Gibco BRL), pREP4, pCEP4 (Invitrogen) or pPoly (Lathe et al., 1987, Gene 57:193-201).

7.4 Host Cells for Expression of Ketoreductase Polypeptides

In another aspect, the present disclosure provides a host cell comprising a polynucleotide encoding an improved ketoreductase polypeptide of the present disclosure, the polynucleotide being operatively linked to one or more control sequences for expression of the ketoreductase enzyme in the host cell. Host cells for use in expressing the KRED polypeptides encoded by the expression vectors of the present invention are well known in the art and include but are not limited to, bacterial cells, such as *E. coli, Lactobacillus kefir, Lactobacillus brevis, Lactobacillus minor, Streptomyces* and *Salmonella typhimurium* cells; fungal cells, such as yeast cells (e.g., *Saccharomyces cerevisiae* or *Pichia pastoris* (ATCC Accession No. 201178)); insect cells such as *Drosophila* S2 and *Spodoptera* Sf9 cells; animal cells such as CHO, COS, BHK, 293, and Bowes melanoma cells; and plant cells. Appropriate culture mediums and growth conditions for the above-described host cells are well known in the art.

Polynucleotides for expression of the ketoreductase may be introduced into cells by various methods known in the art. Techniques include among others, electroporation, biolistic particle bombardment, liposome mediated transfection, calcium chloride transfection, and protoplast fusion. Various methods for introducing polynucleotides into cells will be apparent to the skilled artisan.

An exemplary host cell is *Escherichia coli* W3110. The expression vector was created by operatively linking a polynucleotide encoding an improved ketoreductase into the plasmid pCK110900 (see, US application publication 20040137585) operatively linked to the lac promoter under control of the lad repressor. The expression vector also contained the P15a origin of replication and the chloramphenicol resistance gene. Cells containing the subject polynucleotide in *Escherichia coli* W3110 were isolated by subjecting the cells to chloramphenicol selection.

7.5 Methods of Generating Engineered Ketoreductase Polypeptides

In some embodiments, to make the improved KRED polynucleotides and polypeptides of the present disclosure, the naturally-occurring ketoreductase enzyme that catalyzes the reduction reaction is obtained (or derived) from *Lactobacillus kefir, Lactobacillus brevis*, or *Lactobacillus minor*. In some embodiments, the parent polynucleotide sequence is codon optimized to enhance expression of the ketoreductase in a specified host cell. As an illustration, the parental polynucleotide sequence encoding the wild-type KRED polypeptide of *Lactobacillus kefir* was constructed from oligonucleotides prepared based upon the known polypeptide sequence of *Lactobacillus kefir* KRED sequence available in Genbank database (Genbank accession no. AAP94029 GI:33112056). The parental polynucleotide sequence, designated as SEQ ID NO:3, was codon optimized for expression in *E. coli* and the codon-optimized polynucleotide cloned into an expression vector, placing the expression of the ketoreductase gene under the control of the lac promoter and lad repressor gene. Clones expressing the active ketoreductase in *E. coli* were identified and the genes sequenced to confirm their identity. The sequence designated (SEQ ID NO:3) was the parent sequence utilized as the starting point for most experiments and library construction of engineered ketoreductases evolved from the *Lactobacillus kefir* ketoreductase.

The engineered ketoreductases can be obtained by subjecting the polynucleotide encoding the naturally occurring ketoreductase to mutagenesis and/or directed evolution methods, as discussed above. An exemplary directed evolution technique is mutagenesis and/or DNA shuffling as described in Stemmer, 1994, *Proc Natl Acad Sci USA* 91:10747-10751; WO 95/22625; WO 97/0078; WO 97/35966; WO 98/27230; WO 00/42651; WO 01/75767 and U.S. Pat. No. 6,537,746. Other directed evolution procedures that can be used include, among others, staggered extension process (StEP), in vitro recombination (Zhao et al., 1998, *Nat. Biotechnol.* 16:258-261), mutagenic PCR (Caldwell et al., 1994, PCR Methods Appl. 3:S136-S140), and cassette mutagenesis (Black et al., 1996, *Proc Natl Acad Sci USA* 93:3525-3529).

The clones obtained following mutagenesis treatment are screened for engineered ketoreductases having a desired improved enzyme property. Measuring enzyme activity from the expression libraries can be performed using the standard biochemistry technique of monitoring the rate of decrease (via a decrease in absorbance or fluorescence) of NADH or NADPH concentration, as it is converted into $NAD^+$ or $NADP^+$. (For example, see Example 7) In this reaction, the NADH or NADPH is consumed (oxidized) by the ketoreductase as the ketoreductase reduces a ketone substrate to the corresponding hydroxyl group. The rate of decrease of NADH or NADPH concentration, as measured by the decrease in absorbance or fluorescence, per unit time indicates the relative (enzymatic) activity of the KRED polypeptide in a fixed amount of the lysate (or a lyophilized powder made therefrom). Where the improved enzyme property desired is thermal stability, enzyme activity may be measured after subjecting the enzyme preparations to a defined temperature and measuring the amount of enzyme activity remaining after heat treatments. Clones containing a polynucleotide encoding a ketoreductase are then isolated, sequenced to identify the nucleotide sequence changes (if any), and used to express the enzyme in a host cell.

Where the sequence of the engineered polypeptide is known, the polynucleotides encoding the enzyme can be prepared by standard solid-phase methods, according to known synthetic methods. In some embodiments, fragments of up to about 100 bases can be individually synthesized, then joined (e.g., by enzymatic or chemical litigation methods, or polymerase mediated methods) to form any desired continuous sequence. For example, polynucleotides and oligonucleotides of the invention can be prepared by chemical synthesis using, e.g., the classical phosphoramidite method described by Beaucage et al., 1981, Tet Lett 22:1859-69, or the method described by Matthes et al., 1984, EMBO J. 3:801-05, e.g., as it is typically practiced in automated synthetic methods. According to the phosphoramidite method, oligonucleotides are synthesized, e.g., in an automatic DNA synthesizer, purified, annealed, ligated and cloned in appropriate vectors. In addition, essentially any nucleic acid can be obtained from any of a variety of commercial sources, such as The Midland Certified Reagent Company, Midland, Tex., The Great American Gene Company, Ramona, Calif., ExpressGen Inc. Chicago, Ill., Operon Technologies Inc., Alameda, Calif., and many others.

Engineered ketoreductase enzymes expressed in a host cell can be recovered from the cells and or the culture medium using any one or more of the well known techniques for protein purification, including, among others, lysozyme treatment, sonication, filtration, salting-out, ultra-centrifugation, and chromatography. Suitable solutions for lysing and the high efficiency extraction of proteins from bacteria, such as *E. coli*, are commercially available under the trade name CelLytic B™ from Sigma-Aldrich of St. Louis Mo.

Chromatographic techniques for isolation of the ketoreductase polypeptide include, among others, reverse phase chromatography high performance liquid chromatography, ion exchange chromatography, gel electrophoresis, and affinity chromatography. Conditions for purifying a particular enzyme will depend, in part, on factors such as net charge, hydrophobicity, hydrophilicity, molecular weight, molecular shape, etc., and will be apparent to those having skill in the art.

In some embodiments, affinity techniques may be used to isolate the improved ketoreductase enzymes. For affinity chromatography purification, any antibody which specifically binds the ketoreductase polypeptide may be used. For the production of antibodies, various host animals, including but not limited to rabbits, mice, rats, etc., may be immunized by injection with a polypeptide of the disclosure. The polypeptide may be attached to a suitable carrier, such as BSA, by means of a side chain functional group or linkers attached to a side chain functional group. Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanin, dinitrophenol, and potentially useful human adjuvants such as BCG (bacilli Calmette Guerin) and *Corynebacterium parvum*.

7.6 Methods of Using the Engineered Ketoreductase Enzymes and Compounds Prepared Therewith The ketoreductase enzymes described herein can catalyze the enantiospecific reduction of the substrate compound of structural formula (I), (R)-2-methylpentanal, such as in a mixture with (S)-2-methylpentanal to the chiral product compound of structural formula (II), (R)-2-methylpentanol, as illustrated below.

In some embodiments, the invention provides a method for reducing a (R)-2-alkyl substituted aldehyde compound in a mixture with the (S)-2-alkyl substituted aldehyde compound such as contacting or incubating 2-methylpentanal with a ketoreductase polypeptide disclosed herein under suitable reaction conditions for producing a chiral 2-methyl substituted alcohol such as (R)-2-methylpentanol, as illustrated in the reaction below

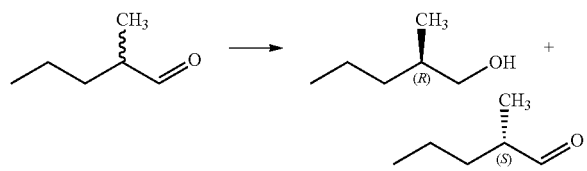

As noted above, any of the ketoreductase polypeptides described herein, including those exemplified in Table 2, can be used in the methods. For example, in some embodiments, the methods can use ketoreductase polypeptides having, as compared to the amino acid sequence of SEQ ID NO:2, 4, or 48, the following features: residue corresponding to residue X145 is a polar residue, and residue corresponding to residue X153 is a polar residue. In some embodiments, the ketoreductase polypeptides have, as compared to SEQ ID NO:2, 4, or 48, the following features: residue corresponding to residue X145 is serine, and residue corresponding to residue X153 is glutamine. In some embodiments, the ketoreductase polypeptides have, as compared to SEQ ID NO:2, 4, or 48, the following features: residue corresponding to residue X145 is not a polar residue, and residue corresponding to residue X153 is a polar amino acid. In some embodiments, the ketoreductase polypeptides have, as compared to SEQ ID NO:2, 4, or 48, the following features: residue corresponding to residue X145 is not serine, and residue corresponding to residue X153 is a glutamine.

As will be appreciated by the skilled artisan, the ketoreductase polypeptides with the preceding features can have one or more additional differences at other amino acid residue positions, as described for the ketoreductase polypeptides described herein. For example, for ketoreductase polypeptides having the preceding features, the polypeptide can have an amino acid sequence having one or more of the following features: residue corresponding to X46 is a basic residue; residue corresponding to X72 is an acidic residue; residue corresponding to X82 is a polar residue; residue corresponding to X96 is an aliphatic, basic, non-polar or polar residue; residue corresponding to X104 is a non-polar or polar residue; residue corresponding to X117 is a non-polar or polar residue; residue corresponding to X147 is an aliphatic, cysteine, or non-polar residue; residue corresponding to X157 is a polar residue; residue corresponding to X177 is a basic or acidic residue; residue corresponding to X178 is a non-polar residue; residue corresponding to X194 is an aliphatic, constrained, or non-polar residue; residue corresponding to X195 is an aliphatic, basic, or non-polar residue; residue corresponding to X202 is an aliphatic, basic, or non-polar residue; residue corresponding to X223 is an aliphatic or non-polar residue; residue corresponding to X236 is a basic residue. In some embodiments, the polypeptides comprising an amino acid sequence that corresponds to the sequence formulas as laid out in SEQ ID NO:45, SEQ ID NO:46, or SEQ ID NO:57 (or region thereof) can optionally have one or more of the residues not specified in the forgoing to be conservatively mutated.

In some embodiments of the method, the product has greater than about 98% stereomeric excess of the (R)-2-alkyl substituted aldehyde, wherein the ketoreducase polypeptide comprises an amino acid sequence corresponding to SEQ ID NO:24, 26, 28, and 44. In some embodiments of the method, the product is obtained with greater than about 99% stereomeric excess, wherein the ketoreducase polypeptide comprises an amino acid sequence corresponding to SEQ ID NO:24. In some embodiments of the method, at least about 45% of a racemic substrate mixture is reduced to the product in less than 24, 23, 22, 21, 20, 19, 18, 17, 16, 15, 14, 13, 12, 11, 10, 9, 8, or 7 hours when the method is conducted with greater than or equal to 220 g/L substrate and less than or equal to 2 g/L ketoreductase enzyme but more than 0% enzyme, wherein the ketoreductase polypeptide comprises an amino acid sequence corresponding to SEQ ID NO:24, 26, 28, and 44.

As is known by those of skill in the art, ketoreductase-catalyzed reduction reactions typically require a cofactor. Reduction reactions catalyzed by the engineered ketoreductase enzymes described herein also typically require a cofactor, although many embodiments of the engineered ketoreductases require far less cofactor than reactions catalyzed with wild-type ketoreductase enzymes. As used herein, the term "cofactor" refers to a non-protein compound that operates in combination with a ketoreductase enzyme. Cofactors suitable for use with the engineered ketoreductase enzymes described herein include, but are not limited to, NADP$^+$ (nicotinamide adenine dinucleotide phosphate), NADPH (the reduced form of NADP$^+$) NAD$^+$ (nicotinamide adenine dinucleotide) and NADH (the reduced form of NAD$^+$) Generally, the reduced form of the cofactor is added to the reaction mixture. The reduced NAD(P)H form can be optionally regenerated from the oxidized NAD(P)$^+$ form using a cofactor regeneration system.

The term "cofactor regeneration system" refers to a set of reactants that participate in a reaction that reduces the oxidized form of the cofactor (e.g., NADP$^+$ to NADPH). Cofactors oxidized by the ketoreductase-catalyzed reduction of the keto substrate are regenerated in reduced form by the cofactor regeneration system. Cofactor regeneration systems comprise a stoichiometric reductant that is a source of reducing hydrogen equivalents and is capable of reducing the oxidized form of the cofactor. The cofactor regeneration system may further comprise a catalyst, for example an enzyme catalyst that catalyzes the reduction of the oxidized form of the cofactor by the reductant. Cofactor regeneration systems to regenerate NADH or NADPH from NAD$^+$ or NADP$^+$, respectively, are known in the art and may be used in the methods described herein.

Suitable exemplary cofactor regeneration systems that may be employed include, but are not limited to, glucose and glucose dehydrogenase, formate and formate dehydrogenase, glucose-6-phosphate and glucose-6-phosphate dehydrogenase, a secondary (e.g., isopropanol) alcohol and secondary alcohol dehydrogenase, phosphite and phosphite dehydrogenase, molecular hydrogen and hydrogenase, and the like. These systems may be used in combination with either NADP$^+$/NADPH or NAD$^+$/NADH as the cofactor. Electrochemical regeneration using hydrogenase may also be used as a cofactor regeneration system. See, e.g., U.S. Pat. Nos. 5,538,867 and 6,495,023, both of which are incorporated herein by reference. Chemical cofactor regeneration systems comprising a metal catalyst and a reducing agent (for example, molecular hydrogen or formate) are also suitable. See, e.g., PCT publication WO 2000/053731, which is incorporated herein by reference.

The terms "glucose dehydrogenase" and "GDH" are used interchangeably herein to refer to an NAD$^+$ or NADP$^+$-dependent enzyme that catalyzes the conversion of D-glucose and NAD$^+$ or NADP$^+$ to gluconic acid and NADH or NADPH, respectively. Equation (1), below, describes the glucose dehydrogenase-catalyzed reduction of NAD$^+$ or NADP$^+$ by glucose:

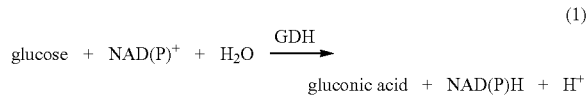

(1)

Glucose dehydrogenases that are suitable for use in the practice of the methods described herein include both naturally occurring glucose dehydrogenases, as well as non-naturally occurring glucose dehydrogenases. Naturally occurring glucose dehydrogenase encoding genes have been reported in the literature. For example, the *Bacillus subtilis* 61297 GDH gene was expressed in *E. coli* and was reported to exhibit the same physicochemical properties as the enzyme produced in its native host (Vasantha et al., 1983, Proc. Natl. Acad. Sci. USA 80:785). The gene sequence of the *B. subtilis* GDH gene, which corresponds to Genbank Acc. No. M12276, was reported by Lampel et al., 1986, J. Bacteriol. 166:238-243, and in corrected form by Yamane et al., 1996, Microbiology 142:3047-3056 as Genbank Acc. No. D50453. Naturally occurring GDH genes also include those that encode the GDH from *B. cereus* ATCC 14579 (Nature, 2003, 423:87-91; Genbank Acc. No. AE017013) and *B. megaterium* (Eur. J. Biochem., 1988, 174:485-490, Genbank Acc. No. X12370; J. Ferment. Bioeng., 1990, 70:363-369, Genbank Acc. No. GI216270). Glucose dehydrogenases from *Bacillus* sp. are provided in PCT publication WO 2005/018579 as SEQ ID NOS: 10 and 12 (encoded by polynucleotide sequences corresponding to SEQ ID NOS: 9 and 11, respectively, of the PCT publication), the disclosure of which is incorporated herein by reference.

Non-naturally occurring glucose dehydrogenases may be generated using known methods, such as, for example, mutagenesis, directed evolution, and the like. GDH enzymes having suitable activity, whether naturally occurring or non-naturally occurring, may be readily identified using the assay described in Example 4 of PCT publication WO 2005/018579, the disclosure of which is incorporated herein by reference. Exemplary non-naturally occurring glucose dehydrogenases are provided in PCT publication WO 2005/018579 as SEQ ID NOS: 62, 64, 66, 68, 122, 124, and 126. The polynucleotide sequences that encode them are provided in PCT publication WO 2005/018579 as SEQ ID NOS: 61, 63, 65, 67, 121, 123, and 125, respectively. All of these sequences are incorporated herein by reference. Additional non-naturally occurring glucose dehydrogenases that are suitable for use in the ketoreductase-catalyzed reduction reactions disclosed herein are provided in U.S. application publication Nos. 2005/0095619 and 2005/0153417, the disclosures of which are incorporated herein by reference.

Glucose dehydrogenases employed in the ketoreductase-catalyzed reduction reactions described herein may exhibit an activity of at least about 10 µmol/min/mg and sometimes at least about 10$^2$ µmol/min/mg or about 10$^3$ µmol/min/mg, up to about 10$^4$ µmol/min/mg or higher in the assay described in Example 4 of PCT publication WO 2005/018579.

The ketoreductase-catalyzed reduction reactions described herein are generally carried out in a solvent. Suitable solvents include water, organic solvents (e.g., ethyl acetate, butyl acetate, 2-propanol (isopropanol or IPA), 1-octanol, heptane, octane, methyl t-butyl ether (MTBE), toluene, and the like), and ionic liquids (e.g., 1-ethyl 4-methylimidazolium tetrafluoroborate, 1-butyl-3-methylimidazolium tetrafluoroborate, 1-butyl-3-methylimidazolium hexafluorophosphate, and the like). In some embodiments, aqueous solvents, including water and aqueous co-solvent systems, are used.

Exemplary aqueous co-solvent systems have water and one or more organic solvent. In general, an organic solvent component of an aqueous co-solvent system is selected such that it does not completely inactivate the ketoreductase enzyme. Appropriate co-solvent systems can be readily identified by measuring the enzymatic activity of the specified engineered ketoreductase enzyme with a defined substrate of interest in the candidate solvent system, utilizing an enzyme activity assay, such as those described herein.

The organic solvent component of an aqueous co-solvent system may be miscible with the aqueous component, providing a single liquid phase, or may be partly miscible or immiscible with the aqueous component, providing two liquid phases. Generally, when an aqueous co-solvent system is employed, it is selected to be biphasic, with water dispersed in an organic solvent, or vice-versa. Generally, when an aqueous co-solvent system is utilized, it is desirable to select an organic solvent that can be readily separated from the aqueous phase. In general, the ratio of water to organic solvent in the co-solvent system is typically in the range of from about 90:10 to about 10:90 (v/v) organic solvent to water, and between 80:20 and 20:80 (v/v) organic solvent to water. The co-solvent system may be pre-formed prior to addition to the reaction mixture, or it may be formed in situ in the reaction vessel.

The aqueous solvent (water or aqueous co-solvent system) may be pH-buffered or unbuffered. Generally, the reduction can be carried out at a pH of about 10 or below, usually in the range of from about 5 to about 10. In some embodiments, the reduction is carried out at a pH of about 9 or below, usually in the range of from about 5 to about 9. In some embodiments, the reduction is carried out at a pH of about 8 or below, often in the range of from about 5 to about 8, and usually in the range of from about 6 to about 8. The reduction may also be carried out at a pH of about 7.8 or below, or 7.5 or below. Alternatively, the reduction may be carried out a neutral pH, i.e., about 7.

During the course of the reduction reactions, the pH of the reaction mixture may change. The pH of the reaction mixture may be maintained at a desired pH or within a desired pH range by the addition of an acid or a base during the course of the reaction. Alternatively, the pH may be controlled by using an aqueous solvent that comprises a buffer. Suitable buffers to maintain desired pH ranges are known in the art and include, for example, phosphate buffer, triethanolamine buffer, and the like. Combinations of buffering and acid or base addition may also be used.

When the glucose/glucose dehydrogenase cofactor regeneration system is employed, the co-production of gluconic acid (pKa=3.6), as represented in equation (1) causes the pH of the reaction mixture to drop if the resulting aqueous gluconic acid is not otherwise neutralized. The pH of the reaction mixture may be maintained at the desired level by standard buffering techniques, wherein the buffer neutralizes the gluconic acid up to the buffering capacity provided, or by the addition of a base concurrent with the course of the conversion. Combinations of buffering and base addition may also be used. Suitable buffers to maintain desired pH ranges are described above. Suitable bases for neutralization of gluconic acid are organic bases, for example amines, alkoxides and the like, and inorganic bases, for example, hydroxide salts (e.g., NaOH), carbonate salts (e.g., NaHCO$_3$), bicarbonate salts (e.g., K$_2$CO$_3$), basic phosphate salts (e.g., K$_2$HPO$_4$, Na$_3$PO$_4$), and the like. The addition of a base concurrent with the course of the conversion may be done manually while monitoring the reaction mixture pH or, more conveniently, by using an automatic titrator as a pH stat. A combination of partial buffering capacity and base addition can also be used for process control.

When base addition is employed to neutralize gluconic acid released during a ketoreductase-catalyzed reduction reaction, the progress of the conversion may be monitored by the amount of base added to maintain the pH. Typically, bases added to unbuffered or partially buffered reaction mixtures over the course of the reduction are added in aqueous solutions.

In some embodiments, the co-factor regenerating system can comprises a formate dehydrogenase. The terms "formate dehydrogenase" and "FDH" are used interchangeably herein to refer to an NAD$^+$ or NADP$^+$-dependent enzyme that catalyzes the conversion of formate and NAD$^+$ or NADP$^+$ to carbon dioxide and NADH or NADPH, respectively. Formate dehydrogenases that are suitable for use as cofactor regenerating systems in the ketoreductase-catalyzed reduction reactions described herein include both naturally occurring formate dehydrogenases, as well as non-naturally occurring formate dehydrogenases. Formate dehydrogenases include those corresponding to SEQ ID NOS: 70 (*Pseudomonas* sp.) and 72 (*Candida boidinii*) of PCT publication WO 2005/018579, which are encoded by polynucleotide sequences corresponding to SEQ ID NOS: 69 and 71, respectively, of PCT publication 2005/018579, the disclosures of which are incorporated herein by reference. Formate dehydrogenases employed in the methods described herein, whether naturally occurring or non-naturally occurring, may exhibit an activity of at least about 1 μmol/min/mg, sometimes at least about 10 μmol/min/mg, or at least about 10$^2$ μmol/min/mg, up to about 10$^3$ μmol/min/mg or higher, and can be readily screened for activity in the assay described in Example 4 of PCT publication WO 2005/018579.

As used herein, the term "formate" refers to formate anion (HCO$_2^-$), formic acid (HCO$_2$H), and mixtures thereof. Formate may be provided in the form of a salt, typically an alkali or ammonium salt (for example, HCO$_2$Na, KHCO$_2$NH$_4$, and the like), in the form of formic acid, typically aqueous formic acid, or mixtures thereof. Formic acid is a moderate acid. In aqueous solutions within several pH units of its pKa (pKa=3.7 in water) formate is present as both HCO$_2^-$ and HCO$_2$H in equilibrium concentrations. At pH values above about pH 4, formate is predominantly present as HCO$_2^-$. When formate is provided as formic acid, the reaction mixture is typically buffered or made less acidic by adding a base to provide the desired pH, typically of about pH 5 or above. Suitable bases for neutralization of formic acid include, but are not limited to, organic bases, for example amines, alkoxides and the like, and inorganic bases, for example, hydroxide salts (e.g., NaOH), carbonate salts (e.g., NaHCO$_3$), bicarbonate salts (e.g., K$_2$CO$_3$), basic phosphate salts (e.g., K$_2$HPO$_4$, Na$_3$PO$_4$), and the like.

For pH values above about pH 5, at which formate is predominantly present as HCO$_2$, Equation (2) below, describes the formate dehydrogenase-catalyzed reduction of NAD$^+$ or NADP$^+$ by formate.

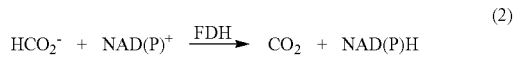

$$HCO_2^- + NAD(P)^+ \xrightarrow{FDH} CO_2 + NAD(P)H \qquad (2)$$

When formate and formate dehydrogenase are employed as the cofactor regeneration system, the pH of the reaction mixture may be maintained at the desired level by standard buffering techniques, wherein the buffer releases protons up to the buffering capacity provided, or by the addition of an acid concurrent with the course of the conversion. Suitable acids to add during the course of the reaction to maintain the pH include organic acids, for example carboxylic acids, sulfonic acids, phosphonic acids, and the like, mineral acids, for example hydrohalic acids (such as hydrochloric acid), sulfuric acid, phosphoric acid, and the like, acidic salts, for example dihydrogenphosphate salts (e.g., KH$_2$PO$_4$), bisulfate salts (e.g., NaHSO$_4$) and the like. Some embodiments utilize formic acid, whereby both the formate concentration and the pH of the solution are maintained.

When acid addition is employed to maintain the pH during a reduction reaction using the formate/formate dehydrogenase cofactor regeneration system, the progress of the conversion may be monitored by the amount of acid added to maintain the pH. Typically, acids added to unbuffered or partially buffered reaction mixtures over the course of conversion are added in aqueous solutions.

The terms "secondary alcohol dehydrogenase" and "sADH" are used interchangeably herein to refer to an $NAD^+$ or $NADP^+$-dependent enzyme that catalyzes the conversion of a secondary alcohol and $NAD^+$ or $NADP^+$ to a ketone and NADH or NADPH, respectively. Equation (3), below, describes the reduction of $NAD^+$ or $NADP^+$ by a secondary alcohol, illustrated by isopropanol.

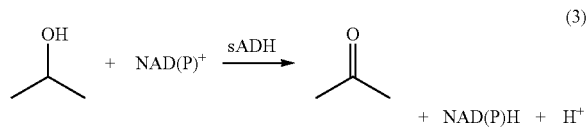

(3)

Secondary alcohol dehydrogenases that are suitable for use as cofactor regenerating systems in the ketoreductase-catalyzed reduction reactions described herein include both naturally occurring secondary alcohol dehydrogenases, as well as non-naturally occurring secondary alcohol dehydrogenases. Naturally occurring secondary alcohol dehydrogenases include known alcohol dehydrogenases from, *Thermoanaerobium brockii, Rhodococcus etythropolis, Lactobacillus kefiri, Lactobacillus brevis, Lactobacillus minor*, and non-naturally occurring secondary alcohol dehydrogenases include engineered alcohol dehdyrogenases derived therefrom. Secondary alcohol dehydrogenases employed in the methods described herein, whether naturally occurring or non-naturally occurring, may exhibit an activity of at least about 1 µmol/min/mg, sometimes at least about 10 µmol/min/mg, or at least about $10^2$ µmol/min/mg, up to about $10^3$ µmol/min/mg or higher.

Suitable secondary alcohols include lower secondary alkanols and aryl-alkyl carbinols. Examples of lower secondary alcohols include isopropanol, 2-butanol, 3-methyl-2-butanol, 2-pentanol, 3-pentanol, 3,3-dimethyl-2-butanol, and the like. In one embodiment the secondary alcohol is isopropanol. Suitable aryl-alkyl carbinols include unsubstituted and substituted 1-arylethanols.

When a secondary alcohol and secondary alcohol dehydrogenase are employed as the cofactor regeneration system, the resulting $NAD^+$ or $NADP^+$ is reduced by the coupled oxidation of the secondary alcohol to the ketone by the secondary alcohol dehydrogenase. Some engineered ketoreductases also have activity to dehydrogenate a secondary alcohol reductant. In some embodiments using secondary alcohol as reductant, the engineered ketoreductase and the secondary alcohol dehydrogenase are the same enzyme.

In carrying out embodiments of the ketoreductase-catalyzed reduction reactions described herein employing a cofactor regeneration system, either the oxidized or reduced form of the cofactor may be provided initially. As described above, the cofactor regeneration system converts oxidized cofactor to its reduced form, which is then utilized in the reduction of the ketoreductase substrate.

In some embodiments, cofactor regeneration systems are not used. For reduction reactions carried out without the use of a cofactor regenerating systems, the cofactor is added to the reaction mixture in reduced form.

In some embodiments, when the process is carried out using whole cells of the host organism, the whole cell may natively provide the cofactor. Alternatively or in combination, the cell may natively or recombinantly provide the glucose dehydrogenase.

In carrying out the stereospecific reduction reactions described herein, the engineered ketoreductase enzyme, and any enzymes comprising the optional cofactor regeneration system, may be added to the reaction mixture in the form of the purified enzymes, whole cells transformed with gene(s) encoding the enzymes, and/or cell extracts and/or lysates of such cells. The gene(s) encoding the engineered ketoreductase enzyme and the optional cofactor regeneration enzymes can be transformed into host cells separately or together into the same host cell. For example, in some embodiments one set of host cells can be transformed with gene(s) encoding the engineered ketoreductase enzyme and another set can be transformed with gene(s) encoding the cofactor regeneration enzymes. Both sets of transformed cells can be utilized together in the reaction mixture in the form of whole cells, or in the form of lysates or extracts derived therefrom. In other embodiments, a host cell can be transformed with gene(s) encoding both the engineered ketoreductase enzyme and the cofactor regeneration enzymes.

Whole cells transformed with gene(s) encoding the engineered ketoreductase enzyme and/or the optional cofactor regeneration enzymes, or cell extracts and/or lysates thereof, may be employed in a variety of different forms, including solid (e.g., lyophilized, spray-dried, and the like) or semisolid (e.g., a crude paste).

The cell extracts or cell lysates may be partially purified by precipitation (ammonium sulfate, polyethyleneimine, heat treatment or the like, followed by a desalting procedure prior to lyophilization (e.g., ultrafiltration, dialysis, and the like). Any of the cell preparations may be stabilized by crosslinking using known crosslinking agents, such as, for example, glutaraldehyde or immobilization to a solid phase (e.g., Eupergit C, and the like).

The solid reactants (e.g., enzyme, salts, etc.) may be provided to the reaction in a variety of different forms, including powder (e.g., lyophilized, spray dried, and the like), solution, emulsion, suspension, and the like. The reactants can be readily lyophilized or spray dried using methods and equipment that are known to those having ordinary skill in the art. For example, the protein solution can be frozen at −80° C. in small aliquots, then added to a prechilled lyophilization chamber, followed by the application of a vacuum. After the removal of water from the samples, the temperature is typically raised to 4° C. for two hours before release of the vacuum and retrieval of the lyophilized samples.

The quantities of reactants used in the reduction reaction will generally vary depending on the quantities of product desired, and concomitantly the amount of ketoreductase substrate employed. The following guidelines can be used to determine the amounts of ketoreductase, cofactor, and optional cofactor regeneration system to use. Generally, keto substrates can be employed at a concentration of about 20 to 300 grams/liter using from about 50 mg to about 5 g of ketoreductase and about 10 mg to about 150 mg of cofactor. Those having ordinary skill in the art will readily understand how to vary these quantities to tailor them to the desired level of productivity and scale of production. Appropriate quantities of optional cofactor regeneration system may be readily determined by routine experimentation based on the amount of cofactor and/or ketoreductase utilized. In general, the reductant (e.g., glucose, formate, and isopropanol) is utilized at levels above the equimolar level of ketoreductase substrate to achieve essentially complete or near complete conversion of the ketoreductase substrate.

The order of addition of reactants is not critical. The reactants may be added together at the same time to a solvent (e.g., monophasic solvent, biphasic aqueous co-solvent system, and the like), or alternatively, some of the reactants may be added separately, and some together at different time points. For example, the cofactor regeneration system, cofactor, ketoreductase, and ketoreductase substrate may be added first to the solvent.

For improved mixing efficiency when an aqueous co-solvent system is used, the cofactor regeneration system, ketoreductase, and cofactor may be added and mixed into the aqueous phase first. The organic phase may then be added and mixed in, followed by addition of the ketoreductase substrate. Alternatively, the ketoreductase substrate may be premixed in the organic phase, prior to addition to the aqueous phase.

Suitable conditions for carrying out the ketoreductase-catalyzed reduction reactions described herein include a wide variety of conditions which can be readily optimized by routine experimentation that includes, but is not limited to, contacting the engineered ketoreductase enzyme and substrate at an experimental pH and temperature and detecting product, for example, using the methods described in the Examples provided herein.

The ketoreductase catalyzed reduction is typically carried out at a temperature in the range of from about 15° C. to about 75° C. For some embodiments, the reaction is carried out at a temperature in the range of from about 20° C. to about 55° C. In still other embodiments, it is carried out at a temperature in the range of from about 20° C. to about 45° C. The reaction may also be carried out under ambient conditions.

The reduction reaction is generally allowed to proceed until essentially complete, or near complete, reduction of substrate is obtained. Reduction of substrate to product can be monitored using known methods by detecting substrate and/or product. Suitable methods include gas chromatography, HPLC, and the like. Conversion yields of the alcohol reduction product generated in the reaction mixture are generally greater than about 50%, may also be greater than about 60%, may also be greater than about 70%, may also be greater than about 80%, may also be greater than 90%, and are often greater than about 97%.

8. EXAMPLES

Various features and embodiments of the disclosure are illustrated in the following representative examples, which are intended to be illustrative, and not limiting.

In the following descriptions, wherever glucose dehydrogenase (GDH) is used, it is GDH CDX901, obtainable from Julich Chiral Solutions, Jülich, Germany.

8.1 Example 1

Wild-type Ketoreductase Gene Acquisition and Construction of Expression Vectors Ketoreductase (KRED) encoding genes were designed for expression in *E. coli* based on the reported amino acid sequence of the ketoreductase and a codon optimization algorithm as described in Example 1 of U.S. provisional application Ser. No. 60/848,950, incorporated herein by reference. (Standard codon-optimization software also is reviewed in e.g., "OPTIMIZER: a web server for optimizing the codon usage of DNA sequences," Puigbó et al., Nucleic Acids Res. 2007 July; 35 (Web Server issue): W126-31. Epub 2007 Apr. 16.) Genes were synthesized using oligonucleotides composed of 42 nucleotides and cloned into expression vector pCK110900 (depicted as FIG. 3 in United States Patent Application Publication 20060195947) under the control of a lac promoter. The expression vector also contained the P15a origin of replication and the chloramphenicol resistance gene. Resulting plasmids were transformed into *E. coli* W3110 using standard methods. Codon optimized genes and the encoding polypeptides as well are listed in Table 3. The activity of the wild-type ketoreductases was confirmed as described in U.S. provisional application Ser. No. 60/848,950.

TABLE 3

Abbreviations, source and references for Ketoreductases used

| KRED | Microorganism from which enzyme was originally identified | Genbank Acc. No. | GI number | Polynucleotide SEQ ID NO: | Polypeptide SEQ ID NO: or source |
|---|---|---|---|---|---|
| ADH-CM | *Candida magnoliae* | AB036927.1 | 12657576 | SEQ ID NO: 1 in US Patent Appln Publn 20060195947 | SEQ ID NO: 2 in US Patent Appln Publn 20060195947 |
| YDL | *Saccharomyces cerevisiae* | NP_010159.1 | 6320079 | SEQ ID NO: 1 in US Patent Appn. No. 60/848,950 | SEQ ID NO: 2 in US Patent Appn. No. 60/848,950 |
| ADH-LB | *Lactobacillus brevis* | 1NXQ_A | 30749782 | SEQ ID NO: 3 in US Patent Appn. No. 60/848,950 | SEQ ID NO: 4 in US Patent Appn. No. 60/848,950 |
| ADH-RE | *Rhodococcus erythropolis* | AAN73270.1 | 34776951 | SEQ ID NO: 5 in US Patent Appn. No. 60/848,950 | SEQ ID NO: 6 in US Patent Appn. No. 60/848,950 |
| YGL | *Saccharomyces cerevisiae* | NP_011476 | 6321399 | SEQ ID NO: 7 in US Patent Appn. No. 60/848,950 | SEQ ID NO: 8 in US Patent Appn. No. 60/848,950 |

TABLE 3-continued

Abbreviations, source and references for Ketoreductases used

| KRED | Microorganism from which enzyme was originally identified | Genbank Acc. No. | GI number | Polynucleotide SEQ ID NO: | Polypeptide SEQ ID NO: or source |
|---|---|---|---|---|---|
| YPR | Saccharomyces cerevisiae | NP_010656.1 | 6320576 | SEQ ID NO: 9 in US Patent Appn. No. 60/848,950 | SEQ ID NO: 10 in US Patent Appn. No. 60/848,950 |
| GRE | Saccharomyces cerevisiae | NP_014490.1 | 6324421 | SEQ ID NO: 11 in US Patent Appn. No. 60/848,950 | SEQ ID NO: 12 in US Patent Appn. No. 60/848,950 |
| ADH-LK | Lactobacillus kefir | AAP94029.1 | 33112056 | SEQ ID NO: 13 in US Patent Appn. No. 60/848,950 | SEQ ID NO: 14 in US Patent Appn. No. 60/848,950 |
| ADH-SB | Sporobolomyces salmonicolor | Q9UUN9 | 30315955 | SEQ ID NO: 103 in US Patent Appn. No. 60/972,058 | SEQ ID NO: 104 in US Patent Appn. No. 60/972,058 |
| ADH-SC | Streptomyces coelicolor | NP_631415.1 | 21225636 | SEQ ID NO: 101 in US Patent Appn. No. 60/972,058 | SEQ ID NO: 102 in US Patent Appn. No. 60/972,058 |
| ADH-TB | Thermoanaerobium brockii | X64841.1 | 1771790 | SEQ ID NO: 49 | SEQ ID NO: 50 |
| ADH-HE | Horse liver | DEHOAL | 625197 | SEQ ID NO: 51 | SEQ ID NO: 52 |
| ADH-AF | Aspergillus flavus | P41747 | 1168346 | SEQ ID NO: 111 in US Patent Appn. No. 60/976,345 | SEQ ID NO: 112 in US Patent Appn. No. 60/976,345 |
| ADH-OO1 | Oenococcus oeni | ZP_00318704.1 | 48864831 | SEQ ID NO: 113 in US Patent Appn. No. 60/976,345 | SEQ ID NO: 114 in US Patent Appn. No. 60/976,345 |
| ADH-RU | Ralstonia eutropha | ZP_00202558.1 | 46131317 | SEQ ID NO: 115 in US Patent Appn. No. 60/976,345 | SEQ ID NO: 116 in US Patent Appn. No. 60/976,345 |
| ADH-HS | Horse liver | DEHOAS | 625198 | SEQ ID NO: 53 | SEQ ID NO: 54 |
| ADH-OO2 | Oenococcus oeni | YP_8100051 | 116490461 | SEQ ID NO: 55 | SEQ ID NO: 56 |

Polynucleotides encoding engineered ketoreductases of the present invention were likewise cloned into vector pCK110900 for expression in *E. coli* W3110.

8.2 Example 2

Production of Ketoreductase Powders; Shake Flask Procedure

A single microbial colony of *E. coli* containing a plasmid with the ketoreductase gene of interest was inoculated into 50 ml Tryptic broth (12 g/L bacto-tryptone, 24 g/L yeast extract, 4 ml/L glycerol, 65 mM potassium phosphate, pH 7.0,) containing 30 µg/ml chloramphenicol and 1% glucose in a 250 ml Erlenmeyer flask. Cells were grown overnight (at least 16 hrs) in an incubator at 30° C. with shaking at 250 rpm. The culture was diluted into 250 ml Terrific Broth (1 mM MgSO$_4$, 30 µg/ml chloramphenicol) in 1 liter flask to an optical density at 600 nm (OD600) of 0.2 and allowed to grow at 30° C. Expression of the ketoreductase gene was induced with 1 mM IPTG when the OD600 of the culture is 0.6 to 0.8 and incubated overnight (at least 16 hrs). Cells were harvested by centrifugation (5000 rpm, 15 min, 4° C.) and the supernatant discarded. The cell pellet was resuspended with an equal volume of cold (4° C.) 100 mM triethanolamine (chloride) buffer, pH 7.0 (including 2 mM MgSO$_4$ in the case of ADH-LK and ADH-LB and engineered ketoreductases derived therefrom), and harvested by centrifugation as above. The washed cells were resuspended in 12 ml of the cold triethanolamine (chloride) buffer and passed through a French Press twice at 12000 psi while maintained at 4° C. Cell debris was removed by centrifugation (9000 rpm, 45 min., 4° C.). The clear lysate supernatant was collected and stored at −20° C. Lyophilization of frozen clear lysate provided a dry powder of crude ketoreductase enzyme.

8.3 Example 3

Production of Ketoreductases; Fermentation Procedure

In an aerated agitated 15 L fermenter, 6.0 L of growth medium containing 0.88 g/L ammonium sulfate, 0.98 g/L of sodium citrate; 12.5 g/L of dipotassium hydrogen phosphate trihydrate, 6.25 g/L of potassium dihydrogen phosphate, 6.2 g/L of Tastone-154 yeast extract, 0.083 g/L ferric ammonium citrate, and 8.3 ml/L of a trace element solution containing 2 g/L of calcium chloride dihydrate, 2.2 g/L of zinc sulfate septahydrate, 0.5 g/L manganese sulfate monohydrate, 1 g/L cuprous sulfate heptahydrate, 0.1 g/L ammonium molybdate tetrahydrate and 0.02 g/L sodium tetraborate decahydrate was brought to a temperature of 30° C. The fermenter was inoculated with a late exponential culture of *E. coli* W3110, containing a plasmid with the ketoreductase gene of interest, grown in a shake flask as described in Example 2 to a starting OD600 of 0.5 to 2.0. The fermenter was agitated at 500-1500 rpm and air was supplied to the fermentation vessel at 1.0-15.0 L/min to maintain dissolved oxygen level of 30% saturation or greater. The pH of the culture was controlled at 7.0 by addition of 20% v/v ammonium hydroxide. Growth of the culture was maintained by the addition of a feed solution containing 500 g/L cerelose, 12 g/L ammonium chloride and 10.4 g/L magnesium sulfate heptahydrate. After the culture reached an OD600 of 50, the expression of ketoreductase was induced by the addition of isopropyl-β-D-thiogalactoside (IPTG) to a final concentration of 1 mM. The culture was grown for another 14 hours. The culture was then chilled to 4° C. and maintained at 4° C. until harvested. Cells were harvested by centrifugation at 5000 G for 40 minutes in a Sorval RC12BP centrifuge at 4° C. Harvested cells were used directly in the following downstream recovery process or were stored at 4° C. until such use.

The cell pellet was resuspended in 2 volumes of 100 mM triethanolamine (chloride) buffer, pH 6.8, at 4° C. to each volume of wet cell paste. The intracellular ketoreductase was released from the cells by passing the suspension through a homogenizer fitted with a two-stage homogenizing valve assembly using a pressure of 12000 psi. The cell homogenate was cooled to 4° C. immediately after disruption. A solution of 10% w/v polyethyleneimine, pH 7.2, was added to the lysate to a final concentration of 0.5% w/v and stirred for 30 minutes. The resulting suspension was clarified by centrifugation at 5000 G in a standard laboratory centrifuge for 30 minutes. The clear supernatant was decanted and concentrated ten fold using a cellulose ultrafiltration membrane with a molecular weight cut off of 30 Kd. The final concentrate was dispensed into shallow containers, frozen at −20° C. and lyophilized to powder. The ketoreductase powder was stored at −80° C.

8.4 Example 4

Analytical Methods to Determine Conversion of 2-Methylpentanal and Stereomeric Excess of (R)-2-Methylpentanol Achiral GC to determine conversion. Reduction of 2-methylpentanal to 2-methylpentanol was determined using an Agilent 6850 Series II Gas chromatograph equipped with an Agilent 19091J-433E column (phenyl methyl siloxane, Capillary 30.0 m×250 μm×0.25 μm nominal) with an injection port temperature of 200° C. and a detector temperature of 300° C.; ramp profile: 60° C. for 3 min, ramp to 200° C. at 20° C. per minute, hold 1 min), split ratio 100:1, injection volume 1 μL, sample concentration ~15 mg/mL in IPA or MTBE, Helium Carrier Gas at 0.6 mL/min). Retention Times: 2-methylpentanal 1.84 min, 2-methylpentanol 2.53 min.

Chiral GC to determine stereopurity of 2-methylpentanol. The stereomeric purity of 2-methylpentanol was determined using an Agilent 6850 Series II Gas chromatograph equipped with an Chiraldex B-DP column (30 m×0.25 mM, cat no. 78023: Astec Inc., Whippany, N.J.), injection port temp 200° C., detector temp 300° C., oven temperature 65° C. (isothermal), split ratio 100:1, injection volume 3 μL, sample concentration ~15 mg/mL in IPA or MTBE, Helium Carrier Gas at 0.6 mL/min). Retention Times: (R)-2-methylpentanol 9.6 min, (S)-2-methylpentanol 10.9 min.

8.5 Example 5

Evaluation of Wild-Type and Previously Engineered Ketoreductases for Reduction of 2-methylvaleraldehyde to 2-methyl-pentanol KREDs described in Table 3 of Example 1 were evaluated for enantiospecific reduction of racemic 2-methylpentanal. To each well of a 96-well microtiter plate was added 5-10 mg of KRED, 20 mg of NAD(P)H in 500 μL of 100 mM triethanolamine(chloride) pH 7.0 and 15 μL 2-methylpentanal; (conversion limited to ~25% by the co-factor). The plate was sealed and shaken for 6 hours. The reactions were quenched by the addition of 1 mL of EtOAc. The conversion of the substrate using NADPH or NADH for supply of reducing equivalents were determined as described in Example 6 and results are listed in Table 4.

TABLE 4

| Activity of Wild-type KREDs | | |
|---|---|---|
| KRED | Conversion using NADPH[a] | Conversion using NADH[a] |
| CR2-5 | + | 0 |
| ADH-RE | + | + |
| ADH-LB | ++ | + |
| GRE | + | + |
| YDL | 0 | 0 |
| YGL | + | + |
| YPR | + | + |
| ADH-SC | 0 | 0 |
| ADH-SB | + | 0 |
| ADH-AF | 0 | 0 |
| ADH-LK | ++ | + |
| ADH-OO | 0 | 0 |
| ADH-RU | 0 | 0 |
| ADH-TB | + | 0 |
| ADH-HE | 0 | + |
| ADH-HS | 0 | + |
| ADH-OO2 | 0 | + |

[a]0: <1% conversion; +: 1-20% conversion; ++ >20% conversion

This example demonstrates that of all the enzymes tested, ADH-LB and ADH-LK gave the highest conversion. ADH-LK was taken as the starting enzyme for directed evolution.

8.6 Example 6

High Throughput NADPH Fluorescence Prescreen to Identify Improved Enzymes for the Reduction of 2-methylpentanol This first tier NADPH fluorescence-based prescreen was developed to measure initial conversion rate as well as assess the thermal stability of KRED variants. Plasmid libraries obtained by directed evolution and containing evolved ketoreductase genes were transformed into *E. coli* and plated on Luria-Bertani (LB) broth containing 1% glucose and 30 μg/mL chloramphenicol (CAM). After incubation for at least 16 hrs at 30° C., colonies were picked using a Q-bot® robotic colony picker (Genetix USA, Inc., Beaverton, Oreg.) into 96-well shallow well microtiter plates containing 180 μL Terrific broth (TB), 1% glucose and 30 μg/mL CAM. Cells were grown overnight at 30° C. with shaking at 200 rpm. 20 μL of this culture was then transferred into 96-deep well plates containing 350 μL Terrific broth (TB), 2 mM MgSO$_4$ and 30 μg/mL CAM. After incubation of deep-well plates at 30° C. with shaking at 250 rpm for 2 to 3 hours recombinant gene expression by the cell cultures was induced by addition of isopropyl thiogalactoside (IPTG) to a final concentration of 1 mM. The plates were then incubated at 30° C. with shaking at 250 rpm for 15-17 hrs.

Cells were pelleted via centrifugation, resuspended in 300 μL lysis buffer and lysed by shaking at room temperature for at least 1 hour. The lysis buffer contained 100 mM triethanolamine(chloride) buffer, pH 7.0-7.2, 1 mg/mL lysozyme, 200 μg/mL polymixin B sulfate and 2 mM $MgSO_4$. The plates were then spun at 4000 RPM for 10 minutes at 4° C. and the clear supernatant was used in the fluorescent assay.

In 96-well black microtiter plates 20 μl of sample was added to 180 μl of an assay mixture consisting of 90 mM triethanolamine(chloride) buffer pH 7.0, 1 mM $MgSO_4$, 1 g/L NADPH, 540 mM glucose, 540 mM sodium gluconate and 225 mM 2-methylpentanal and reaction progress measured by following the decrease in fluorescence of NADPH at 445 nm after excitation at 330 nm in a Flexstation (Molecular Devices, USA). If desired, KRED variants were pretreated for up 24 hrs at ambient temperature by diluting lysate samples 2-fold with a mixture containing 100 mM triethanolamine (chloride) buffer, pH 7.0, 2 mM $MgSO_4$, 450 mM glucose, 600 mM sodium gluconate and 1 M 2-methylpentanal.

This example describes the method that was used to identify KRED variants improved for the rate of 2-methylpentanal reduction.

8.7 Example 7

High Throughput Screening to Identify Improved Enzymes for the Stereospecific Reduction of 2-methylpentanal Using Glucose Dehydrogenase/Glucose for Co-Factor Regeneration Individual colonies of gene libraries were picked, grown and lysed as described in Example 6. To wells of a 96-well microtiter plate containing 10 mg calcium carbonate was added 50 μl 1 M triethanolamine(chloride) pH7.0, 200 μl 3 M glucose, 100 μl of a GDH/NADP stock containing 5 mg/ml glucose dehydrogenase (GDH) and 2 mg/ml Na-NADP (Oriental Yeast). Reactions were initiated by addition of 100 μl cell lysate and 50 μl 2-methylpentanal. After sealing the plates, reaction samples were shaken at ambient temperature for 1 hr. The plates were centrifuged (4000 rpm, 1 minute, ambient temperature) and 1 ml MTBE was added to each well. The plates were sealed with aluminum/polypropylene laminate heat seal tape (Velocity 11 (Menlo Park, Calif.), Cat #06643-001), and shaken for 3 minutes to extract product and remaining substrate, followed by centrifugation-aided phase separation (4000 rpm, 5 minutes, ambient temperature). 25 μl of the MTBE layer was diluted in duplicate into 175 μl ethylacetate for achiral GC analysis to determine stereopurity of 2-methylpentanol produced in the GDH recycling system. The stereomeric purity of 2-methylpentanol generated using the GDH recycling system was determined using an Agilent 6850 Series II Gas chromatograph equipped with an Chiraldex B-DM column (30 m×0.25 mM, cat no. 78023: Astec Inc., Whippany, N.J.), injection port temp 200° C., detector temp 300° C., oven temperature 50° C. (isothermal), split ratio 100:1, injection volume 3 sample concentration ~15 mg/mL in EtOAc, Helium Carrier Gas at 0.6 mL/min). Retention Times: Trifluoro acetic ester of (R)-2-methylpentanol 9.3 min, Trifluoro acetic ester (S)-2-methylpentanol 9.5 min.

For chiral GC screening, 650 μl of the MTBE layer was transferred to a deep-well plate (Costar #3960) containing 100 mg sodium sulfate. The plates were sealed as described above and shaken for 2 to 3 minutes. 400 μl of the dried MTBE layer was transferred to a new deep-well plate and 25 μl trifluoroacetic anhydride was added. The plate was sealed and shaken for at least 16 hrs at ambient temperature. Then 200 μl methanol was added to each well and after sealing, the plate was shaken for 2 hrs, followed by addition of 400 μl 1 M sodium bicarbonate and 400 μl ethylacetate. Plates were sealed and shaken for 2 to 3 minutes. After centrifugation (4000 rpm, 5 minutes, ambient temperature), 50 μl of the organic layer from each well was added to 150 μl ethylacetate in wells of a fresh microtiter plate. After sealing the plates, samples were subjected to chiral GC analysis (Example 4).

8.8 Example 8

High Throughput Screening to Identify Improved Enzymes for the Stereospecific Reduction of 2-methylpentanal Using Isopropylalcohol for Co-Factor Regeneration 50 μl of cell lysate obtained as described in Example 6 was transferred to a deep well plate (Costar #3960). 40 μl 1 M triethanolamine(chloride) buffer pH7.0, 50 μl 0.875 mg/ml Na-NADP (Oriental Yeast), 70 μl 2-methylpentanal, and 140 μl isopropyl alcohol was added to each well. After sealing the plates as described in Example 7, the reaction samples were shaken for at least 16 hrs at ambient temperature.

After centrifugation (4000 rpm, 1 min, ambient temperature) 1 ml of MTBE was added per well. Plates were resealed, shaken for 2 to 3 minutes, and the organic and aqueous layer separated by centrifugation (4000 rpm, 5 min, ambient temperature). 500 μl of the organic layer was transferred into a new deep well plate containing ~100 mg $Na_2SO_4$. The plates were sealed and shaken for 2 to 3 minutes. After centrifugation (4000 rpm, 5 minutes, ambient temperature), 100 μl of the organic layer from each well was added to 100 μl ethylacetate in wells of a fresh microtiter plate. After sealing the plates, samples were subjected to chiral GC analysis (Example 4).

8.9 Example 9

Resolution of 2-methylpentanal Via Stereospecific Reduction by Engineered Ketoreductases Derived from ADH-LK Using Glucose Dehydrogenase/Glucose for Co-Factor Regeneration Improved ADH-LK variants for the reduction of 2-methylpentanal to (R)-2-methyl-pentanol were evaluated at preparative scale as follows. To a 25 mL three-neck vessel equipped with a PTFE-coated magnetic stirring bar and a pH electrode connected to an automatic titrator for pH-controlled addition of base on-demand via a feeding tube into the vessel, was charged: 15 mL 100 mM triethanolamine(chloride) buffer pH7.0 5 g D-glucose, 31 mg lyophilized KRED variant sample as prepared in example 2 or 3, 32 μl of 1M $MgSO_4$, 25 mg GDH, 3 mg NADP-Na, 2.2 g 2-methylpentanal. Reactions were run at 25° C. and the automatic titrator maintained the pH at 7 by the addition of 4 N NaOH, which was continuously recorded. Reaction progress was monitored by the rate and cumulative addition of the base and periodic sampling of the reaction mixture for extraction with ethylacetate and analysis by the methods described in Example 4.

Table 5 gives the SEQ ID NO: corresponding to the ketoreductase, the number of amino acid mutations from the wild-type ADH-LK, the percent conversion and the enantiomeric excess of the product.

TABLE 5

Activity of ADH-LK Variants

| SEQ ID NO: | Number of mutations from ADH-LK | enantiospecificity[a] |
|---|---|---|
| 4 | 0 | + |
| 8 | 4 | ++ |
| 59 | 9 | + |

[a]+: >50% enantiomeric excess (e.e.) for the R-enantiomer at 40% conversion; ++: >80% stereomeric excess for the R-enantiomer at 40% conversion.

8.10 Example 10

Resolution of 2-methylpentanal Via Stereospecific Reduction by Engineered Ketoreductases Derived from ADH-LK Using Isopropylalcohol for Co-Factor Regeneration Improved ADH-LK variants for the reduction of 2-methylpentanal to (R)-2-methyl-pentanol were evaluated in small scale chemical reactions. KRED variants were evaluated as follows: to 20 ml reaction vials containing a magnetic stirrer bar was added 11 mL 100 mM triethanolamine(chloride) buffer (pH 7), 31 mg lyophilized KRED variant sample as prepared in example 2 or 3, 32 µl of 1M $MgSO_4$, 3 mg NADP-Na, 2.2 g 2-methylpentanal and 7 ml isopropylalcohol. Reactions were run at 25° C. for 18 to 24 hrs with continuous mixing. Reaction samples were analyzed by the methods of Example 4 and results are depicted in Table 6. In Table 6, the odd number refers to the SEQ ID NO. of the polynucleotide sequence while the even number refers to the SEQ ID NO. of the encoded polypeptide.

TABLE 6

Table 6: Activity and Stereoselectivity of ADH-LK Variants

| SEQ ID NO: * | E value | Number of amino acid mutations compared to ADH-LK |
|---|---|---|
| 3/4 | + | 0 |
| 7/8 | ++ | 4 |
| 29/30 | ++ | 3 |
| 21/22 | ++ | 2 |
| 41/42 | +++ | 4 |
| 15/16 | +++ | 3 |
| 19/20 | +++ | 3 |
| 17/18 | +++ | 3 |
| 11/12 | +++ | 3 |
| 25/26 | ++++ | 5 |
| 9/10 | +++ | 3 |
| 23/24 | +++++ | 4 |
| 13/14 | +++ | 6 |
| 5/6 | +++ | 5 |
| 35/36 | ++ | 5 |
| 37/38 | ++ | 6 |
| 33/34 | ++ | 5 |
| 31/32 | ++ | 5 |
| 39/40 | ++ | 5 |
| 27/28 | ++++ | 5 |
| 43/44 | ++++ | 5 |

+: E <50;
++: E 51-100;
+++: E 101-200;
++++: E 201-300;
+++++: E >301

8.11 Example 11

Evaluation of KRED Variants for Production of (R)-2-methylpentanol at Higher Substrate Concentrations Improved ADH-LK variants for the reduction of 2-methylpentanal to (R)-2-methyl-pentanol were evaluated in small scale chemical reactions using various substrate concentrations. KRED variants were evaluated in 5.4 ml reactions in 10 ml vials containing a magnetic stirrer bar. The reaction mixtures contained 1.4 ml 100 mM triethanolamine(chloride) buffer (pH7), 10 mg lyophilized KRED variant sample as prepared in example 2 or 3, 4 mM $MgSO_4$, 0.54 mg NADP-Na, and 2.90 ml of a mixture of 2-methylpentanal and isopropylalcohol as indicated in Table 7. Reactions were run at 25° C. for 24 hrs with continuous mixing. Reaction samples were analyzed by the methods of Example 4 and results are depicted in Table 7.

TABLE 7

Activity at higher substrate concentrations

| SEQ ID No | [rac. 2-methylpentanal] (g/L) | Conversion | Stereospecificity |
|---|---|---|---|
| 26 | 220 | ++ | * |
| 26 | 220 | ++ | * |
| 26 | 285 | ++ | ** |
| 26 | 285 | ++ | ** |
| 26 | 285 | + | ** |
| 26 | 285 | ++ | ** |
| 26 | 350 | + | ** |
| 26 | 350 | + | ** |
| 24 | 220 | ++ | * |
| 24 | 220 | ++ | * |
| 24 | 285 | ++ | *** |
| 24 | 285 | ++ | ** |
| 24 | 285 | ++ | ** |
| 24 | 285 | ++ | ** |
| 24 | 350 | ++ | *** |
| 24 | 350 | + | *** |

Conversion: +: 45-50%; ++: 50-55%
Enantiospecificity: * 96-98% e.e.; : 98-99% e.e.; * ≧99% e.e.

8.12 Example 12

Preparative Scale Production of (R)-2-methylpentanol

To a one-liter jacketed reaction vessel fitted with a mechanical stirring paddle, pH probe, nitrogen inlet, and thermocouple was added: 684 ml isopropyl alcohol, 285 ml 100 mM triethanolamine (pH9.5), 4 mM $MgSO_4$, 342 g 2-methylpentanal. Stirring was started at ~100 rpm and the temperature was set to 20.0° C. The pH was adjusted to pH=7.4±0.1 with 20% NaOH and after the desired temperature and pH were reached, the reaction was initiated by adding the following in order: 0.154 g NaNADP dissolved in 15 ml deionized water, 3.05 g KRED with SEQ ID NO:26 dissolved in 100 mL of deionized water. When the reaction reached 45% conversion as determined by GC analysis (Example 7) the enzyme was inactivated by charging 7.5 g EDTA and 15 g Celite 545. The mixture was stirred for at least 15 min prior to initiation of the work-up.

The reaction mixture was filtered through an "M" sintered glass funnel to remove insoluble materials and the filter cake washed with 75 ml isopropyl alcohol. The biphasic mixture was transferred to a two-liter distillation flask and the pH adjusted to 7±0.5 using 20% NaOH solution. The distillation flask was fitted with a thermocouple connected to a temperature controller, a heating mantle, and a jacketed distillation column. The distillation was allowed to proceed until a total of 810 mL of distillate was collected. The reaction was cooled to ~25° C. and 95 g sodium bisulfite dissolved in 200 mL deionized water was added over a 6 min period such that the temperature remained below 35° C. The reaction mixture was stirred for 2 hr at 35° C. during which time it became monophasic after which the pH was adjusted to 6.5 using 20% NaOH. The product to substrate ratio was 96:4.

(R)-2-methylpentanol was obtained by extraction 3× with 300 ml MTBE, followed by washing of the combined organic layer with 75 ml deionized water, 75 ml brine, 75 ml 0.5 N NaOH, 50 ml saturated NaHCO$_3$, and 25 mL brine. The organic solution was dried over ~30 g MgSO$_4$ for 3 hr and filtered into a two-Liter round bottom distillation flask fitted with a thermocouple connected to a temperature controller, heating mantle, and a jacketed distillation column. MTBE and residual IPA was removed by atmospheric distillation until the pot temperature reaches 130° C. followed by vacuum distillation at 275 mm Hg pressure. The fraction collected at a boiling point ranging from 109-110° C. afforded 101 g (R)-2-methylpentanol as a colorless liquid with a chemical purity of 97.7% and a stereomeric (R) purity of 98.5%.

All publications, patents, patent applications and other documents cited in this application are hereby incorporated by reference in their entireties for all purposes to the same extent as if each individual publication, patent, patent application or other document were individually indicated to be incorporated by reference for all purposes.

While various specific embodiments have been illustrated and described, it will be appreciated that various changes can be made without departing from the spirit and scope of the invention(s).

What is claimed is:

1. An isolated or recombinant polynucleotide encoding a ketoreductase polypeptide comprising an amino acid sequence having at least 90% identity to a reference sequence of SEQ ID NO: 4, wherein the residue corresponding to X153 is glutamine.

2. The polynucleotide of claim 1, wherein the encoded ketoreductase polypeptide comprises an amino acid sequence wherein the residue corresponding to X145 is serine.

3. The polynucleotide of claim 2, wherein the encoded ketoreductase polypeptide amino acid sequence further comprises one or more of the following features:
   residue corresponding to X72 is glutamic acid;
   residue corresponding to X82 is serine;
   residue corresponding to X96 is alanine, arginine, glutamine or lysine;
   residue corresponding to X104 is methionine;
   residue corresponding to X117 is serine;
   residue corresponding to X147 is cysteine, leucine, methionine or valine;
   residue corresponding to X157 is threonine;
   residue corresponding to X177 is glutamic acid;
   residue corresponding to X178 is glycine;
   residue corresponding to X202 is arginine, isoleucine or valine;
   residue corresponding to X223 is a glycine, methionine, alanine, valine, leucine or isoleucine; or
   residue corresponding to X236 is arginine; and
   wherein the amino acid sequence can optionally have one or more differences at other amino acid residues as compared to the reference sequence.

4. The polynucleotide of claim 1, wherein the encoded ketoreductase polypeptide comprises the amino acid sequence of SEQ ID NO: 14, 16, 18, 20, 22, 24, 26, 28, 30, 32, 34, 36, 38, 40, 42, or 44.

5. The polynucleotide of claim 1, wherein the polynucleotide comprises the nucleic acid sequence of SEQ ID NO: 13, 15, 17, 19, 21, 23, 25, 27, 29, 31, 33, 25, 27, 39, 41, or 43.

6. An expression vector comprising the polynucleotide of claim 1 operably linked to control sequences suitable for directing expression in a host cell.

7. A host cell comprising the expression vector of claim 6.

8. The host cell of claim 7, wherein the host cell is $E.\ coli$.

9. The host cell of claim 7, wherein the polynucleotide comprises codons that have been optimized for expression in the host cell.

10. A method for preparing a ketoreductase polypeptide comprising expressing a polynucleotide of claim 1 in a host cell and recovering the polypeptide from the host cell or culture medium.

11. The method of claim 10, wherein the host cell is $E.\ coli$.

* * * * *

SEQUENCE LISTING

```
<160> NUMBER OF SEQ ID NOS: 57

<210> SEQ ID NO 1
<211> LENGTH: 762
<212> TYPE: DNA
<213> ORGANISM: Artificial Sequence
<220> FEATURE:
<223> OTHER INFORMATION: Codon Optimized L. brevis Sequence

<400> SEQUENCE: 1
atgtctaacc gtctggatgg caaagtagcc atcattaccg gcgggactct gggtatcggt      60
ttggcaatcg ccacgaaatt tgtagaggag ggtgcgaaag taatgattac tggtcgtcac     120
tccgatgtag gtgaaaaggc cgccaaatca gtaggcactc cggatcagat tcagtttttt     180
cagcacgatt catccgatga agatggctgg acgaaactgt tcgacgccac cgagaaagca     240
ttcggcccgg ttagcacctt agtgaacaat gcagggattg cagttaacaa aagcgttgaa     300
gaaactacca cggccgaatg gcgtaaactg ctggccgtta atctggatgg tgttttttc      360 ggcacccgtc tgggcattca gcgcatgaaa aataaaggct gggcgctag catcatcaat      420 atgagcagta ttgaggggtt cgtaggcgat ccgagcctgg gggcatacaa cgcttccaag     480
ggggcggtac gtatcatgtc gaaaagcgca gcgctggatt gcgcactgaa ggactacgat     540
gtgcgtgtca acacagtaca tccgggctat atcaagaccc gctggtcga tgatctgccg      600 ggtgctgagg aagcgatgtc acagcgtacg aaaacccta tgggccacat tggcgaaccg      660
aatgacatcg catatatctg tgtgtacctg gcatctaatg aatcgaaatt tgcgacgggt     720
tccgaatttg tggtcgacgg cgggtatacc gcacagtaat ga                       762

<210> SEQ ID NO 2
<211> LENGTH: 252
<212> TYPE: PRT
<213> ORGANISM: Artificial Sequence
<220> FEATURE:
<223> OTHER INFORMATION: Translation of Codon Optimized L. brevis
      Sequence

<400> SEQUENCE: 2

Met Ser Asn Arg Leu Asp Gly Lys Val Ala Ile Ile Thr Gly Gly Thr
1               5                   10                  15

Leu Gly Ile Gly Leu Ala Ile Ala Thr Lys Phe Val Glu Glu Gly Ala
            20                  25                  30
```

Lys Val Met Ile Thr Gly Arg His Ser Asp Val Gly Glu Lys Ala Ala
            35                  40                  45
Lys Ser Val Gly Thr Pro Asp Gln Ile Gln Phe Phe Gln His Asp Ser
    50                  55                  60
Ser Asp Glu Asp Gly Trp Thr Lys Leu Phe Asp Ala Thr Glu Lys Ala
65                  70                  75                  80
Phe Gly Pro Val Ser Thr Leu Val Asn Asn Ala Gly Ile Ala Val Asn
                85                  90                  95
Lys Ser Val Glu Glu Thr Thr Thr Ala Glu Trp Arg Lys Leu Leu Ala
            100                 105                 110
Val Asn Leu Asp Gly Val Phe Phe Gly Thr Arg Leu Gly Ile Gln Arg
        115                 120                 125
Met Lys Asn Lys Gly Leu Gly Ala Ser Ile Ile Asn Met Ser Ser Ile
130                 135                 140
Glu Gly Phe Val Gly Asp Pro Ser Leu Gly Ala Tyr Asn Ala Ser Lys
145                 150                 155                 160
Gly Ala Val Arg Ile Met Ser Lys Ser Ala Ala Leu Asp Cys Ala Leu
                165                 170                 175
Lys Asp Tyr Asp Val Arg Val Asn Thr Val His Pro Gly Tyr Ile Lys
            180                 185                 190
Thr Pro Leu Val Asp Asp Leu Pro Gly Ala Glu Glu Ala Met Ser Gln
        195                 200                 205
Arg Thr Lys Thr Pro Met Gly His Ile Gly Glu Pro Asn Asp Ile Ala
210                 215                 220
Tyr Ile Cys Val Tyr Leu Ala Ser Asn Glu Ser Lys Phe Ala Thr Gly
225                 230                 235                 240
Ser Glu Phe Val Val Asp Gly Gly Tyr Thr Ala Gln
                245                 250

<210> SEQ ID NO 3
<211> LENGTH: 759
<212> TYPE: DNA
<213> ORGANISM: Artificial Sequence
<220> FEATURE:
<223> OTHER INFORMATION: Codon Optimized L. kefir Sequence

<400> SEQUENCE: 3

```
atgaccgatc gtctgaaggg caaagtagcc atcgtaaccg gcgggactct gggtatcggt      60
ttggcaatcg ccgataaatt tgtagaggag ggtgcgaaag tagttattac tggtcgtcac     120
gcggatgtag gtgaaaaggc cgccaaatca atcggcggca ctgatgttat cgctttgtc     180
cagcacgatg catccgatga agcaggctgg acgaaactgt tcgacaccac cgaggaggca     240
ttcggcccgg ttacgaccgt cgtgaacaat gcagggattg cagttccaa aagcgttgaa      300
gacactacca cggaggaatg gcgtaaactg ctgtccgtta atctggatgg tgttttttc      360
ggcacccgtc tgggcattca gcgcatgaaa aataaaggct gggcgctag catcatcaat      420
atgagcagta ttgaggggtt cgtaggcgat ccgacgctgg gggcatacaa cgcttccaag     480
ggggcggtac gtatcatgtc gaaaagcgca gcgctggatt gcgcactgaa ggactacgat     540
gtgcgtgtca acacagtaca tccgggctat atcaagaccc cgctggtcga tgatctggaa     600
ggtgctgagg aaatgatgtc acagcgtacg aaaaccccta tgggccacat tggcgaaccg     660
aatgacatcg catggatctg tgtgtacctg gcatctgacg aatcgaaatt tgcgacgggt     720
gcagaatttg tggtcgacgg cgggtatacc gcacagtga                            759
```

<210> SEQ ID NO 4

<211> LENGTH: 252
<212> TYPE: PRT
<213> ORGANISM: Artificial Sequence
<220> FEATURE:
<223> OTHER INFORMATION: Translation of Codon Optimized L. kefir Sequence

<400> SEQUENCE: 4

Met Thr Asp Arg Leu Lys Gly Lys Val Ala Ile Val Thr Gly Gly Thr
1               5                   10                  15

Leu Gly Ile Gly Leu Ala Ile Ala Asp Lys Phe Val Glu Glu Gly Ala
            20                  25                  30

Lys Val Val Ile Thr Gly Arg His Ala Asp Val Gly Glu Lys Ala Ala
        35                  40                  45

Lys Ser Ile Gly Gly Thr Asp Val Ile Arg Phe Val Gln His Asp Ala
    50                  55                  60

Ser Asp Glu Ala Gly Trp Thr Lys Leu Phe Asp Thr Thr Glu Glu Ala
65                  70                  75                  80

Phe Gly Pro Val Thr Thr Val Asn Asn Ala Gly Ile Ala Val Ser
                85                  90                  95

Lys Ser Val Glu Asp Thr Thr Glu Glu Trp Arg Lys Leu Leu Ser
            100                 105                 110

Val Asn Leu Asp Gly Val Phe Phe Gly Thr Arg Leu Gly Ile Gln Arg
        115                 120                 125

Met Lys Asn Lys Gly Leu Gly Ala Ser Ile Ile Asn Met Ser Ser Ile
130                 135                 140

Glu Gly Phe Val Gly Asp Pro Thr Leu Gly Ala Tyr Asn Ala Ser Lys
145                 150                 155                 160

Gly Ala Val Arg Ile Met Ser Lys Ser Ala Ala Leu Asp Cys Ala Leu
                165                 170                 175

Lys Asp Tyr Asp Val Arg Val Asn Thr Val His Pro Gly Tyr Ile Lys
            180                 185                 190

Thr Pro Leu Val Asp Asp Leu Glu Gly Ala Glu Glu Met Met Ser Gln
        195                 200                 205

Arg Thr Lys Thr Pro Met Gly His Ile Gly Glu Pro Asn Asp Ile Ala
    210                 215                 220

Trp Ile Cys Val Tyr Leu Ala Ser Asp Glu Ser Lys Phe Ala Thr Gly
225                 230                 235                 240

Ala Glu Phe Val Val Asp Gly Gly Tyr Thr Ala Gln
                245                 250

<210> SEQ ID NO 5
<211> LENGTH: 759
<212> TYPE: DNA
<213> ORGANISM: Artificial Sequence
<220> FEATURE:
<223> OTHER INFORMATION: variant of L. kefir

<400> SEQUENCE: 5
atgaccgatc gtctgaaggg caaagtagcc atcgtaaccg gcgggactct gggtatcggt        60
ttggcaatcg ccgataaatt tgtagaggag ggtgcgaaag tagttattac tggtcgccac       120
gcggatgtag gtgaaaaggc cgccaaatca atcggcggca ctgatgttat tcgctttgtc       180
cagcacgatg catccgatga agcaggctgg acgaaactgt tcgacaccac cgaggaggca       240
ttcggcccgg ttacgaccgt cgtgaacaat gcagggattg cagttgccaa agcgttgaa        300 gacactacca tggaggaatg gcgtaaactg ctgtccgtta atctggatag cgttttttc        360 ggcacccgtc tgggcattca gcgcatgaaa aataaaggct gggcgctag catcatcaat       420

```
atgagcagta tcagtgggtt cgtaggcgat ccgacgctgg gggcatacaa cgcttccaag    480
ggggcggtac gtatcatgtc gaaaagcgca gcgctggatt gcgcactgaa ggactacgat    540
gtgcgtgtca acacagtaca tccgggctat atcaagaccc cgctggtcga tgatctggaa    600
ggtgttgagg aaatgatgtc acagcgtacg aaaaccccta tgggccacat tggcgaaccg    660
aatgacatcg catggatctg tgtgtacctg gcatctgacg aatcgaaatt tgcgacgggt    720
gcagaatttg tggtcgacgg cgggtatacc gcacagtga                          759
```

<210> SEQ ID NO 6
<211> LENGTH: 252
<212> TYPE: PRT
<213> ORGANISM: Artificial Sequence
<220> FEATURE:
<223> OTHER INFORMATION: variant of L. kefir

<400> SEQUENCE: 6

```
Met Thr Asp Arg Leu Lys Gly Lys Val Ala Ile Val Thr Gly Gly Thr
1               5                   10                  15

Leu Gly Ile Gly Leu Ala Ile Ala Asp Lys Phe Val Glu Glu Gly Ala
            20                  25                  30

Lys Val Val Ile Thr Gly Arg His Ala Asp Val Gly Glu Lys Ala Ala
        35                  40                  45

Lys Ser Ile Gly Gly Thr Asp Val Ile Arg Phe Val Gln His Asp Ala
    50                  55                  60

Ser Asp Glu Ala Gly Trp Thr Lys Leu Phe Asp Thr Thr Glu Glu Ala
65                  70                  75                  80

Phe Gly Pro Val Thr Thr Val Val Asn Asn Ala Gly Ile Ala Val Ala
                85                  90                  95

Lys Ser Val Glu Asp Thr Thr Met Glu Glu Trp Arg Lys Leu Leu Ser
            100                 105                 110

Val Asn Leu Asp Ser Val Phe Phe Gly Thr Arg Leu Gly Ile Gln Arg
        115                 120                 125

Met Lys Asn Lys Gly Leu Gly Ala Ser Ile Ile Asn Met Ser Ser Ile
    130                 135                 140

Ser Gly Phe Val Gly Asp Pro Thr Leu Gly Ala Tyr Asn Ala Ser Lys
145                 150                 155                 160

Gly Ala Val Arg Ile Met Ser Lys Ser Ala Ala Leu Asp Cys Ala Leu
                165                 170                 175

Lys Asp Tyr Asp Val Arg Val Asn Thr Val His Pro Gly Tyr Ile Lys
            180                 185                 190

Thr Pro Leu Val Asp Asp Leu Glu Gly Val Glu Glu Met Met Ser Gln
        195                 200                 205

Arg Thr Lys Thr Pro Met Gly His Ile Gly Glu Pro Asn Asp Ile Ala
    210                 215                 220

Trp Ile Cys Val Tyr Leu Ala Ser Asp Glu Ser Lys Phe Ala Thr Gly
225                 230                 235                 240

Ala Glu Phe Val Val Asp Gly Gly Tyr Thr Ala Gln
                245                 250
```

<210> SEQ ID NO 7
<211> LENGTH: 759
<212> TYPE: DNA
<213> ORGANISM: Artificial Sequence
<220> FEATURE:
<223> OTHER INFORMATION: variant of L. kefir

<400> SEQUENCE: 7

```
atgaccgatc gtctgaaggg caaagtagcc atcgtaaccg gcgggactct gggtatcggt      60
ttggcaatcg ccgataaatt tgtagaggag ggtgcgaaag tagttattac tggtcgccac     120
gcggatgtag gtgaaaaggc cgccaaatca atcggcggca ctgatgttat tcgctttgtc     180
cagcacgatg catccgatga agcaggctgg acgaaactgt tcgacaccac cgaggaggca     240
ttcggcccgg ttacgaccgt cgtgaacaat gcagggattg cagtttccaa aagcgttgaa     300
gacactacca cggaggaatg gcgtaaactg ctgtccgtta atctggatag tgttttttc     360
ggcacccgtc tgggcattca gcgcatgaaa aataaaggct gggcgctag catcatcaat      420
atgagcagta tcagtgggtt cgtaggcgat ccgacactgg gggcatacac tgcttccaag     480
ggggcggtac gtatcatgtc gaaaagcgca gcgctggatt gcgcactgaa ggactacgat     540
gtgcgtgtca acacagtaca tccgggctat atcaagaccc cgctggtcga tgatctggaa     600
ggtgctgagg aaatgatgtc acagcgtacg aaaacccta tgggccacat tggcgaaccg      660
aatgacgtgg catggatctg tgtgtacctg gcatctgacg aatcgaaatt tgcgacgggt     720
gcagaatttg tggtcgacgg cgggtatacc gcacagtga                            759
```

<210> SEQ ID NO 8
<211> LENGTH: 252
<212> TYPE: PRT
<213> ORGANISM: Artificial Sequence
<220> FEATURE:
<223> OTHER INFORMATION: variant of L. kefir

<400> SEQUENCE: 8

```
Met Thr Asp Arg Leu Lys Gly Lys Val Ala Ile Val Thr Gly Gly Thr
1               5                   10                  15
Leu Gly Ile Gly Leu Ala Ile Ala Asp Lys Phe Val Glu Glu Gly Ala
            20                  25                  30
Lys Val Val Ile Thr Gly Arg His Ala Asp Val Gly Glu Lys Ala Ala
        35                  40                  45
Lys Ser Ile Gly Gly Thr Asp Val Ile Arg Phe Val Gln His Asp Ala
    50                  55                  60
Ser Asp Glu Ala Gly Trp Thr Lys Leu Phe Asp Thr Thr Glu Glu Ala
65                  70                  75                  80
Phe Gly Pro Val Thr Thr Val Val Asn Asn Ala Gly Ile Ala Val Ser
                85                  90                  95
Lys Ser Val Glu Asp Thr Thr Thr Glu Glu Trp Arg Lys Leu Leu Ser
            100                 105                 110
Val Asn Leu Asp Ser Val Phe Phe Gly Thr Arg Leu Gly Ile Gln Arg
        115                 120                 125
Met Lys Asn Lys Gly Leu Gly Ala Ser Ile Ile Asn Met Ser Ser Ile
    130                 135                 140
Ser Gly Phe Val Gly Asp Pro Thr Leu Gly Ala Tyr Thr Ala Ser Lys
145                 150                 155                 160
Gly Ala Val Arg Ile Met Ser Lys Ser Ala Ala Leu Asp Cys Ala Leu
                165                 170                 175
Lys Asp Tyr Asp Val Arg Val Asn Thr Val His Pro Gly Tyr Ile Lys
            180                 185                 190
Thr Pro Leu Val Asp Asp Leu Glu Gly Ala Glu Met Met Ser Gln
            195                 200                 205
Arg Thr Lys Thr Pro Met Gly His Ile Gly Glu Pro Asn Asp Val Ala
    210                 215                 220
Trp Ile Cys Val Tyr Leu Ala Ser Asp Glu Ser Lys Phe Ala Thr Gly
```

Ala Glu Phe Val Val Asp Gly Gly Tyr Thr Ala Gln
              245                 250

<210> SEQ ID NO 9
<211> LENGTH: 759
<212> TYPE: DNA
<213> ORGANISM: Artificial Sequence
<220> FEATURE:
<223> OTHER INFORMATION: variant of L. kefir

<400> SEQUENCE: 9

```
atgaccgatc gtctgaaggg caaagtagcc atcgtaaccg gcgggactct gggtatcggt      60
ttggcaatcg ccgataaatt tgtagaggag ggtgcgaaag tagttattac tggtcgccac     120
gcggatgtag gtgaaaaggc cgccaaatca atcggcggca ctgatgttat tcgctttgtc     180
cagcacgatg catccgatga agcaggctgg acgaaactgt tcgacaccac cgaggaggca     240
ttcggcccgg ttacgaccgt cgtgaacaat gcagggattg cagtttccaa agcgttgaa      300
gacactacca tggaggaatg gcgtaaactg ctgtccgtta atctggatgg tgttttttc      360
ggcacccgtc tgggcattca gcgcatgaaa aataaaggct gggcgctag catcatcaat      420
atgagcagta tcagtgggtt cgtaggcgat ccgacgctgg ggcatacaa cgcttccaag     480
ggggcggtac gtatcatgtc gaaaagcgca gcgctggatt gcgcactgaa ggactacgat     540
gtgcgtgtca acacagtaca tccgggctat atcaagaccc cgctggtcga tgatctggaa     600
ggtattgagg aaatgatgtc acagcgtacg aaaaccccta tgggccacat tggcgaaccg     660
aatgacatcg catggatctg tgtgtacctg gcatctgacg aatcgaaatt tgcgacgggt     720
gcagaatttg tggtcgacgg cgggtatacc gcacagtga                          759
```

<210> SEQ ID NO 10
<211> LENGTH: 252
<212> TYPE: PRT
<213> ORGANISM: Artificial Sequence
<220> FEATURE:
<223> OTHER INFORMATION: variant of L. kefir

<400> SEQUENCE: 10

Met Thr Asp Arg Leu Lys Gly Lys Val Ala Ile Val Thr Gly Gly Thr
1               5                   10                  15

Leu Gly Ile Gly Leu Ala Ile Ala Asp Lys Phe Val Glu Glu Gly Ala
            20                  25                  30

Lys Val Val Ile Thr Gly Arg His Ala Asp Val Gly Glu Lys Ala Ala
        35                  40                  45

Lys Ser Ile Gly Gly Thr Asp Val Ile Arg Phe Val Gln His Asp Ala
    50                  55                  60

Ser Asp Glu Ala Gly Trp Thr Lys Leu Phe Asp Thr Thr Glu Glu Ala
65                  70                  75                  80

Phe Gly Pro Val Thr Thr Val Val Asn Asn Ala Gly Ile Ala Val Ser
                85                  90                  95

Lys Ser Val Glu Asp Thr Thr Met Glu Glu Trp Arg Lys Leu Leu Ser
            100                 105                 110

Val Asn Leu Asp Gly Val Phe Phe Gly Thr Arg Leu Gly Ile Gln Arg
        115                 120                 125

Met Lys Asn Lys Gly Leu Gly Ala Ser Ile Ile Asn Met Ser Ser Ile
    130                 135                 140

Ser Gly Phe Val Gly Asp Pro Thr Leu Gly Ala Tyr Asn Ala Ser Lys
145                 150                 155                 160

```
Gly Ala Val Arg Ile Met Ser Lys Ser Ala Ala Leu Asp Cys Ala Leu
            165                 170                 175

Lys Asp Tyr Asp Val Arg Val Asn Thr Val His Pro Gly Tyr Ile Lys
        180                 185                 190

Thr Pro Leu Val Asp Asp Leu Glu Gly Ile Glu Glu Met Met Ser Gln
    195                 200                 205

Arg Thr Lys Thr Pro Met Gly His Ile Gly Pro Asn Asp Ile Ala
210                 215                 220

Trp Ile Cys Val Tyr Leu Ala Ser Asp Glu Ser Lys Phe Ala Thr Gly
225                 230                 235                 240

Ala Glu Phe Val Val Asp Gly Gly Tyr Thr Ala Gln
                245                 250
```

<210> SEQ ID NO 11
<211> LENGTH: 759
<212> TYPE: DNA
<213> ORGANISM: Artificial Sequence
<220> FEATURE:
<223> OTHER INFORMATION: variant of L. kefir

<400> SEQUENCE: 11

```
atgaccgatc gtctgaaggg caaagtagcc atcgtaaccg gcgggactct gggtatcggt    60
ttggcaatcg ccgataaatt tgtagaggag ggtgcgaaag tagttattac tggtcgccac   120
gcggatgtag gtgaaaaggc cgccaaatca atcggcggca ctgatgttat tcgctttgtc   180
cagcacgatg catccgatga agcaggctgg acgaaactgt tcgacaccac cgaggaggca   240
ttcggcccgg ttacgaccgt cgtgaacaat gcagggattg cagtttccaa aagcgttgaa   300
gacactacca tggaggaatg gcgtaaactg ctgtccgtta atctggatgg tgttttttc   360
ggcacccgtc tgggcattca gcgcatgaaa aataaaggct gggcgctag catcatcaat   420
atgagcagta tcagtgggtt cgtaggcgat ccgacgctgg ggcatacaa cgcttccaag   480
ggggcggtac gtatcatgtc gaaaagcgca gcgctggatt gcgcactgaa ggactacgat   540
gtgcgtgtca acacagtaca tccgggctat atcaagaccc cgctggtcga tgatctggaa   600
ggtgttgagg aaatgatgtc acagcgtacg aaaaccccta tgggccacat tggcgaaccg   660
aatgacatcg catggatctg tgtgtacctg gcatctgacg aatcgaaatt tgcgacgggt   720
gcagaatttg tggtcgacgg cgggtatacc gcacagtga                         759
```

<210> SEQ ID NO 12
<211> LENGTH: 252
<212> TYPE: PRT
<213> ORGANISM: Artificial Sequence
<220> FEATURE:
<223> OTHER INFORMATION: variant of L. kefir

<400> SEQUENCE: 12

```
Met Thr Asp Arg Leu Lys Gly Lys Val Ala Ile Val Thr Gly Gly Thr
1               5                   10                  15

Leu Gly Ile Gly Leu Ala Ile Ala Asp Lys Phe Val Glu Glu Gly Ala
            20                  25                  30

Lys Val Val Ile Thr Gly Arg His Ala Asp Val Gly Glu Lys Ala Ala
        35                  40                  45

Lys Ser Ile Gly Gly Thr Asp Val Ile Arg Phe Val Gln His Asp Ala
    50                  55                  60

Ser Asp Glu Ala Gly Trp Thr Lys Leu Phe Asp Thr Thr Glu Glu Ala
65                  70                  75                  80
```

```
Phe Gly Pro Val Thr Thr Val Asn Asn Ala Gly Ile Ala Val Ser
                85                  90                  95

Lys Ser Val Glu Asp Thr Thr Met Glu Glu Trp Arg Lys Leu Leu Ser
            100                 105                 110

Val Asn Leu Asp Gly Val Phe Phe Gly Thr Arg Leu Gly Ile Gln Arg
        115                 120                 125

Met Lys Asn Lys Gly Leu Gly Ala Ser Ile Ile Asn Met Ser Ser Ile
    130                 135                 140

Ser Gly Phe Val Gly Asp Pro Thr Leu Gly Ala Tyr Asn Ala Ser Lys
145                 150                 155                 160

Gly Ala Val Arg Ile Met Ser Lys Ser Ala Ala Leu Asp Cys Ala Leu
                165                 170                 175

Lys Asp Tyr Asp Val Arg Val Asn Thr Val His Pro Gly Tyr Ile Lys
            180                 185                 190

Thr Pro Leu Val Asp Asp Leu Glu Gly Val Glu Glu Met Met Ser Gln
        195                 200                 205

Arg Thr Lys Thr Pro Met Gly His Ile Gly Glu Pro Asn Asp Ile Ala
    210                 215                 220

Trp Ile Cys Val Tyr Leu Ala Ser Asp Glu Ser Lys Phe Ala Thr Gly
225                 230                 235                 240

Ala Glu Phe Val Val Asp Gly Gly Tyr Thr Ala Gln
                245                 250

<210> SEQ ID NO 13
<211> LENGTH: 759
<212> TYPE: DNA
<213> ORGANISM: Artificial Sequence
<220> FEATURE:
<223> OTHER INFORMATION: variant of L. kefir

<400> SEQUENCE: 13
atgaccgatc gtctgaaggg caaagtagcc atcgtaaccg gcgggactct gggtatcggt      60
ttggcaatcg ccgataaatt tgtagaggag ggtgcgaaag tagttattac tggtcgccac     120
gcggatgtag gtgaaaaggc cgccaaatca atcggcggca ctgatgttat tgctttgtc      180 cagcacgatg catccgatga agcaggctgg acggaactgt tcgacaccac cgaggaggca     240
ttcggcccgg ttacgaccgt cgtgaacaat gcagggattg cagttgccaa aagcgttgaa     300
gacactacca tggaggaatg gcgtaaactg ctgtccgtta atctggatag cgttttttc     360 ggcacccgtc tgggcattca gcgcatgaaa aataaaggct gggcgctag catcatcaat     420 atgagcagta tcagtgggtt cgtaggcgat ccgacgcagg gggcatacaa cgcttccaag     480
ggggcggtac gtatcatgtc gaaaagcgca gcgctggatt gcgcactgaa ggactacgat     540
gtgcgtgtca acacagtaca tccgggctat atcaagaccc cgctggtcga tgatctggaa     600
ggtgccgagg aaatgatgtc acagcgtacg aaaaccccta tgggccacat tggcgaaccg     660
aatgacatcg catggatctg tgtgtacctg gcatctgacg aatcgaaatt tgcgacgggt     720
gcagaatttg tggtcgacgg cgggtatacc gcacagtga                           759

<210> SEQ ID NO 14
<211> LENGTH: 252
<212> TYPE: PRT
<213> ORGANISM: Artificial Sequence
<220> FEATURE:
<223> OTHER INFORMATION: variant of L. kefir

<400> SEQUENCE: 14

Met Thr Asp Arg Leu Lys Gly Lys Val Ala Ile Val Thr Gly Gly Thr
```

```
                 1               5                  10                 15
Leu Gly Ile Gly Leu Ala Ile Ala Asp Lys Phe Val Glu Glu Gly Ala
                    20                 25                 30

Lys Val Val Ile Thr Gly Arg His Ala Asp Val Gly Glu Lys Ala Ala
            35                 40                 45

Lys Ser Ile Gly Gly Thr Asp Val Ile Arg Phe Val Gln His Asp Ala
    50                 55                 60

Ser Asp Glu Ala Gly Trp Thr Glu Leu Phe Asp Thr Thr Glu Glu Ala
65                 70                 75                 80

Phe Gly Pro Val Thr Thr Val Val Asn Asn Ala Gly Ile Ala Val Ala
                    85                 90                 95

Lys Ser Val Glu Asp Thr Thr Met Glu Glu Trp Arg Lys Leu Leu Ser
            100                105                110

Val Asn Leu Asp Ser Val Phe Phe Gly Thr Arg Leu Gly Ile Gln Arg
        115                120                125

Met Lys Asn Lys Gly Leu Gly Ala Ser Ile Ile Asn Met Ser Ser Ile
    130                135                140

Ser Gly Phe Val Gly Asp Pro Thr Gln Gly Ala Tyr Asn Ala Ser Lys
145                150                155                160

Gly Ala Val Arg Ile Met Ser Lys Ser Ala Ala Leu Asp Cys Ala Leu
                    165                170                175

Lys Asp Tyr Asp Val Arg Val Asn Thr Val His Pro Gly Tyr Ile Lys
            180                185                190

Thr Pro Leu Val Asp Asp Leu Glu Gly Ala Glu Glu Met Met Ser Gln
        195                200                205

Arg Thr Lys Thr Pro Met Gly His Ile Gly Glu Pro Asn Asp Ile Ala
    210                215                220

Trp Ile Cys Val Tyr Leu Ala Ser Asp Glu Ser Lys Phe Ala Thr Gly
225                230                235                240

Ala Glu Phe Val Val Asp Gly Gly Tyr Thr Ala Gln
                    245                250
```

<210> SEQ ID NO 15
<211> LENGTH: 759
<212> TYPE: DNA
<213> ORGANISM: Artificial Sequence
<220> FEATURE:
<223> OTHER INFORMATION: variant of L. kefir

<400> SEQUENCE: 15

```
atgaccgatc gtctgaaggg caaagtagcc atcgtaaccg gcgggactct gggtatcggt      60
ttggcaatcg ccgataaatt tgtagaggag ggtgcgaaag tagttattac tggtcgtcac     120
gcggatgtag gtgaaaaggc cgccaaatca atcggcggca ctgatgttat tcgcttcgtc     180
cagcacgatg catccgatga agcaggctgg acgaaactgt tcgacaccac cgaggaggca     240
ttcggcccgg ttacgaccgt cgtgaacaat gcagggattg cagttaagaa aagcgtcgaa     300
gacactacca cggaggaatg gcgtaaactg ctgtccgtta atctggatgg tgttttttc      360 ggcacccgtc tgggcattca gcgcatgaaa aataaaggct gggcgctag catcatcaat      420 atgagcagta ttgagggggtt cgtaggcgat ccgacgcagg gggcatacaa cgcttccaag     480
ggggcggtac gtatcatgtc gaaaagcgca gcgctggatt gcgcactgaa ggactacgat     540
gtgcgtgtca acacagtaca tccgggctat atcaagaccc cgctggtcga tgatctggaa     600
ggtgctgagg aaatgatgtc acagcgtacg aaaaccccta tgggccacat tggcgaaccg     660
aatgacatcg catggatctg tgtgtacctg gcatctgacg aatcgagatt tgcgacgggt     720
```
gcagaatttg tggtcgacgg cgggtatacc gcacagtga                759

<210> SEQ ID NO 16
<211> LENGTH: 252
<212> TYPE: PRT
<213> ORGANISM: Artificial Sequence
<220> FEATURE:
<223> OTHER INFORMATION: variant of L. kefir

<400> SEQUENCE: 16

Met Thr Asp Arg Leu Lys Gly Lys Val Ala Ile Val Thr Gly Gly Thr
1               5                   10                  15

Leu Gly Ile Gly Leu Ala Ile Ala Asp Lys Phe Val Glu Glu Gly Ala
            20                  25                  30

Lys Val Val Ile Thr Gly Arg His Ala Asp Val Gly Glu Lys Ala Ala
        35                  40                  45

Lys Ser Ile Gly Gly Thr Asp Val Ile Arg Phe Val Gln His Asp Ala
    50                  55                  60

Ser Asp Glu Ala Gly Trp Thr Lys Leu Phe Asp Thr Thr Glu Glu Ala
65                  70                  75                  80

Phe Gly Pro Val Thr Thr Val Val Asn Asn Ala Gly Ile Ala Val Lys
                85                  90                  95

Lys Ser Val Glu Asp Thr Thr Thr Glu Glu Trp Arg Lys Leu Leu Ser
            100                 105                 110

Val Asn Leu Asp Gly Val Phe Phe Gly Thr Arg Leu Gly Ile Gln Arg
        115                 120                 125

Met Lys Asn Lys Gly Leu Gly Ala Ser Ile Ile Asn Met Ser Ser Ile
    130                 135                 140

Glu Gly Phe Val Gly Asp Pro Thr Gln Gly Ala Tyr Asn Ala Ser Lys
145                 150                 155                 160

Gly Ala Val Arg Ile Met Ser Lys Ser Ala Ala Leu Asp Cys Ala Leu
                165                 170                 175

Lys Asp Tyr Asp Val Arg Val Asn Thr Val His Pro Gly Tyr Ile Lys
            180                 185                 190

Thr Pro Leu Val Asp Asp Leu Glu Gly Ala Glu Glu Met Met Ser Gln
        195                 200                 205

Arg Thr Lys Thr Pro Met Gly His Ile Gly Glu Pro Asn Asp Ile Ala
    210                 215                 220

Trp Ile Cys Val Tyr Leu Ala Ser Asp Glu Ser Arg Phe Ala Thr Gly
225                 230                 235                 240

Ala Glu Phe Val Val Asp Gly Gly Tyr Thr Ala Gln
                245                 250

<210> SEQ ID NO 17
<211> LENGTH: 759
<212> TYPE: DNA
<213> ORGANISM: Artificial Sequence
<220> FEATURE:
<223> OTHER INFORMATION: variant of L. kefir

<400> SEQUENCE: 17
atgaccgatc gtctgaaggg caaagtagcc atcgtaaccg gcgggactct gggtatcggt      60
ttggcaatcg ccgataaatt tgtagaggag ggtgcgaaag tagttattac tggtcgtcac     120
gcggatgtag gtgaaaaggc cgccaaatca atcggcggca ctgatgttat tcgcttcgtc     180
cagcacgatg catccgatga agcaggctgg acgaaactgt tcgacaccac cgaggaggca     240
ttcggcccgg ttacgaccgt cgtgaacaat gcagggattg cagttcagaa aagcgtcgaa     300

```
gacactacca cggaggaatg gcgtaaactg ctgtccgtta atctggatgg tgttttttc    360 ggcacccgtc tgggcattca gcgcatgaaa aataaaggct tgggcgctag catcatcaat    420
atgagcagta ttgagggtt cgtaggcgat ccgacgcagg gggcatacaa cgcttccaag    480
ggggcggtac gtatcatgtc gaaaagcgca gcgctggatt gcgcactgaa ggactacgat    540
gtgcgtgtca acacagtaca tccgggctat atcaagaccc cgctggtcga tgatctggaa    600
ggtgctgagg aaatgatgtc acagcgtacg aaaaccccta tgggccacat tggcgaaccg    660
aatgacatcg catggatctg tgtgtacctg gcatctgacg aatcgagatt tgcgacgggt    720
gcagaatttg tggtcgacgg cgggtatacc gcacagtga                          759
```

<210> SEQ ID NO 18
<211> LENGTH: 252
<212> TYPE: PRT
<213> ORGANISM: Artificial Sequence
<220> FEATURE:
<223> OTHER INFORMATION: variant of L. kefir

<400> SEQUENCE: 18

```
Met Thr Asp Arg Leu Lys Gly Lys Val Ala Ile Val Thr Gly Gly Thr
1               5                   10                  15

Leu Gly Ile Gly Leu Ala Ile Ala Asp Lys Phe Val Glu Glu Gly Ala
            20                  25                  30

Lys Val Val Ile Thr Gly Arg His Ala Asp Val Gly Glu Lys Ala Ala
        35                  40                  45

Lys Ser Ile Gly Gly Thr Asp Val Ile Arg Phe Val Gln His Asp Ala
    50                  55                  60

Ser Asp Glu Ala Gly Trp Thr Lys Leu Phe Asp Thr Thr Glu Glu Ala
65                  70                  75                  80

Phe Gly Pro Val Thr Thr Val Val Asn Asn Ala Gly Ile Ala Val Gln
                85                  90                  95

Lys Ser Val Glu Asp Thr Thr Thr Glu Glu Trp Arg Lys Leu Leu Ser
            100                 105                 110

Val Asn Leu Asp Gly Val Phe Phe Gly Thr Arg Leu Gly Ile Gln Arg
        115                 120                 125

Met Lys Asn Lys Gly Leu Gly Ala Ser Ile Ile Asn Met Ser Ser Ile
    130                 135                 140

Glu Gly Phe Val Gly Asp Pro Thr Gln Gly Ala Tyr Asn Ala Ser Lys
145                 150                 155                 160

Gly Ala Val Arg Ile Met Ser Lys Ser Ala Ala Leu Asp Cys Ala Leu
                165                 170                 175

Lys Asp Tyr Asp Val Arg Val Asn Thr Val His Pro Gly Tyr Ile Lys
            180                 185                 190

Thr Pro Leu Val Asp Asp Leu Glu Gly Ala Glu Glu Met Met Ser Gln
        195                 200                 205

Arg Thr Lys Thr Pro Met Gly His Ile Gly Glu Pro Asn Asp Ile Ala
    210                 215                 220

Trp Ile Cys Val Tyr Leu Ala Ser Asp Glu Ser Arg Phe Ala Thr Gly
225                 230                 235                 240

Ala Glu Phe Val Val Asp Gly Gly Tyr Thr Ala Gln
                245                 250
```

<210> SEQ ID NO 19
<211> LENGTH: 759
<212> TYPE: DNA
<213> ORGANISM: Artificial Sequence
<220> FEATURE:
<223> OTHER INFORMATION: variant of L. kefir

<400> SEQUENCE: 19

```
atgaccgatc gtctgaaggg caaagtagcc atcgtaaccg gcgggactct gggtatcggt     60
ttggcaatcg ccgataaatt tgtagaggag ggtgcgaaag tagttattac tggtcgtcac    120
gcggatgtag gtgaaaaggc cgccaaatca atcggcggca ctgatgttat tcgcttcgtc    180
cagcacgatg catccgatga agcaggctgg acgaaactgt tcgacaccac cgaggaggca    240
ttcggcccgg ttacgaccgt cgtgaacaat gcagggattg cagttcgtaa aagcgtcgaa    300
gacactacca cggaggaatg gcgtaaactg ctgtccgtta atctggatgg tgttttttc    360
ggcacccgtc tgggcattca gcgcatgaaa aataaaggct gggcgctag catcatcaat    420
atgagcagta ttgagggtt cgtaggcgat ccgacgcagg gggcatacaa cgcttccaag    480
ggggcggtac gtatcatgtc gaaaagcgca gcgctggatt gcgcactgaa ggactacgat    540
gtgcgtgtca acacagtaca tccgggctat atcaagaccc cgctggtcga tgatctggaa    600
ggtgctgagg aaatgatgtc acagcgtacg aaaaccccta tgggccacat tggcgaaccg    660
aatgacatcg catggatctg tgtgtacctg gcatctgacg aatcgagatt tgcgacgggt    720
gcagaatttg tggtcgacgg cgggtatacc gcacagtga                          759
```

<210> SEQ ID NO 20
<211> LENGTH: 252
<212> TYPE: PRT
<213> ORGANISM: Artificial Sequence
<220> FEATURE:
<223> OTHER INFORMATION: variant of L. kefir

<400> SEQUENCE: 20

```
Met Thr Asp Arg Leu Lys Gly Lys Val Ala Ile Val Thr Gly Gly Thr
1               5                   10                  15
Leu Gly Ile Gly Leu Ala Ile Ala Asp Lys Phe Val Glu Glu Gly Ala
            20                  25                  30
Lys Val Val Ile Thr Gly Arg His Ala Asp Val Gly Glu Lys Ala Ala
        35                  40                  45
Lys Ser Ile Gly Gly Thr Asp Val Ile Arg Phe Val Gln His Asp Ala
    50                  55                  60
Ser Asp Glu Ala Gly Trp Thr Lys Leu Phe Asp Thr Thr Glu Glu Ala
65                  70                  75                  80
Phe Gly Pro Val Thr Thr Val Val Asn Asn Ala Gly Ile Ala Val Arg
                85                  90                  95
Lys Ser Val Glu Asp Thr Thr Thr Glu Glu Trp Arg Lys Leu Leu Ser
            100                 105                 110
Val Asn Leu Asp Gly Val Phe Phe Gly Thr Arg Leu Gly Ile Gln Arg
        115                 120                 125
Met Lys Asn Lys Gly Leu Gly Ala Ser Ile Ile Asn Met Ser Ser Ile
    130                 135                 140
Glu Gly Phe Val Gly Asp Pro Thr Gln Gly Ala Tyr Asn Ala Ser Lys
145                 150                 155                 160
Gly Ala Val Arg Ile Met Ser Lys Ser Ala Ala Leu Asp Cys Ala Leu
                165                 170                 175
Lys Asp Tyr Asp Val Arg Val Asn Thr Val His Pro Gly Tyr Ile Lys
            180                 185                 190
Thr Pro Leu Val Asp Asp Leu Glu Gly Ala Glu Met Met Ser Gln
        195                 200                 205
```

```
Arg Thr Lys Thr Pro Met Gly His Ile Gly Glu Pro Asn Asp Ile Ala
        210                 215                 220
Trp Ile Cys Val Tyr Leu Ala Ser Asp Glu Ser Arg Phe Ala Thr Gly
225                 230                 235                 240
Ala Glu Phe Val Val Asp Gly Gly Tyr Thr Ala Gln
                245                 250
```

<210> SEQ ID NO 21
<211> LENGTH: 759
<212> TYPE: DNA
<213> ORGANISM: Artificial Sequence
<220> FEATURE:
<223> OTHER INFORMATION: variant of L. kefir

<400> SEQUENCE: 21

```
atgaccgatc gtctgaaggg caaagtagcc atcgtaaccg gcgggactct gggtatcggt      60
ttggcaatcg ccgataaatt tgtagaggag ggtgcgaaag tagttattac tggtcgtcac     120
gcggatgtag gtgaaaaggc cgccaaatca atcggcggca ctgatgttat tcgcttcgtc     180
cagcacgatg catccgatga agcaggctgg acgaaactgt tcgacaccac cgaggaggca     240
ttcggcccgg ttacgaccgt cgtgaacaat gcagggattg cagtttccaa agcgtcgaa     300
gacactacca cggaggaatg gcgtaaactg ctgtccgtta atctggatgg tgttttttc     360
ggcacccgtc tgggcattca gcgcatgaaa aataaaggct gggcgctag catcatcaat     420
atgagcagta ttgaggggtt cgtaggcgat ccgacgcagg gggcatacaa cgcttccaag     480
ggggcggtac gtatcatgtc gaaaagcgca gcgctggatt gcgcactgaa ggactacgat     540
gtgcgtgtca acacagtaca tccgggctat atcaagaccc cgctggtcga tgatctggaa     600
ggtgctgagg aaatgatgtc acagcgtacg aaaaccccta tggccacat ggcgaaccg     660
aatgacatcg catggatctg tgtgtacctg gcatctgacg aatcgagatt tgcgacgggt     720
gcagaatttg tggtcgacgg cgggtatacc gcacagtga                           759
```

<210> SEQ ID NO 22
<211> LENGTH: 252
<212> TYPE: PRT
<213> ORGANISM: Artificial Sequence
<220> FEATURE:
<223> OTHER INFORMATION: variant of L. kefir

<400> SEQUENCE: 22

```
Met Thr Asp Arg Leu Lys Gly Lys Val Ala Ile Val Thr Gly Gly Thr
1               5                   10                  15
Leu Gly Ile Gly Leu Ala Ile Ala Asp Lys Phe Val Glu Glu Gly Ala
            20                  25                  30
Lys Val Val Ile Thr Gly Arg His Ala Asp Val Gly Glu Lys Ala Ala
        35                  40                  45
Lys Ser Ile Gly Gly Thr Asp Val Ile Arg Phe Val Gln His Asp Ala
    50                  55                  60
Ser Asp Glu Ala Gly Trp Thr Lys Leu Phe Asp Thr Thr Glu Glu Ala
65                  70                  75                  80
Phe Gly Pro Val Thr Thr Val Val Asn Asn Ala Gly Ile Ala Val Ser
                85                  90                  95
Lys Ser Val Glu Asp Thr Thr Glu Glu Trp Arg Lys Leu Leu Ser
            100                 105                 110
Val Asn Leu Asp Gly Val Phe Phe Gly Thr Arg Leu Gly Ile Gln Arg
        115                 120                 125
Met Lys Asn Lys Gly Leu Gly Ala Ser Ile Ile Asn Met Ser Ser Ile
```

```
                   130                 135                 140
Glu Gly Phe Val Gly Asp Pro Thr Gln Gly Ala Tyr Asn Ala Ser Lys
145                 150                 155                 160

Gly Ala Val Arg Ile Met Ser Lys Ser Ala Ala Leu Asp Cys Ala Leu
                165                 170                 175

Lys Asp Tyr Asp Val Arg Val Asn Thr Val His Pro Gly Tyr Ile Lys
            180                 185                 190

Thr Pro Leu Val Asp Asp Leu Glu Gly Ala Glu Met Met Ser Gln
        195                 200                 205

Arg Thr Lys Thr Pro Met Gly His Ile Gly Glu Pro Asn Asp Ile Ala
    210                 215                 220

Trp Ile Cys Val Tyr Leu Ala Ser Asp Glu Ser Arg Phe Ala Thr Gly
225                 230                 235                 240

Ala Glu Phe Val Val Asp Gly Gly Tyr Thr Ala Gln
                245                 250

<210> SEQ ID NO 23
<211> LENGTH: 759
<212> TYPE: DNA
<213> ORGANISM: Artificial Sequence
<220> FEATURE:
<223> OTHER INFORMATION: variant of L. kefir

<400> SEQUENCE: 23
atgaccgatc gtctgaaggg caaagtagct atcgtaaccg gcgggactct gggtatcggt      60
ttggcaatcg ccgataaatt tgtagaggag ggtgcgaaag tagttattac gggtcgtcac     120
gcggatgtag gtgaaaaggc cgccaaatca atcggcggca ctgatgttat tcgctttgtc     180
cagcacgatg catccgatga agcaggctgg acgaaactgt tcgacaccac cgaggaggca     240
ttcagcccgg ttacgaccgt cgtgaacaat gcagggattg cagttgcgaa agcgttgaa      300 gacactacta cggaggaatg gcgtaagctg ctgtccgtta atctggatgg tgttttttc      360 ggcacccgtc tgggcattca gcgcatgaaa aataaaggct ggggcgctag catcatcaat     420
atgagcagta tttccgggtt cgtaggcgat ccgacgcagg gggcatacaa cgcttccaag     480
ggggcggttc gtatcatgtc gaaaagcgca gcgctggatt gcgcactgaa ggactacgat     540
gtgcgtgtca acacagtaca tccgggctat atcaagaccc cgctggtcga tgatctggaa     600
ggtgctgagg aaatgatgtc acagcgtacg aaaaccccta tgggccacat tggcgaaccg     660
aatgacatcg catggatctg tgtgtacctg gcatctgacg aatcgaaatt tgcgacgggt     720
gcagaatttg tggtcgacgg cgggtatacc gcacagtga                             759

<210> SEQ ID NO 24
<211> LENGTH: 252
<212> TYPE: PRT
<213> ORGANISM: Artificial Sequence
<220> FEATURE:
<223> OTHER INFORMATION: variant of L. kefir

<400> SEQUENCE: 24

Met Thr Asp Arg Leu Lys Gly Lys Val Ala Ile Val Thr Gly Gly Thr
1               5                   10                  15

Leu Gly Ile Gly Leu Ala Ile Ala Asp Lys Phe Val Glu Glu Gly Ala
                20                  25                  30

Lys Val Val Ile Thr Gly Arg His Ala Asp Val Gly Glu Lys Ala Ala
            35                  40                  45

Lys Ser Ile Gly Gly Thr Asp Val Ile Arg Phe Val Gln His Asp Ala
        50                  55                  60
```

Ser Asp Glu Ala Gly Trp Thr Lys Leu Phe Asp Thr Thr Glu Glu Ala
65                  70                  75                  80

Phe Ser Pro Val Thr Thr Val Val Asn Asn Ala Gly Ile Ala Val Ala
                85                  90                  95

Lys Ser Val Glu Asp Thr Thr Thr Glu Glu Trp Arg Lys Leu Leu Ser
            100                 105                 110

Val Asn Leu Asp Gly Val Phe Phe Gly Thr Arg Leu Gly Ile Gln Arg
        115                 120                 125

Met Lys Asn Lys Gly Leu Gly Ala Ser Ile Ile Asn Met Ser Ser Ile
    130                 135                 140

Ser Gly Phe Val Gly Asp Pro Thr Gln Gly Ala Tyr Asn Ala Ser Lys
145                 150                 155                 160

Gly Ala Val Arg Ile Met Ser Lys Ser Ala Ala Leu Asp Cys Ala Leu
                165                 170                 175

Lys Asp Tyr Asp Val Arg Val Asn Thr Val His Pro Gly Tyr Ile Lys
            180                 185                 190

Thr Pro Leu Val Asp Asp Leu Glu Gly Ala Glu Glu Met Met Ser Gln
        195                 200                 205

Arg Thr Lys Thr Pro Met Gly His Ile Gly Glu Pro Asn Asp Ile Ala
    210                 215                 220

Trp Ile Cys Val Tyr Leu Ala Ser Asp Glu Ser Lys Phe Ala Thr Gly
225                 230                 235                 240

Ala Glu Phe Val Val Asp Gly Gly Tyr Thr Ala Gln
                245                 250

<210> SEQ ID NO 25
<211> LENGTH: 759
<212> TYPE: DNA
<213> ORGANISM: Artificial Sequence
<220> FEATURE:
<223> OTHER INFORMATION: variant of L. kefir

<400> SEQUENCE: 25
atgaccgatc gtctgaaggg caaagtagct atcgtaaccg gcgggactct gggtatcggt      60
ttggcaatcg ccgataaatt tgtagaggag ggtgcgaaag tagttattac gggtcgtcac     120
gcggatgtag gtgaaaaggc cgccaaatca atcggcggca ctgatgttat tcgctttgtc     180
cagcacgatg catccgatga agcaggctgg acgaaactgt tcgacaccac cgaggaggca     240
ttcagcccgg ttacgaccgt cgtgaacaat gcagggattg cagttgcgaa agcgttgaa      300
gacactacta cggaggaatg gcgtaagctg ctgtccgtta atctggatgg tgttttttc     360
ggcacccgtc tgggcattca gcgcatgaaa aataaaggct gggcgctag catcatcaat     420
atgagcagta tttccggtt cgtaggcgat ccgacgcagg gggcatacaa cgcttccaag     480
ggggcggttc gtatcatgtc gaaaagcgca gcgctggatt gcgcactgaa ggactacgat     540
gtgcgtgtca acacagtaca tccgggctat atcaagaccc cgctggtcga tgatctggaa     600
ggtgctgagg aaatgatgtc acagcgtacg aaaaccccta tgggccacat tggcgaaccg     660
aatgacgtcg catggatctg tgtgtacctg gcatctgacg aatcgaaatt tgcgacgggt     720
gcagaatttg tggtcgacgg cgggtatacc gcacagtga                           759

<210> SEQ ID NO 26
<211> LENGTH: 252
<212> TYPE: PRT
<213> ORGANISM: Artificial Sequence
<220> FEATURE:
<223> OTHER INFORMATION: variant of L. kefir

<400> SEQUENCE: 26

Met Thr Asp Arg Leu Lys Gly Lys Val Ala Ile Val Thr Gly Gly Thr
1               5                   10                  15

Leu Gly Ile Gly Leu Ala Ile Ala Asp Lys Phe Val Glu Glu Gly Ala
            20                  25                  30

Lys Val Val Ile Thr Gly Arg His Ala Asp Val Gly Glu Lys Ala Ala
        35                  40                  45

Lys Ser Ile Gly Gly Thr Asp Val Ile Arg Phe Val Gln His Asp Ala
    50                  55                  60

Ser Asp Glu Ala Gly Trp Thr Lys Leu Phe Asp Thr Thr Glu Glu Ala
65                  70                  75                  80

Phe Ser Pro Val Thr Val Val Asn Asn Ala Gly Ile Ala Val Ala
                85                  90                  95

Lys Ser Val Glu Asp Thr Thr Glu Glu Trp Arg Lys Leu Leu Ser
                100                 105                 110

Val Asn Leu Asp Gly Val Phe Phe Gly Thr Arg Leu Gly Ile Gln Arg
            115                 120                 125

Met Lys Asn Lys Gly Leu Gly Ala Ser Ile Ile Asn Met Ser Ser Ile
130                 135                 140

Ser Gly Phe Val Gly Asp Pro Thr Gln Gly Ala Tyr Asn Ala Ser Lys
145                 150                 155                 160

Gly Ala Val Arg Ile Met Ser Lys Ser Ala Ala Leu Asp Cys Ala Leu
                165                 170                 175

Lys Asp Tyr Asp Val Arg Val Asn Thr Val His Pro Gly Tyr Ile Lys
            180                 185                 190

Thr Pro Leu Val Asp Asp Leu Glu Gly Ala Glu Glu Met Met Ser Gln
        195                 200                 205

Arg Thr Lys Thr Pro Met Gly His Ile Gly Glu Pro Asn Asp Val Ala
    210                 215                 220

Trp Ile Cys Val Tyr Leu Ala Ser Asp Glu Ser Lys Phe Ala Thr Gly
225                 230                 235                 240

Ala Glu Phe Val Val Asp Gly Gly Tyr Thr Ala Gln
                245                 250

<210> SEQ ID NO 27
<211> LENGTH: 759
<212> TYPE: DNA
<213> ORGANISM: Artificial Sequence
<220> FEATURE:
<223> OTHER INFORMATION: variant of L. kefir

<400> SEQUENCE: 27
atgaccgatc gtctgaaggg caaagtagct atcgtaaccg gcgggactct gggtatcggt    60
ttggcaatcg ccgataaatt tgtagaggag ggtgcgaaag tagttattac gggtcgtcac   120
gcggatgtag gtgaaaaggc cgccaaatca atcggcggca ctgatgttat tcgctttgtc   180
cagcacgatg catccgatga agcaggctgg acgaaactgt tcgacaccac cgaggaggca   240
ttcagcccgg ttacgaccgt cgtgaacaat gcagggattg cagttgcgaa agcgttgaa    300 gacactacta cggaggaatg cgtaagctg ctgtccgtta atctggatgg tgtttttttc    360
ggcacccgtc tgggcattca gcgcatgaaa aataaaggct gggcgctag catcatcaat    420 atgagcagta tttccgggtt cgtaggcgat ccgacgcagg gggcatacaa cgcttccaag    480
ggggcggttc gtatcatgtc gaaagcgca gcgctggatt gcgcactgaa ggactacgat    540
gtgcgtgtca acacagtaca tccgggctat atcaagaccc cgctggtcga tgatctggaa    600

-continued

```
ggtgctgagg aaatgatgtc acagcgtacg aaaacccta tgggccacat tggcgaaccg       660
aatgacgtcg catggatctg tgtgtacctg gcatctgacg aatcgaaatt tgcgacgggt       720
gcagaatttg tggtcgacgg cgggtatacc gcacagtga                              759
```

<210> SEQ ID NO 28
<211> LENGTH: 252
<212> TYPE: PRT
<213> ORGANISM: Artificial Sequence
<220> FEATURE:
<223> OTHER INFORMATION: variant of L. kefir

<400> SEQUENCE: 28

```
Met Thr Asp Arg Leu Lys Gly Lys Val Ala Ile Val Thr Gly Gly Thr
1               5                   10                  15

Leu Gly Ile Gly Leu Ala Ile Ala Asp Lys Phe Val Glu Glu Gly Ala
            20                  25                  30

Lys Val Val Ile Thr Gly Arg His Ala Asp Val Gly Glu Lys Ala Ala
        35                  40                  45

Lys Ser Ile Gly Gly Thr Asp Val Ile Arg Phe Val Gln His Asp Ala
    50                  55                  60

Ser Asp Glu Ala Gly Trp Thr Lys Leu Phe Asp Thr Thr Glu Glu Ala
65                  70                  75                  80

Phe Ser Pro Val Thr Thr Val Val Asn Asn Ala Gly Ile Ala Val Ala
                85                  90                  95

Lys Ser Val Glu Asp Thr Thr Thr Glu Glu Trp Arg Lys Leu Leu Ser
            100                 105                 110

Val Asn Leu Asp Gly Val Phe Phe Gly Thr Arg Leu Gly Ile Gln Arg
        115                 120                 125

Met Lys Asn Lys Gly Leu Gly Ala Ser Ile Ile Asn Met Ser Ser Ile
    130                 135                 140

Ser Gly Phe Val Gly Asp Pro Thr Gln Gly Ala Tyr Asn Ala Ser Lys
145                 150                 155                 160

Gly Ala Val Arg Ile Met Ser Lys Ser Ala Ala Leu Asp Cys Ala Leu
                165                 170                 175

Lys Asp Tyr Asp Val Arg Val Asn Thr Val His Pro Gly Tyr Ile Lys
            180                 185                 190

Thr Pro Leu Val Asp Asp Leu Glu Gly Ala Glu Met Met Ser Gln
        195                 200                 205

Arg Thr Lys Thr Pro Met Gly His Ile Gly Glu Pro Asn Asp Val Ala
    210                 215                 220

Trp Ile Cys Val Tyr Leu Ala Ser Asp Glu Ser Lys Phe Ala Thr Gly
225                 230                 235                 240

Ala Glu Phe Val Val Asp Gly Gly Tyr Thr Ala Gln
                245                 250
```

<210> SEQ ID NO 29
<211> LENGTH: 759
<212> TYPE: DNA
<213> ORGANISM: Artificial Sequence
<220> FEATURE:
<223> OTHER INFORMATION: variant of L. kefir

<400> SEQUENCE: 29

```
atgaccgatc gtctgaaggg caaagtagct atcgtaaccg gcgggactct gggtatcggt       60
ttggcaatcg ccgataaatt tgtagaggag ggtgcgaaag tagttattac gggtcgtcac      120
gcggatgtag gtgaaaaggc cgccaaatca atcggcggca ctgatgttat tcgctttgtc      180
```

```
cagcacgatg catccgatga agcaggctgg acgaaactgt tcgacaccac cgaggaggca      240
ttcagcccgg ttacgaccgt cgtgaacaat gcagggattg cagtttccaa aagcgttgaa      300
gacactacta cggaggaatg gcgtaaactg ctgtccgtta atctggatgg tgttttttc       360 ggcacccgtc tgggcattca gcgcatgaaa aataaaggct tgggcgctag catcatcaat      420
atgagcagta ttgagggggtt cgtaggcgat ccgacgcagg gggcatacaa cgcttccaag      480
ggggcggttc gtatcatgtc gaaaagcgca gcgctggatt gcgcactgaa ggactacgat      540
gtgcgtgtca acacagtaca tccgggctat atcaagaccc cgctggtcga tgatctggaa      600
ggtgctgagg aaatgatgtc acagcgtacg aaaaccccta tgggccacat tggcgaaccg      660
aatgacgtcg catggatctg tgtgtacctg gcatctgacg aatcgaaatt tgcgacgggt      720
gcagaatttg tggtcgacgg cgggtatacc gcacagtga                            759
```

<210> SEQ ID NO 30
<211> LENGTH: 252
<212> TYPE: PRT
<213> ORGANISM: Artificial Sequence
<220> FEATURE:
<223> OTHER INFORMATION: variant of L. kefir

<400> SEQUENCE: 30

```
Met Thr Asp Arg Leu Lys Gly Lys Val Ala Ile Val Thr Gly Gly Thr
1               5                   10                  15

Leu Gly Ile Gly Leu Ala Ile Ala Asp Lys Phe Val Glu Glu Gly Ala
            20                  25                  30

Lys Val Val Ile Thr Gly Arg His Ala Asp Val Gly Glu Lys Ala Ala
        35                  40                  45

Lys Ser Ile Gly Gly Thr Asp Val Ile Arg Phe Val Gln His Asp Ala
    50                  55                  60

Ser Asp Glu Ala Gly Trp Thr Lys Leu Phe Asp Thr Thr Glu Glu Ala
65                  70                  75                  80

Phe Ser Pro Val Thr Thr Val Asn Asn Ala Gly Ile Ala Val Ser
                85                  90                  95

Lys Ser Val Glu Asp Thr Thr Thr Glu Glu Trp Arg Lys Leu Leu Ser
            100                 105                 110

Val Asn Leu Asp Gly Val Phe Phe Gly Thr Arg Leu Gly Ile Gln Arg
        115                 120                 125

Met Lys Asn Lys Gly Leu Gly Ala Ser Ile Ile Asn Met Ser Ser Ile
    130                 135                 140

Glu Gly Phe Val Gly Asp Pro Thr Gln Gly Ala Tyr Asn Ala Ser Lys
145                 150                 155                 160

Gly Ala Val Arg Ile Met Ser Lys Ser Ala Ala Leu Asp Cys Ala Leu
                165                 170                 175

Lys Asp Tyr Asp Val Arg Val Asn Thr Val His Pro Gly Tyr Ile Lys
            180                 185                 190

Thr Pro Leu Val Asp Asp Leu Glu Gly Ala Glu Met Met Ser Gln
        195                 200                 205

Arg Thr Lys Thr Pro Met Gly His Ile Gly Glu Pro Asn Asp Val Ala
    210                 215                 220

Trp Ile Cys Val Tyr Leu Ala Ser Asp Glu Ser Lys Phe Ala Thr Gly
225                 230                 235                 240

Ala Glu Phe Val Val Asp Gly Gly Tyr Thr Ala Gln
                245                 250
```

<210> SEQ ID NO 31
<211> LENGTH: 759
<212> TYPE: DNA
<213> ORGANISM: Artificial Sequence
<220> FEATURE:
<223> OTHER INFORMATION: variant of L. kefir

<400> SEQUENCE: 31

```
atgaccgatc gtctgaaggg caaagtagct atcgtaaccg gcgggactct gggtatcggt      60
ttggcaatcg ccgataaatt tgtagaggag ggtgcgaaag tagttattac gggtcgtcac     120
gcggatgtag gtgaaaaggc cgccaaatca atcggcggca ctgatgttat tcgctttgtc     180
cagcacgatg catccgatga agcaggctgg acgaaactgt tcgacaccac cgaggaggca     240
ttcagcccgg ttacgaccgt cgtgaacaat gcagggattg cagtttccaa aagcgttgaa     300
gacactacta cggaggaatg gcgtaaactg ctgtccgtta atctggatgg tgttttttc     360
ggcacccgtc tgggcattca gcgcatgaaa ataaaggct tgggcgctag catcatcaat     420
atgagcagta tttccgggat ggtaggcgat ccgacgcagg gggcatacaa cgcttccaag     480
ggggcggttc gtatcatgtc gaaaagcgca gcgctggatt gcgcactgaa ggactacgat     540
gtgcgtgtca acacagtaca tccgggctat atcaagaccc cgctggtcga tgatctggaa     600
ggtgctgagg aaatgatgtc acagcgtacg aaaacccta tgggccacat tggcgaaccg     660
aatgacgtcg catggatctg tgtgtacctg gcatctgacg aatcgaaatt tgcgacgggt     720
gcagaatttg tggtcgacgg cgggtatacc gcacagtga                           759
```

<210> SEQ ID NO 32
<211> LENGTH: 252
<212> TYPE: PRT
<213> ORGANISM: Artificial Sequence
<220> FEATURE:
<223> OTHER INFORMATION: variant of L. kefir

<400> SEQUENCE: 32

```
Met Thr Asp Arg Leu Lys Gly Lys Val Ala Ile Val Thr Gly Gly Thr
  1               5                  10                  15
Leu Gly Ile Gly Leu Ala Ile Ala Asp Lys Phe Val Glu Glu Gly Ala
             20                  25                  30
Lys Val Val Ile Thr Gly Arg His Ala Asp Val Gly Glu Lys Ala Ala
         35                  40                  45
Lys Ser Ile Gly Gly Thr Asp Val Ile Arg Phe Val Gln His Asp Ala
     50                  55                  60
Ser Asp Glu Ala Gly Trp Thr Lys Leu Phe Asp Thr Thr Glu Glu Ala
 65                  70                  75                  80
Phe Ser Pro Val Thr Thr Val Val Asn Asn Ala Gly Ile Ala Val Ser
                 85                  90                  95
Lys Ser Val Glu Asp Thr Thr Thr Glu Glu Trp Arg Lys Leu Leu Ser
            100                 105                 110
Val Asn Leu Asp Gly Val Phe Phe Gly Thr Arg Leu Gly Ile Gln Arg
        115                 120                 125
Met Lys Asn Lys Gly Leu Gly Ala Ser Ile Ile Asn Met Ser Ser Ile
    130                 135                 140
Ser Gly Met Val Gly Asp Pro Thr Gln Gly Ala Tyr Asn Ala Ser Lys
145                 150                 155                 160
Gly Ala Val Arg Ile Met Ser Lys Ser Ala Ala Leu Asp Cys Ala Leu
                165                 170                 175
Lys Asp Tyr Asp Val Arg Val Asn Thr Val His Pro Gly Tyr Ile Lys
            180                 185                 190
```

Thr Pro Leu Val Asp Asp Leu Glu Gly Ala Glu Met Met Ser Gln
        195                 200                 205

Arg Thr Lys Thr Pro Met Gly His Ile Gly Glu Pro Asn Asp Val Ala
    210                 215                 220

Trp Ile Cys Val Tyr Leu Ala Ser Asp Glu Ser Lys Phe Ala Thr Gly
225                 230                 235                 240

Ala Glu Phe Val Val Asp Gly Gly Tyr Thr Ala Gln
                245                 250

<210> SEQ ID NO 33
<211> LENGTH: 759
<212> TYPE: DNA
<213> ORGANISM: Artificial Sequence
<220> FEATURE:
<223> OTHER INFORMATION: variant of L. kefir

<400> SEQUENCE: 33
atgaccgatc gtctgaaggg caaagtagct atcgtaaccg gcgggactct gggtatcggt      60
ttggcaatcg ccgataaatt tgtagaggag ggtgcgaaag tagttattac gggtcgtcac     120
gcggatgtag gtgaaaaggc cgccaaatca atcggcggca ctgatgttat tcgctttgtc     180
cagcacgatg catccgatga agcaggctgg acgaaactgt tcgacaccac cgaggaggca     240
ttcagcccgg ttacgaccgt cgtgaacaat gcagggattg cagtttccaa aagcgttgaa     300
gacactacta cggaggaatg gcgtaaactg ctgtccgtta atctggatgg tgtttttttc     360
ggcacccgtc tgggcattca gcgcatgaaa aataaaggct gggcgctag catcatcaat     420 atgagcagta tttccgggct ggtaggcgat ccgacgcagg gggcatacaa cgcttccaag     480
ggggcggttc gtatcatgtc gaaaagcgca gcgctggatt cgcactgaa ggactacgat     540 gtgcgtgtca acacagtaca tccgggctat atcaagaccc cgctggtcga tgatctggaa     600
ggtgctgagg aaatgatgtc acagcgtacg aaaaccccta tgggccacat tggcgaaccg     660
aatgacgtcg catggatctg tgtgtacctg gcatctgacg aatcgaaatt tgcgacgggt     720
gcagaatttg tggtcgacgg cgggtatacc gcacagtga                            759

<210> SEQ ID NO 34
<211> LENGTH: 252
<212> TYPE: PRT
<213> ORGANISM: Artificial Sequence
<220> FEATURE:
<223> OTHER INFORMATION: variant of L. kefir

<400> SEQUENCE: 34

Met Thr Asp Arg Leu Lys Gly Lys Val Ala Ile Val Thr Gly Gly Thr
1               5                   10                  15

Leu Gly Ile Gly Leu Ala Ile Ala Asp Lys Phe Val Glu Glu Gly Ala
                20                  25                  30

Lys Val Val Ile Thr Gly Arg His Ala Asp Val Gly Glu Lys Ala Ala
            35                  40                  45

Lys Ser Ile Gly Gly Thr Asp Val Ile Arg Phe Val Gln His Asp Ala
        50                  55                  60

Ser Asp Glu Ala Gly Trp Thr Lys Leu Phe Asp Thr Thr Glu Glu Ala
65                  70                  75                  80

Phe Ser Pro Val Thr Thr Val Val Asn Asn Ala Gly Ile Ala Val Ser
                85                  90                  95

Lys Ser Val Glu Asp Thr Thr Thr Glu Glu Trp Arg Lys Leu Leu Ser
            100                 105                 110

```
Val Asn Leu Asp Gly Val Phe Phe Gly Thr Arg Leu Gly Ile Gln Arg
        115                 120                 125

Met Lys Asn Lys Gly Leu Gly Ala Ser Ile Ile Asn Met Ser Ser Ile
    130                 135                 140

Ser Gly Leu Val Gly Asp Pro Thr Gln Gly Ala Tyr Asn Ala Ser Lys
145                 150                 155                 160

Gly Ala Val Arg Ile Met Ser Lys Ser Ala Ala Leu Asp Cys Ala Leu
                165                 170                 175

Lys Asp Tyr Asp Val Arg Val Asn Thr Val His Pro Gly Tyr Ile Lys
            180                 185                 190

Thr Pro Leu Val Asp Asp Leu Glu Gly Ala Glu Glu Met Met Ser Gln
        195                 200                 205

Arg Thr Lys Thr Pro Met Gly His Ile Gly Glu Pro Asn Asp Val Ala
    210                 215                 220

Trp Ile Cys Val Tyr Leu Ala Ser Asp Glu Ser Lys Phe Ala Thr Gly
225                 230                 235                 240

Ala Glu Phe Val Val Asp Gly Gly Tyr Thr Ala Gln
                245                 250
```

```
<210> SEQ ID NO 35
<211> LENGTH: 759
<212> TYPE: DNA
<213> ORGANISM: Artificial Sequence
<220> FEATURE:
<223> OTHER INFORMATION: variant of L. kefir

<400> SEQUENCE: 35
atgaccgatc gtctgaaggg caaagtagct atcgtaaccg gcgggactct gggtatcggt    60
ttggcaatcg ccgataaatt tgtagaggag ggtgcgaaag tagttattac gggtcgtcac   120
gcggatgtag gtgaaaaggc cgccaaatca atcggcggca ctgatgttat tcgctttgtc   180
cagcacgatg catccgatga agcaggctgg acgaaactgt tcgacaccac cgaggaggca   240
ttcagcccgg ttacgaccgt cgtgaacaat gcagggattg cagtttccaa aagcgttgaa   300
gacactacta cggaggaatg gcgtaaactg ctgtccgtta atctggatgg tgtttttttc   360
ggcacccgtc tgggcattca gcgcatgaaa aataaaggct gggcgctag catcatcaat   420 atgagcagta tttccggggt ggtaggcgat ccgacgcagg gggcatacaa cgcttccaag   480
ggggcggttc gtatcatgtc gaaaagcgca gcgctggatt gcgcactgaa ggactacgat   540
gtgcgtgtca acacagtaca tccgggctat atcaagaccc cgctggtcga tgatctggaa   600
ggtgctgagg aaatgatgtc acagcgtacg aaaaccccta tgggccacat tggcgaaccg   660
aatgacgtcg catggatctg tgtgtacctg gcatctgacg aatcgaaatt tgcgacgggt   720
gcagaatttg tggtcgacgg cgggtatacc gcacagtga                         759
```

```
<210> SEQ ID NO 36
<211> LENGTH: 252
<212> TYPE: PRT
<213> ORGANISM: Artificial Sequence
<220> FEATURE:
<223> OTHER INFORMATION: variant of L. kefir

<400> SEQUENCE: 36

Met Thr Asp Arg Leu Lys Gly Lys Val Ala Ile Val Thr Gly Gly Thr
1               5                   10                  15

Leu Gly Ile Gly Leu Ala Ile Ala Asp Lys Phe Val Glu Glu Gly Ala
            20                  25                  30

Lys Val Val Ile Thr Gly Arg His Ala Asp Val Gly Glu Lys Ala Ala
```

```
                     35                  40                  45
Lys Ser Ile Gly Gly Thr Asp Val Ile Arg Phe Val Gln His Asp Ala
 50                  55                  60

Ser Asp Glu Ala Gly Trp Thr Lys Leu Phe Asp Thr Thr Glu Glu Ala
 65                  70                  75                  80

Phe Ser Pro Val Thr Thr Val Asn Asn Ala Gly Ile Ala Val Ser
                     85                  90                  95

Lys Ser Val Glu Asp Thr Thr Thr Glu Glu Trp Arg Lys Leu Leu Ser
                100                 105                 110

Val Asn Leu Asp Gly Val Phe Phe Gly Thr Arg Leu Gly Ile Gln Arg
                115                 120                 125

Met Lys Asn Lys Gly Leu Gly Ala Ser Ile Ile Asn Met Ser Ser Ile
                130                 135                 140

Ser Gly Val Val Gly Asp Pro Thr Gln Gly Ala Tyr Asn Ala Ser Lys
145                 150                 155                 160

Gly Ala Val Arg Ile Met Ser Lys Ser Ala Ala Leu Asp Cys Ala Leu
                165                 170                 175

Lys Asp Tyr Asp Val Arg Val Asn Thr Val His Pro Gly Tyr Ile Lys
                180                 185                 190

Thr Pro Leu Val Asp Asp Leu Glu Gly Ala Glu Glu Met Met Ser Gln
                195                 200                 205

Arg Thr Lys Thr Pro Met Gly His Ile Gly Glu Pro Asn Asp Val Ala
                210                 215                 220

Trp Ile Cys Val Tyr Leu Ala Ser Asp Glu Ser Lys Phe Ala Thr Gly
225                 230                 235                 240

Ala Glu Phe Val Val Asp Gly Gly Tyr Thr Ala Gln
                245                 250

<210> SEQ ID NO 37
<211> LENGTH: 759
<212> TYPE: DNA
<213> ORGANISM: Artificial Sequence
<220> FEATURE:
<223> OTHER INFORMATION: variant of L. kefir

<400> SEQUENCE: 37
atgaccgatc gtctgaaggg caaagtagct atcgtaaccg gcgggactct gggtatcggt      60
ttggcaatcg ccgataaatt tgtagaggag ggtgcgaaag tagttattac gggtcgtcac     120
gcggatgtag gtgaaaaggc cgccaaatca atcggcggca ctgatgttat tcgctttgtc     180
cagcacgatg catccgatga agcaggctgg acgaaactgt tcgacaccac cgaggaggca     240
ttcagcccgg ttacgaccgt cgtgaacaat gcagggattg cagtttccaa aagcgttgaa     300
gacactacta cggaggaatg gcgtaaactg ctgtccgtta atctggatgg tgttttttc     360 ggcacccgtc tgggcattca gcgcatgaaa aataaaggct gggcgctag catcatcaat     420 atgagcagta tttccggggt tgtaggcgat ccgacgcagg gggcatacaa cgcttccaag     480
ggggcggttc gtatcatgtc gaaaagcgca gcgctggatt gcgcactgaa gggctacgat     540
gtgcgtgtca acacagtaca tccgggctat atcaagaccc cgctggtcga tgatctggaa     600
ggtgctgagg aaatgatgtc acagcgtacg aaaaccccta tgggccacat tggcgaaccg     660
aatgacgtcg catggatctg tgtgtacctg gcatctgacg aatcgaaatt tgcgacgggt     720
gcagaatttg tggtcgacgg cgggtatacc gcacagtga                           759

<210> SEQ ID NO 38
<211> LENGTH: 252
```

<212> TYPE: PRT
<213> ORGANISM: Artificial Sequence
<220> FEATURE:
<223> OTHER INFORMATION: variant of L. kefir

<400> SEQUENCE: 38

```
Met Thr Asp Arg Leu Lys Gly Lys Val Ala Ile Val Thr Gly Gly
1               5                   10                  15
Leu Gly Ile Gly Leu Ala Ile Ala Asp Lys Phe Val Glu Glu Gly Ala
            20                  25                  30
Lys Val Val Ile Thr Gly Arg His Ala Asp Val Gly Glu Lys Ala Ala
        35                  40                  45
Lys Ser Ile Gly Gly Thr Asp Val Ile Arg Phe Val Gln His Asp Ala
    50                  55                  60
Ser Asp Glu Ala Gly Trp Thr Lys Leu Phe Asp Thr Thr Glu Glu Ala
65                  70                  75                  80
Phe Ser Pro Val Thr Thr Val Asn Asn Ala Gly Ile Ala Val Ser
                85                  90                  95
Lys Ser Val Glu Asp Thr Thr Glu Glu Trp Arg Lys Leu Leu Ser
            100                 105                 110
Val Asn Leu Asp Gly Val Phe Phe Gly Thr Arg Leu Gly Ile Gln Arg
        115                 120                 125
Met Lys Asn Lys Gly Leu Gly Ala Ser Ile Ile Asn Met Ser Ser Ile
    130                 135                 140
Ser Gly Val Val Gly Asp Pro Thr Gln Gly Ala Tyr Asn Ala Ser Lys
145                 150                 155                 160
Gly Ala Val Arg Ile Met Ser Lys Ser Ala Ala Leu Asp Cys Ala Leu
                165                 170                 175
Lys Gly Tyr Asp Val Arg Val Asn Thr Val His Pro Gly Tyr Ile Lys
            180                 185                 190
Thr Pro Leu Val Asp Asp Leu Glu Gly Ala Glu Glu Met Met Ser Gln
        195                 200                 205
Arg Thr Lys Thr Pro Met Gly His Ile Gly Glu Pro Asn Asp Val Ala
    210                 215                 220
Trp Ile Cys Val Tyr Leu Ala Ser Asp Glu Ser Lys Phe Ala Thr Gly
225                 230                 235                 240
Ala Glu Phe Val Val Asp Gly Gly Tyr Thr Ala Gln
                245                 250
```

<210> SEQ ID NO 39
<211> LENGTH: 759
<212> TYPE: DNA
<213> ORGANISM: Artificial Sequence
<220> FEATURE:
<223> OTHER INFORMATION: variant of L. kefir

<400> SEQUENCE: 39

```
atgaccgatc gtctgaaggg caaagtagct atcgtaaccg gcgggactct gggtatcggt    60
ttggcaatcg ccgataaatt tgtagaggag ggtgcgaaag tagttattac gggtcgtcac   120
gcggatgtag gtgaaaaggc cgccaaatca atcggcggca ctgatgttat tcgctttgtc   180
cagcacgatg catccgatga agcaggctgg acgaaactgt tcgacaccac cgaggaggca   240
ttcagcccgg ttacgaccgt cgtgaacaat gcagggattg cagtttccaa agcgttgaa    300 gacactacta cggaggaatg gcgtaaactg ctgtccgtta atctggatgg tgttttttc    360 ggcacccgtc tgggcattca gcgcatgaaa aataaaggct gggcgctag catcatcaat   420 atgagcagta tttccggtgt gtaggcgat ccgacgcagg gggcatacaa cgcttccaag   480
```

```
ggggcggttc gtatcatgtc gaaaagcgca gcgctggatt gcgcactgaa ggactacgat     540
gtgcgtgtca acacagtaca tccgggctat atcaagaccc cgctggtcga tgatctggaa     600
ggtgctgagg aaatgatgtc acagcgtacg aaaacccta tgggccacat tggcgaaccg      660
aatgacgtcg catggatctg tgtgtacctg gcatctgacg aatcgaaatt tgcgacgggt     720
gcagaatttg tggtcgacgg cgggtatacc gcacagtga                            759
```

```
<210> SEQ ID NO 40
<211> LENGTH: 252
<212> TYPE: PRT
<213> ORGANISM: Artificial Sequence
<220> FEATURE:
<223> OTHER INFORMATION: variant of L. kefir

<400> SEQUENCE: 40
```

Met Thr Asp Arg Leu Lys Gly Lys Val Ala Ile Val Thr Gly Gly Thr
1               5                   10                  15

Leu Gly Ile Gly Leu Ala Ile Ala Asp Lys Phe Val Glu Glu Gly Ala
                20                  25                  30

Lys Val Val Ile Thr Gly Arg His Ala Asp Val Gly Glu Lys Ala Ala
            35                  40                  45

Lys Ser Ile Gly Gly Thr Asp Val Ile Arg Phe Val Gln His Asp Ala
        50                  55                  60

Ser Asp Glu Ala Gly Trp Thr Lys Leu Phe Asp Thr Thr Glu Glu Ala
65                  70                  75                  80

Phe Ser Pro Val Thr Thr Val Val Asn Asn Ala Gly Ile Ala Val Ser
                85                  90                  95

Lys Ser Val Glu Asp Thr Thr Thr Glu Glu Trp Arg Lys Leu Leu Ser
            100                 105                 110

Val Asn Leu Asp Gly Val Phe Phe Gly Thr Arg Leu Gly Ile Gln Arg
        115                 120                 125

Met Lys Asn Lys Gly Leu Gly Ala Ser Ile Ile Asn Met Ser Ser Ile
    130                 135                 140

Ser Gly Cys Val Gly Asp Pro Thr Gln Gly Ala Tyr Asn Ala Ser Lys
145                 150                 155                 160

Gly Ala Val Arg Ile Met Ser Lys Ser Ala Ala Leu Asp Cys Ala Leu
                165                 170                 175

Lys Asp Tyr Asp Val Arg Val Asn Thr Val His Pro Gly Tyr Ile Lys
            180                 185                 190

Thr Pro Leu Val Asp Asp Leu Glu Gly Ala Glu Glu Met Met Ser Gln
        195                 200                 205

Arg Thr Lys Thr Pro Met Gly His Ile Gly Glu Pro Asn Asp Val Ala
    210                 215                 220

Trp Ile Cys Val Tyr Leu Ala Ser Asp Glu Ser Lys Phe Ala Thr Gly
225                 230                 235                 240

Ala Glu Phe Val Val Asp Gly Gly Tyr Thr Ala Gln
                245                 250

```
<210> SEQ ID NO 41
<211> LENGTH: 759
<212> TYPE: DNA
<213> ORGANISM: Artificial Sequence
<220> FEATURE:
<223> OTHER INFORMATION: variant of L. kefir

<400> SEQUENCE: 41
atgaccgatc gtctgaaggg caaagtagct atcgtaaccg gcgggactct gggtatcggt     60
```

-continued

```
ttggcaatcg ccgataaatt tgtagaggag ggtgcgaaag tagttattac gggtcgtcac    120
gcggatgtag gtgaaaaggc cgccaaatca atcggcggca ctgatgttat tcgctttgtc    180
cagcacgatg catccgatga agcaggctgg acgaaactgt tcgacaccac cgaggaggca    240
ttcagcccgg ttacgaccgt cgtgaacaat gcagggattg cagtttccaa aagcgttgaa    300
gacactacta cggaggaatg gcgtaaactg ctgtccgtta atctggatgg tgttttttc     360 ggcacccgtc tgggcattca gcgcatgaaa aataaaggct gggcgctag catcatcaat     420 atgagcagta tttccgggtt cgtaggcgat ccgacgcagg gggcatacaa cgcttccaag    480
ggggcggttc gtatcatgtc gaaaagcgca gcgctggatt gcgcactgaa ggactacgat    540
gtgcgtgtca acacagtaca tccgggctat atcaagaccc cgctggtcga tgatctggaa    600
ggtgctgagg aaatgatgtc acagcgtacg aaaacccta tgggccacat tggcgaaccg     660
aatgacgtcg catggatctg tgtgtacctg gcatctgacg aatcgaaatt tgcgacgggt    720
gcagaatttg tggtcgacgg cgggtatacc gcacagtga                          759
```

<210> SEQ ID NO 42
<211> LENGTH: 252
<212> TYPE: PRT
<213> ORGANISM: Artificial Sequence
<220> FEATURE:
<223> OTHER INFORMATION: variant of L. kefir

<400> SEQUENCE: 42

```
Met Thr Asp Arg Leu Lys Gly Lys Val Ala Ile Val Thr Gly Gly Thr
  1               5                  10                  15

Leu Gly Ile Gly Leu Ala Ile Ala Asp Lys Phe Val Glu Glu Gly Ala
             20                  25                  30

Lys Val Val Ile Thr Gly Arg His Ala Asp Val Gly Glu Lys Ala Ala
         35                  40                  45

Lys Ser Ile Gly Gly Thr Asp Val Ile Arg Phe Val Gln His Asp Ala
     50                  55                  60

Ser Asp Glu Ala Gly Trp Thr Lys Leu Phe Asp Thr Thr Glu Glu Ala
 65                  70                  75                  80

Phe Ser Pro Val Thr Thr Val Asn Asn Ala Gly Ile Ala Val Ser
                 85                  90                  95

Lys Ser Val Glu Asp Thr Thr Thr Glu Glu Trp Arg Lys Leu Leu Ser
                100                 105                 110

Val Asn Leu Asp Gly Val Phe Phe Gly Thr Arg Leu Gly Ile Gln Arg
            115                 120                 125

Met Lys Asn Lys Gly Leu Gly Ala Ser Ile Ile Asn Met Ser Ser Ile
        130                 135                 140

Ser Gly Phe Val Gly Asp Pro Thr Gln Gly Ala Tyr Asn Ala Ser Lys
145                 150                 155                 160

Gly Ala Val Arg Ile Met Ser Lys Ser Ala Ala Leu Asp Cys Ala Leu
                165                 170                 175

Lys Asp Tyr Asp Val Arg Val Asn Thr Val His Pro Gly Tyr Ile Lys
            180                 185                 190

Thr Pro Leu Val Asp Asp Leu Glu Gly Ala Glu Glu Met Met Ser Gln
        195                 200                 205

Arg Thr Lys Thr Pro Met Gly His Ile Gly Glu Pro Asn Asp Val Ala
    210                 215                 220

Trp Ile Cys Val Tyr Leu Ala Ser Asp Glu Ser Lys Phe Ala Thr Gly
225                 230                 235                 240
```

```
Ala Glu Phe Val Val Asp Gly Gly Tyr Thr Ala Gln
            245                 250
```

```
<210> SEQ ID NO 43
<211> LENGTH: 759
<212> TYPE: DNA
<213> ORGANISM: Artificial Sequence
<220> FEATURE:
<223> OTHER INFORMATION: variant of L. kefir

<400> SEQUENCE: 43
atgaccgatc gtctgaaggg caaagtagct atcgtaaccg gcgggactct gggtatcggt      60
ttggcaatcg ccgataaatt tgtagaggag ggtgcgaaag tagttattac gggtcgtcac     120
gcggatgtag gtgaaagggc cgccaaatca atcggcggca ctgatgttat tcgctttgtc     180
cagcacgatg catccgatga agcaggctgg acgaaactgt tcgacaccac cgaggaggca     240
ttcagcccgg ttacgaccgt cgtgaacaat gcagggattg cagtttccaa aagcgttgaa     300
gacactacta cggaggaatg gcgtaaactg ctgtccgtta atctggatgg tgttttttc     360 ggcacccgtc tgggcattca gcgcatgaaa aataaaggct gggcgctag catcatcaat     420 atgagcagta tttccgggtt cgtaggcgat ccgacgcagg gggcatacaa cgcttccaag     480
ggggcggttc gtatcatgtc gaaaagcgca gcgctggatt gcgcactgaa ggactacgat     540
gtgcgtgtca acacagtaca tccgggctat atcaagaccc cgctggtcga tgatctggaa     600
ggtgctgagg aaatgatgtc acagcgtacg aaaaccccta tgggccacat tggcgaaccg     660
aatgacgtcg catggatctg tgtgtacctg gcatctgacg aatcgaaatt tgcgacgggt     720
gcagaatttg tggtcgacgg cgggtatacc gcacagtga                           759
```

```
<210> SEQ ID NO 44
<211> LENGTH: 252
<212> TYPE: PRT
<213> ORGANISM: Artificial Sequence
<220> FEATURE:
<223> OTHER INFORMATION: variant of L. kefir

<400> SEQUENCE: 44

Met Thr Asp Arg Leu Lys Gly Lys Val Ala Ile Val Thr Gly Gly Thr
1               5                   10                  15

Leu Gly Ile Gly Leu Ala Ile Ala Asp Lys Phe Val Glu Glu Gly Ala
            20                  25                  30

Lys Val Val Ile Thr Gly Arg His Ala Asp Val Gly Glu Arg Ala Ala
        35                  40                  45

Lys Ser Ile Gly Gly Thr Asp Val Ile Arg Phe Val Gln His Asp Ala
    50                  55                  60

Ser Asp Glu Ala Gly Trp Thr Lys Leu Phe Asp Thr Thr Glu Glu Ala
65                  70                  75                  80

Phe Ser Pro Val Thr Thr Val Val Asn Asn Ala Gly Ile Ala Val Ser
                85                  90                  95

Lys Ser Val Glu Asp Thr Thr Thr Glu Glu Trp Arg Lys Leu Leu Ser
            100                 105                 110

Val Asn Leu Asp Gly Val Phe Phe Gly Thr Arg Leu Gly Ile Gln Arg
        115                 120                 125

Met Lys Asn Lys Gly Leu Gly Ala Ser Ile Ile Asn Met Ser Ser Ile
    130                 135                 140

Ser Gly Phe Val Gly Asp Pro Thr Gln Gly Ala Tyr Asn Ala Ser Lys
145                 150                 155                 160

Gly Ala Val Arg Ile Met Ser Lys Ser Ala Ala Leu Asp Cys Ala Leu
```

|   |   |   |   |   | 165 |   |   |   | 170 |   |   |   | 175 |   |
|---|---|---|---|---|---|---|---|---|---|---|---|---|---|---|
| Lys | Asp | Tyr | Asp | Val | Arg | Val | Asn | Thr | Val | His | Pro | Gly | Tyr | Ile | Lys |

|   |   | 180 |   |   |   |   | 185 |   |   |   | 190 |   |   |
|---|---|---|---|---|---|---|---|---|---|---|---|---|---|
| Thr | Pro | Leu | Val | Asp | Asp | Leu | Glu | Gly | Ala | Glu | Glu | Met | Met | Ser | Gln |

|   |   |   |   | 195 |   |   |   | 200 |   |   |   | 205 |   |   |
|---|---|---|---|---|---|---|---|---|---|---|---|---|---|---|
| Arg | Thr | Lys | Thr | Pro | Met | Gly | His | Ile | Gly | Glu | Pro | Asn | Asp | Val | Ala |

|   |   | 210 |   |   |   | 215 |   |   |   | 220 |   |   |
|---|---|---|---|---|---|---|---|---|---|---|---|---|
| Trp | Ile | Cys | Val | Tyr | Leu | Ala | Ser | Asp | Glu | Ser | Lys | Phe | Ala | Thr | Gly |
| 225 |   |   |   | 230 |   |   |   | 235 |   |   |   | 240 |

|   |   |   |   | 245 |   |   |   | 250 |
|---|---|---|---|---|---|---|---|---|
| Ala | Glu | Phe | Val | Val | Asp | Gly | Gly | Tyr | Thr | Ala | Gln |

```
<210> SEQ ID NO 45
<211> LENGTH: 252
<212> TYPE: PRT
<213> ORGANISM: Artificial Sequence
<220> FEATURE:
<223> OTHER INFORMATION: Engineered Ketoreductase Sequence Formula with
      L. kefir backbone Synthetic Construct
<220> FEATURE:
<221> NAME/KEY: MISC_FEATURE
<222> LOCATION: (46)..(46)
<223> OTHER INFORMATION: Xaa is a basic residue
<220> FEATURE:
<221> NAME/KEY: MISC_FEATURE
<222> LOCATION: (72)..(72)
<223> OTHER INFORMATION: Xaa is an acidic residue
<220> FEATURE:
<221> NAME/KEY: MISC_FEATURE
<222> LOCATION: (82)..(82)
<223> OTHER INFORMATION: Xaa is a polar residue
<220> FEATURE:
<221> NAME/KEY: MISC_FEATURE
<222> LOCATION: (96)..(96)
<223> OTHER INFORMATION: Xaa is an aliphatic, basic, non-polar, or polar
      residue
<220> FEATURE:
<221> NAME/KEY: MISC_FEATURE
<222> LOCATION: (104)..(104)
<223> OTHER INFORMATION: Xaa is a non-polar or polar residue
<220> FEATURE:
<221> NAME/KEY: MISC_FEATURE
<222> LOCATION: (117)..(117)
<223> OTHER INFORMATION: Xaa is a polar or non-polar residue
<220> FEATURE:
<221> NAME/KEY: MISC_FEATURE
<222> LOCATION: (145)..(145)
<223> OTHER INFORMATION: Xaa is a polar residue
<220> FEATURE:
<221> NAME/KEY: MISC_FEATURE
<222> LOCATION: (147)..(147)
<223> OTHER INFORMATION: Xaa is an aliphatic, cysteine, or non-polar
      residue
<220> FEATURE:
<221> NAME/KEY: MISC_FEATURE
<222> LOCATION: (153)..(153)
<223> OTHER INFORMATION: Xaa is a polar residue
<220> FEATURE:
<221> NAME/KEY: MISC_FEATURE
<222> LOCATION: (157)..(157)
<223> OTHER INFORMATION: Xaa is a polar residue
<220> FEATURE:
<221> NAME/KEY: MISC_FEATURE
<222> LOCATION: (177)..(177)
<223> OTHER INFORMATION: Xaa is an acidic or basic residue
<220> FEATURE:
<221> NAME/KEY: MISC_FEATURE
<222> LOCATION: (178)..(178)
<223> OTHER INFORMATION: Xaa is a non-polar residue
<220> FEATURE:
<221> NAME/KEY: MISC_FEATURE
<222> LOCATION: (194)..(194)
<223> OTHER INFORMATION: Xaa is an aliphatic, constrained or non-polar
      residue
```

<220> FEATURE:
<221> NAME/KEY: MISC_FEATURE
<222> LOCATION: (195)..(195)
<223> OTHER INFORMATION: Xaa is an aliphatic, basic, or non-polar
      residue
<220> FEATURE:
<221> NAME/KEY: MISC_FEATURE
<222> LOCATION: (202)..(202)
<223> OTHER INFORMATION: Xaa is an aliphatic, basic, or non-polar
      residue
<220> FEATURE:
<221> NAME/KEY: MISC_FEATURE
<222> LOCATION: (223)..(223)
<223> OTHER INFORMATION: Xaa is an aliphatic or non-polar residue
<220> FEATURE:
<221> NAME/KEY: MISC_FEATURE
<222> LOCATION: (236)..(236)
<223> OTHER INFORMATION: Xaa is basic residue

<400> SEQUENCE: 45

```
Met Thr Asp Arg Leu Lys Gly Lys Val Ala Ile Val Thr Gly Gly Thr
1               5                   10                  15

Leu Gly Ile Gly Leu Ala Ile Ala Asp Lys Phe Val Glu Glu Gly Ala
            20                  25                  30

Lys Val Val Ile Thr Gly Arg His Ala Asp Val Gly Glu Xaa Ala Ala
        35                  40                  45

Lys Ser Ile Gly Gly Thr Asp Val Ile Arg Phe Val Gln His Asp Ala
    50                  55                  60

Ser Asp Glu Ala Gly Trp Thr Xaa Leu Phe Asp Thr Thr Glu Glu Ala
65                  70                  75                  80

Phe Xaa Pro Val Thr Thr Val Val Asn Asn Ala Gly Ile Ala Val Xaa
                85                  90                  95

Lys Ser Val Glu Asp Thr Thr Xaa Glu Glu Trp Arg Lys Leu Leu Ser
            100                 105                 110

Val Asn Leu Asp Xaa Val Phe Phe Gly Thr Arg Leu Gly Ile Gln Arg
        115                 120                 125

Met Lys Asn Lys Gly Leu Gly Ala Ser Ile Ile Asn Met Ser Ser Ile
    130                 135                 140

Xaa Gly Xaa Val Gly Asp Pro Thr Xaa Gly Ala Tyr Xaa Ala Ser Lys
145                 150                 155                 160

Gly Ala Val Arg Ile Met Ser Lys Ser Ala Ala Leu Asp Cys Ala Leu
                165                 170                 175

Xaa Xaa Tyr Asp Val Arg Val Asn Thr Val His Pro Gly Tyr Ile Lys
            180                 185                 190

Thr Xaa Xaa Val Asp Asp Leu Glu Gly Xaa Glu Glu Met Met Ser Gln
        195                 200                 205

Arg Thr Lys Thr Pro Met Gly His Ile Gly Glu Pro Asn Asp Xaa Ala
    210                 215                 220

Trp Ile Cys Val Tyr Leu Ala Ser Asp Glu Ser Xaa Phe Ala Thr Gly
225                 230                 235                 240

Ala Glu Phe Val Val Asp Gly Gly Tyr Thr Ala Gln
                245                 250
```

<210> SEQ ID NO 46
<211> LENGTH: 252
<212> TYPE: PRT
<213> ORGANISM: Artificial Sequence
<220> FEATURE:
<223> OTHER INFORMATION: Engineered Ketoreductase Sequence Formula
      with L. brevis backbone Synthetic Construct
<220> FEATURE:
<221> NAME/KEY: MISC_FEATURE
<222> LOCATION: (46)..(46)

```
<223> OTHER INFORMATION: Xaa is a basic residue
<220> FEATURE:
<221> NAME/KEY: MISC_FEATURE
<222> LOCATION: (72)..(72)
<223> OTHER INFORMATION: Xaa is an acidic residue
<220> FEATURE:
<221> NAME/KEY: MISC_FEATURE
<222> LOCATION: (82)..(82)
<223> OTHER INFORMATION: Xaa is a polar residue
<220> FEATURE:
<221> NAME/KEY: MISC_FEATURE
<222> LOCATION: (96)..(96)
<223> OTHER INFORMATION: Xaa is an aliphatic, basic, non-polar, or polar
      residue
<220> FEATURE:
<221> NAME/KEY: MISC_FEATURE
<222> LOCATION: (104)..(104)
<223> OTHER INFORMATION: Xaa is a non-polar or polar residue
<220> FEATURE:
<221> NAME/KEY: MISC_FEATURE
<222> LOCATION: (117)..(117)
<223> OTHER INFORMATION: Xaa is a polar or non-polar residue
<220> FEATURE:
<221> NAME/KEY: MISC_FEATURE
<222> LOCATION: (145)..(145)
<223> OTHER INFORMATION: Xaa is a polar residue
<220> FEATURE:
<221> NAME/KEY: MISC_FEATURE
<222> LOCATION: (147)..(147)
<223> OTHER INFORMATION: Xaa is an aliphatic, cysteine, or non-polar
      residue
<220> FEATURE:
<221> NAME/KEY: MISC_FEATURE
<222> LOCATION: (153)..(153)
<223> OTHER INFORMATION: Xaa is a polar residue
<220> FEATURE:
<221> NAME/KEY: MISC_FEATURE
<222> LOCATION: (157)..(157)
<223> OTHER INFORMATION: Xaa is a polar residue
<220> FEATURE:
<221> NAME/KEY: MISC_FEATURE
<222> LOCATION: (177)..(177)
<223> OTHER INFORMATION: Xaa is an acidic or basic residue
<220> FEATURE:
<221> NAME/KEY: MISC_FEATURE
<222> LOCATION: (178)..(178)
<223> OTHER INFORMATION: Xaa is a non-polar residue
<220> FEATURE:
<221> NAME/KEY: MISC_FEATURE
<222> LOCATION: (194)..(194)
<223> OTHER INFORMATION: Xaa is an aliphatic, constrained or non-polar
      residue
<220> FEATURE:
<221> NAME/KEY: MISC_FEATURE
<222> LOCATION: (195)..(195)
<223> OTHER INFORMATION: Xaa is an aliphatic, basic, or non-polar
      residue
<220> FEATURE:
<221> NAME/KEY: MISC_FEATURE
<222> LOCATION: (202)..(202)
<223> OTHER INFORMATION: Xaa is an aliphatic, basic, or non-polar
      residue
<220> FEATURE:
<221> NAME/KEY: MISC_FEATURE
<222> LOCATION: (223)..(223)
<223> OTHER INFORMATION: Xaa is an aliphatic or non-polar residue
<220> FEATURE:
<221> NAME/KEY: MISC_FEATURE
<222> LOCATION: (236)..(236)
<223> OTHER INFORMATION: Xaa is basic residue

<400> SEQUENCE: 46

Met Ser Asn Arg Leu Asp Gly Lys Val Ala Ile Ile Thr Gly Gly Thr
1               5                   10                  15

Leu Gly Ile Gly Leu Ala Ile Ala Thr Lys Phe Val Glu Glu Gly Ala
            20                  25                  30

Lys Val Met Ile Thr Gly Arg His Ser Asp Val Gly Glu Xaa Ala Ala
```

```
                  35                  40                  45

Lys Ser Val Gly Thr Pro Asp Gln Ile Gln Phe Phe Gln His Asp Ser
 50                  55                  60

Ser Asp Glu Asp Gly Trp Thr Xaa Leu Phe Asp Ala Thr Glu Lys Ala
 65                  70                  75                  80

Phe Xaa Pro Val Ser Thr Leu Val Asn Asn Ala Gly Ile Ala Val Xaa
                     85                  90                  95

Lys Ser Val Glu Glu Thr Thr Xaa Ala Glu Trp Arg Lys Leu Leu Ala
                100                 105                 110

Val Asn Leu Asp Xaa Val Phe Phe Gly Thr Arg Leu Gly Ile Gln Arg
                115                 120                 125

Met Lys Asn Lys Gly Leu Gly Ala Ser Ile Ile Asn Met Ser Ser Ile
130                 135                 140

Xaa Gly Xaa Val Gly Asp Pro Ser Xaa Gly Ala Tyr Xaa Ala Ser Lys
145                 150                 155                 160

Gly Ala Val Arg Ile Met Ser Lys Ser Ala Ala Leu Asp Cys Ala Leu
                165                 170                 175

Xaa Xaa Tyr Asp Val Arg Val Asn Thr Val His Pro Gly Tyr Ile Lys
                180                 185                 190

Thr Xaa Xaa Val Asp Asp Leu Pro Gly Xaa Glu Glu Ala Met Ser Gln
                195                 200                 205

Arg Thr Lys Thr Pro Met Gly His Ile Gly Glu Pro Asn Asp Xaa Ala
210                 215                 220

Tyr Ile Cys Val Tyr Leu Ala Ser Asn Glu Ser Xaa Phe Ala Thr Gly
225                 230                 235                 240

Ser Glu Phe Val Val Asp Gly Gly Tyr Thr Ala Gln
                245                 250

<210> SEQ ID NO 47
<211> LENGTH: 759
<212> TYPE: DNA
<213> ORGANISM: Lactobacillus minor

<400> SEQUENCE: 47
atgaccgatc ggttgaaggg gaaagtagca attgtaactg gcggtacctt gggaattggc      60
ttggcaatcg ctgataagtt tgttgaagaa ggcgcaaagg ttgttattac cggccgtcac     120
gctgatgtag gtgaaaaagc tgccagatca atcggcggca cagacgttat ccgttttgtc     180
caacacgatg cttctgatga accggctgg actaagttgt tgatacgac tgaagaagca     240
tttggcccag ttaccacggt tgtcaacaat gccggaattg cggtcagcaa gagtgttgaa     300
gataccacaa ctgaagaatg cgcaagctg ctctcagtta acttggatgg tgtcttcttc      360
ggtacccgtc ttggaatcca acgtatgaag aataaaggac tcggagcatc aatcatcaat     420
atgtcatcta tcgaaggttt tgttggtgat ccagctctgg gtgcatacaa cgcttcaaaa      480
ggtgctgtca gaattatgtc taaatcagct gccttggatt gcgctttgaa ggactacgat     540
gttcgggtta acactgttca tccaggttat atcaagacac cattggttga cgatcttgaa     600
ggggcagaag aaatgatgtc acagcggacc aagacaccaa tgggtcatat cggtgaacct     660
aacgatatcg cttggatctg tgtttacctg gcatctgacg aatctaaatt tgccactggt     720
gcagaattcg ttgtcgacgg agggtacacc gcccaatag                            759

<210> SEQ ID NO 48
<211> LENGTH: 252
<212> TYPE: PRT
<213> ORGANISM: Lactobacillus minor
```

<400> SEQUENCE: 48

Met Thr Asp Arg Leu Lys Gly Lys Val Ala Ile Val Thr Gly Gly Thr
1               5                   10                  15

Leu Gly Ile Gly Leu Ala Ile Ala Asp Lys Phe Val Glu Glu Gly Ala
            20                  25                  30

Lys Val Val Ile Thr Gly Arg His Ala Asp Val Gly Glu Lys Ala Ala
        35                  40                  45

Arg Ser Ile Gly Gly Thr Asp Val Ile Arg Phe Val Gln His Asp Ala
    50                  55                  60

Ser Asp Glu Thr Gly Trp Thr Lys Leu Phe Asp Thr Thr Glu Glu Ala
65                  70                  75                  80

Phe Gly Pro Val Thr Val Val Asn Asn Ala Gly Ile Ala Val Ser
                85                  90                  95

Lys Ser Val Glu Asp Thr Thr Glu Glu Trp Arg Lys Leu Leu Ser
            100                 105                 110

Val Asn Leu Asp Gly Val Phe Phe Gly Thr Arg Leu Gly Ile Gln Arg
        115                 120                 125

Met Lys Asn Lys Gly Leu Gly Ala Ser Ile Ile Asn Met Ser Ser Ile
130                 135                 140

Glu Gly Phe Val Gly Asp Pro Ala Leu Gly Ala Tyr Asn Ala Ser Lys
145                 150                 155                 160

Gly Ala Val Arg Ile Met Ser Lys Ser Ala Ala Leu Asp Cys Ala Leu
                165                 170                 175

Lys Asp Tyr Asp Val Arg Val Asn Thr Val His Pro Gly Tyr Ile Lys
            180                 185                 190

Thr Pro Leu Val Asp Asp Leu Glu Gly Ala Glu Glu Met Met Ser Gln
        195                 200                 205

Arg Thr Lys Thr Pro Met Gly His Ile Gly Glu Pro Asn Asp Ile Ala
    210                 215                 220

Trp Ile Cys Val Tyr Leu Ala Ser Asp Glu Ser Lys Phe Ala Thr Gly
225                 230                 235                 240

Ala Glu Phe Val Val Asp Gly Gly Tyr Thr Ala Gln
                245                 250

<210> SEQ ID NO 49
<211> LENGTH: 1056
<212> TYPE: DNA
<213> ORGANISM: Artificial Sequence
<220> FEATURE:
<223> OTHER INFORMATION: Codon optimized ADH from T. brockii

<400> SEQUENCE: 49
atgaaaggct tcgccatgct gagcatcggc aaagtgggtt ggattgaaaa agaaaaaccg      60
gcgccaggcc cgttcgatgc aattgtgcgc cctctggcag tagcgccgtg taccagcgat     120
attcatactg tgtttgaagg tgccattggc gagcgtcaca atatgattct gggccatgaa     180
gccgttggtg aagttgttga ggttggcagc gaagtgaagg atttcaaacc gggcgatcgc     240
gttgtcgttc cagcgattac cccggattgg cgcaccagcg aagtccagcg cggctaccat     300
cagcactctg gcggcatgct ggccggctgg aaattcagca atgtaaagga tggtgtgttc     360
ggtgaatttt tcacgttaa cgacgcagac atgaatctgg cgcacctgcc gaaagaaatc     420
ccgctggaag cagcggttat gattccggat atgatgacca cgggttttca cggcgcagag     480
ctggcggaca ttgaactggg cgctacggta gccgtactgg catcggtcc ggtgggcctg     540 atggcagttg caggcgctaa gctgcgcggc gcaggtcgta ttattgccgt tggttctcgc     600

```
ccggtgtgtg tggacgccgc taagtattat ggtgcaacgg acattgtcaa ttacaaggac    660
ggcccaattg aatctcagat catgaacctg acggaaggta aaggcgttga cgccgcgatt    720
atcgctggcg gcaacgccga catcatggcg accgcagtta aaatcgtcaa gccaggtggt    780
actattgcta acgtcaacta cttcggcgaa ggtgaggtcc tgcctgtccc acgtctggaa    840
tggggttgcg gtatggcaca taaaaccatt aaaggtggcc tgtgcccagg cggccgtctg    900
cgtatggaac gcctgatcga tctggtcttc tacaaacgcg tggatcctag caaactggtg    960
actcacgttt ccgcggctt tgataacatc gaaaaagctt ttatgctgat gaaagataaa   1020
ccgaaagatc tgattaaacc ggttgtcatc ctggct                             1056
```

<210> SEQ ID NO 50
<211> LENGTH: 352
<212> TYPE: PRT
<213> ORGANISM: Artificial Sequence
<220> FEATURE:
<223> OTHER INFORMATION: ADH from T. brockii

<400> SEQUENCE: 50

```
Met Lys Gly Phe Ala Met Leu Ser Ile Gly Lys Val Gly Trp Ile Glu
1               5                   10                  15

Lys Glu Lys Pro Ala Pro Gly Pro Phe Asp Ala Ile Val Arg Pro Leu
            20                  25                  30

Ala Val Ala Pro Cys Thr Ser Asp Ile His Thr Val Phe Glu Gly Ala
        35                  40                  45

Ile Gly Glu Arg His Asn Met Ile Leu Gly His Glu Ala Val Gly Glu
    50                  55                  60

Val Val Glu Val Gly Ser Glu Val Lys Asp Phe Lys Pro Gly Asp Arg
65                  70                  75                  80

Val Val Val Pro Ala Ile Thr Pro Asp Trp Arg Thr Ser Glu Val Gln
            85                  90                  95

Arg Gly Tyr His Gln His Ser Gly Gly Met Leu Ala Gly Trp Lys Phe
            100                 105                 110

Ser Asn Val Lys Asp Gly Val Phe Gly Glu Phe Phe His Val Asn Asp
        115                 120                 125

Ala Asp Met Asn Leu Ala His Leu Pro Lys Glu Ile Pro Leu Glu Ala
    130                 135                 140

Ala Val Met Ile Pro Asp Met Met Thr Thr Gly Phe His Gly Ala Glu
145                 150                 155                 160

Leu Ala Asp Ile Glu Leu Gly Ala Thr Val Ala Val Leu Gly Ile Gly
                165                 170                 175

Pro Val Gly Leu Met Ala Val Ala Gly Ala Lys Leu Arg Gly Ala Gly
            180                 185                 190

Arg Ile Ile Ala Val Gly Ser Arg Pro Val Cys Val Asp Ala Ala Lys
        195                 200                 205

Tyr Tyr Gly Ala Thr Asp Ile Val Asn Tyr Lys Asp Gly Pro Ile Glu
    210                 215                 220

Ser Gln Ile Met Asn Leu Thr Glu Gly Lys Gly Val Asp Ala Ala Ile
225                 230                 235                 240

Ile Ala Gly Gly Asn Ala Asp Ile Met Ala Thr Ala Val Lys Ile Val
                245                 250                 255

Lys Pro Gly Gly Thr Ile Ala Asn Val Asn Tyr Phe Gly Glu Gly Glu
            260                 265                 270

Val Leu Pro Val Pro Arg Leu Glu Trp Gly Cys Gly Met Ala His Lys
        275                 280                 285
```

```
Thr Ile Lys Gly Gly Leu Cys Pro Gly Gly Arg Leu Arg Met Glu Arg
    290                 295                 300

Leu Ile Asp Leu Val Phe Tyr Lys Arg Val Asp Pro Ser Lys Leu Val
305                 310                 315                 320

Thr His Val Phe Arg Gly Phe Asp Asn Ile Glu Lys Ala Phe Met Leu
                325                 330                 335

Met Lys Asp Lys Pro Lys Asp Leu Ile Lys Pro Val Val Ile Leu Ala
                340                 345                 350

<210> SEQ ID NO 51
<211> LENGTH: 1125
<212> TYPE: DNA
<213> ORGANISM: Artificial Sequence
<220> FEATURE:
<223> OTHER INFORMATION: Codon optimized ADH from Horse Liver, E isozyme

<400> SEQUENCE: 51
atgagcacag cagggaaagt aattaaatgc aaagcagctg tgctgtggga ggaaaagaaa      60
ccatttccca ttgaggaggt ggaggtcgca cctccgaagg cccatgaagt ccgtattaag     120
atggtggcca cagggatctg tcgctcagat gaccacgtgg ttagtgggac cctggtcaca     180
cctctgcctg tgatcgcagg ccatgaggca gctggcattg tggagagcat cggggaaggc     240
gtcactcaag tacgtccagg tgataaagtc atcccactgt ttactcctca gtgtgggaaa     300
tgccgtgttt gtaaacaccc tgaaggcaac ttctgcttga aaatgatctc gagcatgcct     360
cgtgggacca tgcaggatgg taccagccgt tcacctgccg tgggaagcc tatccaccac     420 ttcctgggca ccagcacctt ctcccagtac accgtggtgg acgagatctc agtggccaag     480
atcgatgcgg cctcaccgct ggagaaagtc tgtctgattg ctgtgggtt ttctactggt     540 tatgggtctg cagtcaaggt tgccaaggtc acccagggct ccacctgtgc cgtgtttggc     600
ctgggggggg tgggcctgtc tgttatcatg ggctgtaaag cagccgggc ggcccgtatc     660 attggggtgg acatcaacaa agacaagttt gcaaggcca agaagtggg tgccactgag     720 tgtgtcaacc ctcaggacta caagaaacct atccaggagg tgctgacaga aatgagcaat     780
gggggcgtgg attttcatt tgaagtcatt ggtcgtctgg acaccatggt gactgccttg     840
tcatgctgtc aagaagcata tggtgtgagc gtcatcgtag gggtacctcc tgattcccaa     900
aatctgtcta tgaatcctat gttgctgctg agtgggcgta cctggaaagg ggctatttt     960 ggtggtttta agagtaaaga ttctgtccct aaactggtgg ccgatttat ggctaaaaag    1020 tttgcactgg atcctttaat cacccatgtt ttaccttttg aaaaaattaa tgaagggttt    1080
gacctgctgc gctctgggga gagtatccgt accatcctga cgttt                    1125

<210> SEQ ID NO 52
<211> LENGTH: 375
<212> TYPE: PRT
<213> ORGANISM: Artificial Sequence
<220> FEATURE:
<223> OTHER INFORMATION: ADH from Horse Liver, E isozyme

<400> SEQUENCE: 52

Met Ser Thr Ala Gly Lys Val Ile Lys Cys Lys Ala Ala Val Leu Trp
1               5                   10                  15

Glu Glu Lys Lys Pro Phe Ser Ile Glu Glu Val Glu Val Ala Pro Pro
            20                  25                  30

Lys Ala His Glu Val Arg Ile Lys Met Val Ala Thr Gly Ile Cys Arg
        35                  40                  45
```

| Ser | Asp | Asp | His | Val | Val | Ser | Gly | Thr | Leu | Val | Thr | Pro | Leu | Pro | Val |
|---|---|---|---|---|---|---|---|---|---|---|---|---|---|---|---|
| 50 | | | | | 55 | | | | | 60 | | | | | |

| Ile | Ala | Gly | His | Glu | Ala | Ala | Gly | Ile | Val | Glu | Ser | Ile | Gly | Glu | Gly |
|---|---|---|---|---|---|---|---|---|---|---|---|---|---|---|---|
| 65 | | | | 70 | | | | | 75 | | | | | 80 | |

| Val | Thr | Thr | Val | Arg | Pro | Gly | Asp | Lys | Val | Ile | Pro | Leu | Phe | Thr | Pro |
|---|---|---|---|---|---|---|---|---|---|---|---|---|---|---|---|
| | | | | 85 | | | | | 90 | | | | | 95 | |

| Gln | Cys | Gly | Lys | Cys | Arg | Val | Cys | Lys | His | Pro | Glu | Gly | Asn | Phe | Cys |
|---|---|---|---|---|---|---|---|---|---|---|---|---|---|---|---|
| | | | 100 | | | | | 105 | | | | | 110 | | |

| Leu | Lys | Asn | Asp | Leu | Ser | Met | Pro | Arg | Gly | Thr | Met | Gln | Asp | Gly | Thr |
|---|---|---|---|---|---|---|---|---|---|---|---|---|---|---|---|
| | | | 115 | | | | | 120 | | | | | 125 | | |

| Ser | Arg | Phe | Thr | Cys | Arg | Gly | Lys | Pro | Ile | His | Phe | Leu | Gly | Thr |
|---|---|---|---|---|---|---|---|---|---|---|---|---|---|---|
| | 130 | | | | | 135 | | | | | 140 | | | |

| Ser | Thr | Phe | Ser | Gln | Tyr | Thr | Val | Val | Asp | Glu | Ile | Ser | Val | Ala | Lys |
|---|---|---|---|---|---|---|---|---|---|---|---|---|---|---|---|
| 145 | | | | | 150 | | | | | 155 | | | | | 160 |

| Ile | Asp | Ala | Ala | Ser | Pro | Leu | Glu | Lys | Val | Cys | Leu | Ile | Gly | Cys | Gly |
|---|---|---|---|---|---|---|---|---|---|---|---|---|---|---|---|
| | | | | 165 | | | | | 170 | | | | | 175 | |

| Phe | Ser | Thr | Gly | Tyr | Gly | Ser | Ala | Val | Lys | Val | Ala | Lys | Val | Thr | Gln |
|---|---|---|---|---|---|---|---|---|---|---|---|---|---|---|---|
| | | | 180 | | | | | 185 | | | | | 190 | | |

| Gly | Ser | Thr | Cys | Ala | Val | Phe | Gly | Leu | Gly | Gly | Val | Gly | Leu | Ser | Val |
|---|---|---|---|---|---|---|---|---|---|---|---|---|---|---|---|
| | | 195 | | | | | 200 | | | | | 205 | | | |

| Ile | Met | Gly | Cys | Lys | Ala | Ala | Gly | Ala | Ala | Arg | Ile | Ile | Gly | Val | Asp |
|---|---|---|---|---|---|---|---|---|---|---|---|---|---|---|---|
| 210 | | | | | 215 | | | | | 220 | | | | | |

| Ile | Asn | Lys | Asp | Lys | Phe | Ala | Lys | Ala | Lys | Glu | Val | Gly | Ala | Thr | Glu |
|---|---|---|---|---|---|---|---|---|---|---|---|---|---|---|---|
| 225 | | | | 230 | | | | | 235 | | | | | 240 | |

| Cys | Val | Asn | Pro | Gln | Asp | Tyr | Lys | Lys | Pro | Ile | Gln | Glu | Val | Leu | Thr |
|---|---|---|---|---|---|---|---|---|---|---|---|---|---|---|---|
| | | | 245 | | | | | 250 | | | | | 255 | | |

| Glu | Met | Ser | Asn | Gly | Gly | Val | Asp | Phe | Ser | Phe | Glu | Val | Ile | Gly | Arg |
|---|---|---|---|---|---|---|---|---|---|---|---|---|---|---|---|
| | | 260 | | | | | 265 | | | | | 270 | | | |

| Leu | Asp | Thr | Met | Val | Thr | Ala | Leu | Ser | Cys | Cys | Gln | Glu | Ala | Tyr | Gly |
|---|---|---|---|---|---|---|---|---|---|---|---|---|---|---|---|
| | | 275 | | | | | 280 | | | | | 285 | | | |

| Val | Ser | Val | Ile | Val | Gly | Val | Pro | Pro | Asp | Ser | Gln | Asn | Leu | Ser | Met |
|---|---|---|---|---|---|---|---|---|---|---|---|---|---|---|---|
| 290 | | | | | 295 | | | | | 300 | | | | | |

| Asn | Pro | Met | Leu | Leu | Leu | Ser | Gly | Arg | Thr | Trp | Lys | Gly | Ala | Ile | Phe |
|---|---|---|---|---|---|---|---|---|---|---|---|---|---|---|---|
| 305 | | | | | 310 | | | | | 315 | | | | | 320 |

| Gly | Gly | Phe | Lys | Ser | Lys | Asp | Ser | Val | Pro | Lys | Leu | Val | Ala | Asp | Phe |
|---|---|---|---|---|---|---|---|---|---|---|---|---|---|---|---|
| | | | 325 | | | | | 330 | | | | | 335 | | |

| Met | Ala | Lys | Lys | Phe | Ala | Leu | Asp | Pro | Leu | Ile | Thr | His | Val | Leu | Pro |
|---|---|---|---|---|---|---|---|---|---|---|---|---|---|---|---|
| | | | 340 | | | | | 345 | | | | | 350 | | |

| Phe | Glu | Lys | Ile | Asn | Glu | Gly | Phe | Asp | Leu | Leu | Arg | Ser | Gly | Glu | Ser |
|---|---|---|---|---|---|---|---|---|---|---|---|---|---|---|---|
| | | | 355 | | | | | 360 | | | | | 365 | | |

| Ile | Arg | Thr | Ile | Leu | Thr | Phe |
|---|---|---|---|---|---|---|
| 370 | | | | | 375 | |

<210> SEQ ID NO 53
<211> LENGTH: 1122
<212> TYPE: DNA
<213> ORGANISM: Artificial Sequence
<220> FEATURE:
<223> OTHER INFORMATION: Codon optimized ADH from Horse Liver, S isozyme

<400> SEQUENCE: 53

| atgagcacag caggaaaagt aattaaatgc aaagcagctg tgctgtggga gcaaaagaaa | 60 |
| ccatttttcca ttgaggaggt ggaggtcgca cctccgaagg cccatgaagt ccgtattaag | 120 |
| atggtggccg cagggatctg tcgctcagat gaccacgtgg ttagtgggac cctggtcgca | 180 |
| cctctgcctg tgatcgcagg ccatgaggca gctggcattg tggagagcat cggggaaggc | 240 |

```
gtcactacag tacgtccagg tgataaagtc atcccactgt ttattcctca gtgtgggaaa    300
tgcagtgttt gtaaacaccc tgaaggcaac ctgtgcttga aaaatctgag catgcctcgt    360
gggaccatgc aggatggtac cagccgtttc acctgccgtg ggaagcctat ccaccacttc    420
ctgggcacca gcaccttctc ccagtacacc gtggtggacg agatctcagt ggccaagatc    480
gatgcggcct accgctgga gaaagtctgt ctggttggct gtgggttttc tactggttat    540
gggtctgcag tcaaggttgc caaggtcacc cagggctcca cctgtgccgt gtttggcctg    600
ggggggggtgg gcctgtctgt tatcatgggc tgtaaagcag ccggggcggc ccgtatcatt    660
ggggtggaca tcaacaaaga caagtttgca aaggccaaag aagtgggtgc cactgagtgt    720
gtcaaccctc aggactacaa gaaacctatc caggaggtgc tgacagaaat gagcaatggg    780
ggcgtggatt tttcatttga agtcattggt cgtctggaca ccatggtggc tgccttgtca    840
tgctgtcaag aagcatatgg tgtgagcgtc atcgtagggg tacctcctga ttcccaaaat    900
ctgtctatga atcctatgtt gctgctgagt gggcgtacct ggaaagggc tattttttggt    960
ggttttaaga gtaaagattc tgtccctaaa ctggtggccg attttatggc taaaaagttt   1020
gcactggatc ctttaatcac ccatgttta ccttttgaaa aaattaatga agggtttgac   1080
ctgctgcgct ctgggaagag tatccgtacc atcctgacgt tt                     1122
```

<210> SEQ ID NO 54
<211> LENGTH: 374
<212> TYPE: PRT
<213> ORGANISM: Artificial Sequence
<220> FEATURE:
<223> OTHER INFORMATION: ADH from Horse Liver, S isozyme

<400> SEQUENCE: 54

```
Met Ser Thr Ala Gly Lys Val Ile Lys Cys Lys Ala Ala Val Leu Trp
1               5                   10                  15

Glu Gln Lys Lys Pro Phe Ser Ile Glu Glu Val Glu Val Ala Pro Pro
            20                  25                  30

Lys Ala His Glu Val Arg Ile Lys Met Val Ala Ala Gly Ile Cys Arg
        35                  40                  45

Ser Asp Asp His Val Val Ser Gly Thr Leu Val Ala Pro Leu Pro Val
    50                  55                  60

Ile Ala Gly His Glu Ala Ala Gly Ile Val Glu Ser Ile Gly Glu Gly
65                  70                  75                  80

Val Thr Thr Val Arg Pro Gly Asp Lys Val Ile Pro Leu Phe Ile Pro
                85                  90                  95

Gln Cys Gly Lys Cys Ser Val Cys Lys His Pro Glu Gly Asn Leu Cys
            100                 105                 110

Leu Lys Asn Leu Ser Met Pro Arg Gly Thr Met Gln Asp Gly Thr Ser
        115                 120                 125

Arg Phe Thr Cys Arg Gly Lys Pro Ile His His Phe Leu Gly Thr Ser
    130                 135                 140

Thr Phe Ser Gln Tyr Thr Val Val Asp Glu Ile Ser Val Ala Lys Ile
145                 150                 155                 160

Asp Ala Ala Ser Pro Leu Glu Lys Val Cys Leu Val Gly Cys Gly Phe
                165                 170                 175

Ser Thr Gly Tyr Gly Ser Ala Val Lys Val Ala Lys Val Thr Gln Gly
            180                 185                 190

Ser Thr Cys Ala Val Phe Gly Leu Gly Gly Val Gly Leu Ser Val Ile
        195                 200                 205
```

```
Met Gly Cys Lys Ala Ala Gly Ala Ala Arg Ile Ile Gly Val Asp Ile
    210                 215                 220

Asn Lys Asp Lys Phe Ala Lys Ala Lys Glu Val Gly Ala Thr Glu Cys
225                 230                 235                 240

Val Asn Pro Gln Asp Tyr Lys Lys Pro Ile Gln Glu Val Leu Thr Glu
                245                 250                 255

Met Ser Asn Gly Gly Val Asp Phe Ser Phe Glu Val Ile Gly Arg Leu
            260                 265                 270

Asp Thr Met Val Ala Ala Leu Ser Cys Cys Gln Glu Ala Tyr Gly Val
        275                 280                 285

Ser Val Ile Val Gly Val Pro Pro Asp Ser Gln Asn Leu Ser Met Asn
    290                 295                 300

Pro Met Leu Leu Leu Ser Gly Arg Thr Trp Lys Gly Ala Ile Phe Gly
305                 310                 315                 320

Gly Phe Lys Ser Lys Asp Ser Val Pro Lys Leu Val Ala Asp Phe Met
                325                 330                 335

Ala Lys Lys Phe Ala Leu Asp Pro Leu Ile Thr His Val Leu Pro Phe
            340                 345                 350

Glu Lys Ile Asn Glu Gly Phe Asp Leu Leu Arg Ser Gly Lys Ser Ile
        355                 360                 365

Arg Thr Ile Leu Thr Phe
    370

<210> SEQ ID NO 55
<211> LENGTH: 762
<212> TYPE: DNA
<213> ORGANISM: Artificial Sequence
<220> FEATURE:
<223> OTHER INFORMATION: Codon optimized ADH from O. oeni

<400> SEQUENCE: 55
atggtcgatc gcctgaaagg taaggtttca attgtgacgg ggggcaccct gggtatcggc      60
ttgtcgattg tcgacctgta cttgaaagaa ggcgccaaag tggtgttcac tggccgtcgc     120
cagaaaattg ggaggaggc attcaaacac ttgtctaacc cgaaaaacgc aaagttcgtg     180
gttcacgatg ctagcaacga agaaggttgg aaaaaactgt ttgccgatgt tattgccgaa     240
ttcggcaaag tggatattct ggtcaataac gcaggcattg gtgtaccggg cgatgtcgag     300
cacacggatt atgcgcaatg cgtcaaact atggcggtga acctggacgg cgtatacttc     360
ggtactcatt atggtgtaat caacatgaaa caccctgtct ccggtgacgc ctctatcatt     420
aatatgtcct cgattgaagg tttggtaggt gatccaaatc tgttcgccta caacgcaact     480
aaaggcgctc tgcgcatcat gaccaaaagc gccgcgattt actgcgcgca gaacgattac     540
aacctgcgca ttaataccat ccacccgggt tatatcaaaa ctccgttagt agaagacatg     600
gatgggtttg agaaagcgat gtccgaacgc acgaaaaccc ctatgggcca cattggcgat     660
ccggaggaca tcggttggct ggcagtgtat ctgggttcag aagaagcaaa atttgccacg     720
ggcagcgaat tcacagtcga cggtggctac accgcacagt aa                        762

<210> SEQ ID NO 56
<211> LENGTH: 253
<212> TYPE: PRT
<213> ORGANISM: Artificial Sequence
<220> FEATURE:
<223> OTHER INFORMATION: ADH from O. oeni

<400> SEQUENCE: 56

Met Val Asp Arg Leu Lys Gly Lys Val Ser Ile Val Thr Gly Gly Thr
```

```
                1               5                  10                 15
Leu Gly Ile Gly Leu Ser Ile Val Asp Leu Tyr Leu Lys Glu Gly Ala
                   20                  25                 30

Lys Val Val Phe Thr Gly Arg Arg Gln Lys Ile Gly Glu Glu Ala Phe
                   35                  40                 45

Lys His Leu Ser Asn Pro Lys Asn Ala Lys Phe Val Val His Asp Ala
                   50                  55                 60

Ser Asn Glu Glu Gly Trp Lys Lys Leu Phe Ala Asp Val Ile Ala Glu
65                      70                  75                 80

Phe Gly Lys Val Asp Ile Leu Val Asn Asn Ala Gly Ile Gly Val Pro
                   85                  90                 95

Gly Asp Val Glu His Thr Asp Tyr Ala Gln Trp Arg Gln Thr Met Ala
                   100                 105                110

Val Asn Leu Asp Gly Val Tyr Phe Gly Thr His Tyr Gly Val Ile Asn
                   115                 120                125

Met Lys His Pro Val Ser Gly Asp Ala Ser Ile Ile Asn Met Ser Ser
                   130                 135                140

Ile Glu Gly Leu Val Gly Asp Pro Asn Leu Phe Ala Tyr Asn Ala Thr
145                     150                 155                160

Lys Gly Ala Leu Arg Ile Met Thr Lys Ser Ala Ala Ile Tyr Cys Ala
                   165                 170                175

Gln Asn Asp Tyr Asn Leu Arg Ile Asn Thr Ile His Pro Gly Tyr Ile
                   180                 185                190

Lys Thr Pro Leu Val Glu Asp Met Asp Gly Phe Glu Lys Ala Met Ser
                   195                 200                205

Glu Arg Thr Lys Thr Pro Met Gly His Ile Gly Asp Pro Glu Asp Ile
                   210                 215                220

Gly Trp Leu Ala Val Tyr Leu Gly Ser Glu Glu Ala Lys Phe Ala Thr
225                     230                 235                240

Gly Ser Glu Phe Thr Val Asp Gly Gly Tyr Thr Ala Gln
                   245                 250

<210> SEQ ID NO 57
<211> LENGTH: 252
<212> TYPE: PRT
<213> ORGANISM: Artificial sequence
<220> FEATURE:
<223> OTHER INFORMATION: Engineered Ketoreductase Sequence Formula with
      L. minor backbone Synthetic Construct
<220> FEATURE:
<221> NAME/KEY: MISC_FEATURE
<222> LOCATION: (46)..(46)
<223> OTHER INFORMATION: Xaa is a basic residue
<220> FEATURE:
<221> NAME/KEY: MISC_FEATURE
<222> LOCATION: (72)..(72)
<223> OTHER INFORMATION: Xaa is an acidic residue
<220> FEATURE:
<221> NAME/KEY: MISC_FEATURE
<222> LOCATION: (82)..(82)
<223> OTHER INFORMATION: Xaa is a polar residue
<220> FEATURE:
<221> NAME/KEY: MISC_FEATURE
<222> LOCATION: (96)..(96)
<223> OTHER INFORMATION: Xaa is an aliphatic, basic, non-polar, or polar
      residue
<220> FEATURE:
<221> NAME/KEY: MISC_FEATURE
<222> LOCATION: (104)..(104)
<223> OTHER INFORMATION: Xaa is a non-polar or polar residue
<220> FEATURE:
<221> NAME/KEY: MISC_FEATURE
<222> LOCATION: (117)..(117)
<223> OTHER INFORMATION: Xaa is a polar or non-polar residue
```

```
<220> FEATURE:
<221> NAME/KEY: MISC_FEATURE
<222> LOCATION: (145)..(145)
<223> OTHER INFORMATION: Xaa is a polar residue
<220> FEATURE:
<221> NAME/KEY: MISC_FEATURE
<222> LOCATION: (147)..(147)
<223> OTHER INFORMATION: Xaa is an aliphatic, cysteine, or non-polar
      residue
<220> FEATURE:
<221> NAME/KEY: MISC_FEATURE
<222> LOCATION: (153)..(153)
<223> OTHER INFORMATION: Xaa is a polar residue
<220> FEATURE:
<221> NAME/KEY: MISC_FEATURE
<222> LOCATION: (157)..(157)
<223> OTHER INFORMATION: Xaa is a polar residue
<220> FEATURE:
<221> NAME/KEY: MISC_FEATURE
<222> LOCATION: (177)..(177)
<223> OTHER INFORMATION: Xaa is an acidic or basic residue
<220> FEATURE:
<221> NAME/KEY: MISC_FEATURE
<222> LOCATION: (178)..(178)
<223> OTHER INFORMATION: Xaa is a non-polar residue
<220> FEATURE:
<221> NAME/KEY: MISC_FEATURE
<222> LOCATION: (194)..(194)
<223> OTHER INFORMATION: Xaa is an aliphatic, constrained or non-polar
      residue
<220> FEATURE:
<221> NAME/KEY: MISC_FEATURE
<222> LOCATION: (195)..(195)
<223> OTHER INFORMATION: Xaa is an aliphatic, basic, or non-polar
      residue
<220> FEATURE:
<221> NAME/KEY: MISC_FEATURE
<222> LOCATION: (202)..(202)
<223> OTHER INFORMATION: Xaa is an aliphatic, basic, or non-polar
      residue
<220> FEATURE:
<221> NAME/KEY: MISC_FEATURE
<222> LOCATION: (223)..(223)
<223> OTHER INFORMATION: Xaa is an aliphatic or non-polar residue
<220> FEATURE:
<221> NAME/KEY: MISC_FEATURE
<222> LOCATION: (236)..(236)
<223> OTHER INFORMATION: Xaa is basic residue

<400> SEQUENCE: 57

Met Thr Asp Arg Leu Lys Gly Lys Val Ala Ile Val Thr Gly Gly Thr
1               5                   10                  15

Leu Gly Ile Gly Leu Ala Ile Ala Asp Lys Phe Val Glu Glu Gly Ala
            20                  25                  30

Lys Val Val Ile Thr Gly Arg His Ala Asp Val Gly Glu Xaa Ala Ala
        35                  40                  45

Arg Ser Ile Gly Gly Thr Asp Val Ile Arg Phe Val Gln His Asp Ala
    50                  55                  60

Ser Asp Glu Thr Gly Trp Thr Xaa Leu Phe Asp Thr Thr Glu Glu Ala
65                  70                  75                  80

Phe Xaa Pro Val Thr Thr Val Val Asn Asn Ala Gly Ile Ala Val Xaa
                85                  90                  95

Lys Ser Val Glu Asp Thr Thr Xaa Glu Glu Trp Arg Lys Leu Leu Ser
            100                 105                 110

Val Asn Leu Asp Xaa Val Phe Phe Gly Thr Arg Leu Gly Ile Gln Arg
        115                 120                 125

Met Lys Asn Lys Gly Leu Gly Ala Ser Ile Ile Asn Met Ser Ser Ile
    130                 135                 140

Xaa Gly Xaa Val Gly Asp Pro Ala Xaa Gly Ala Tyr Xaa Ala Ser Lys
145                 150                 155                 160
```

```
Gly Ala Val Arg Ile Met Ser Lys Ser Ala Ala Leu Asp Cys Ala Leu
            165                 170                 175

Xaa Xaa Tyr Asp Val Arg Val Asn Thr Val His Pro Gly Tyr Ile Lys
            180                 185                 190

Thr Xaa Xaa Val Asp Asp Leu Glu Gly Xaa Glu Glu Met Met Ser Gln
        195                 200                 205

Arg Thr Lys Thr Pro Met Gly His Ile Gly Glu Pro Asn Asp Xaa Ala
        210                 215                 220

Trp Ile Cys Val Tyr Leu Ala Ser Asp Glu Ser Xaa Phe Ala Thr Gly
225                 230                 235                 240

Ala Glu Phe Val Val Asp Gly Gly Tyr Thr Ala Gln
            245                 250
```